United States Patent
Saveh Shemshaki et al.

(10) Patent No.: US 12,102,730 B2
(45) Date of Patent: Oct. 1, 2024

(54) GRAPHENE-BASED NANOFIBERS FOR SKELETAL MUSCLE TISSUE REGENERATION

(71) Applicant: University of Connecticut, Farmington, CT (US)

(72) Inventors: Nikoo Saveh Shemshaki, Farmington, CT (US); Cato Laurencin, Farmington, CT (US)

(73) Assignee: University of Connecticut, Farmington, CT (US)

( * ) Notice: Subject to any disclaimer, the term of this patent is extended or adjusted under 35 U.S.C. 154(b) by 328 days.

(21) Appl. No.: 17/352,189

(22) Filed: Jun. 18, 2021

(65) Prior Publication Data

US 2021/0402054 A1    Dec. 30, 2021

Related U.S. Application Data

(60) Provisional application No. 63/041,594, filed on Jun. 19, 2020.

(51) Int. Cl.
| | | |
|---|---|---|
| *A61L 27/00* | (2006.01) | |
| *A61L 27/08* | (2006.01) | |
| *A61L 27/18* | (2006.01) | |
| *A61L 27/22* | (2006.01) | |
| *A61L 27/24* | (2006.01) | |
| *A61L 27/50* | (2006.01) | |

(52) U.S. Cl.
CPC ............... *A61L 27/08* (2013.01); *A61L 27/18* (2013.01); *A61L 27/222* (2013.01); *A61L 27/24* (2013.01); *A61L 27/50* (2013.01); *A61L 2400/12* (2013.01); *A61L 2430/30* (2013.01)

(58) Field of Classification Search
CPC .......... A61F 2/2418; A61F 2/28; B29C 64/40; B33Y 70/00; A61L 27/08; A61L 27/222; A61L 27/24; A61L 27/50; A61L 27/18; A61L 27/12; A61L 27/30
See application file for complete search history.

(56) References Cited

U.S. PATENT DOCUMENTS 10,420,861 B2 * 9/2019 Jeong ...................... A61L 27/18
2018/0050495 A1 * 2/2018 Stolyarov ................ C08J 5/041

OTHER PUBLICATIONS

Grasman, J.M., et al., Biomimetic scaffolds for regeneration of volumetric muscle loss in skeletal muscle injuries. Acta biomaterialia, 2015. 25: p. 2-15.
Matthias, N., et al., Volumetric muscle loss injury repair using in situ fibrin gel cast seeded with muscle-derived stem cells (MDSCs). Stem cell research, 2018. 27: p. 65-73.
Zhang, Z., et al., Electroactive Scaffolds for Neurogenesis and Myogenesis: Graphene-Based Nanomaterials. Small, 2018. 14(48): p. 1801983.
Saveh-Shemshaki, N., L. S.Nair, and C.T. Laurencin, Nanofiber-based matrices for rotator cuff regenerative engineering. Acta Biomaterialia, 2019. 94: p. 64-81.

(Continued)

*Primary Examiner* — Jason-Dennis N Stewart
(74) *Attorney, Agent, or Firm* — McDonnell Boehnen Hulbert & Berghoff LLP

(57) ABSTRACT

The disclosure is directed to scaffolds comprising nanofibers of graphene nanoplatelets and a biocompatible polymer, as well as methods for making and using such scaffolds.

12 Claims, 38 Drawing Sheets

(56) References Cited

OTHER PUBLICATIONS

Tang, X., et al., Biomimetic Electroconductive Nanofibrous Matrices for Skeletal Muscle Regenerative Engineering. Regenerative Engineering and Translational Medicine, 2019: p. 1-10.
Saveh-Shemshaki, N., et al., Synthesis of mesoporous functional hematite nanofibrous photoanodes by electrospinning. Polymers for Advanced Technologies, 2016. 27(3): p. 358-365.
Saveh-Shemshaki, N., R. Bagherzadeh, and M. Latifi, Electrospun metal oxide nanofibrous mat as a transparent conductive layer. Organic Electronics, 2019. 70: p. 131-139.
Saveh-Shemshakia, N., et al., Functional Fe2O3 Nanofiber Photoanodes for Photoelectrochemical Water Splitting Application.
Chen, M.-C., Y.-C. Sun, and Y.-H. Chen, Electrically conductive nanofibers with highly oriented structures and their potential application in skeletal muscle tissue engineering. Acta biomaterialia, 2013. 9(3): p. 5562-5572.
Saveh-Shemshaki, N., L. S.Nair, and C.T. Laurencin, Nanofiber-based Matrices for Rotator Cuff Regenerative Engineering. Acta Biomaterialia, 2019.
Patel, A., et al., Carbon-based hierarchical scaffolds for myoblast differentiation: Synergy between nano-functionalization and alignment. Acta Biomaterialia, 2016. 32: p. 77-88.
Du, Y., et al., Biomimetic elastomeric, conductive and biodegradable polycitrate-based nanocomposites for guiding myogenic differentiation and skeletal muscle regeneration. Biomaterials, 2018. 157: p. 40-50.
Gajendiran, M., et al., Conductive biomaterials for tissue engineering applications. Journal of Industrial and Engineering Chemistry, 2017. 51: p. 12-26.
Yang, H.S., et al., Electroconductive nanopatterned substrates for enhanced myogenic differentiation and maturation. Advanced healthcare materials, 2016. 5(1): p. 137-145.
Porter, G.A., R.F. Makuck, and S.A. Rivkees, Reduction in intracellular calcium levels inhibits myoblast differentiation. Journal of Biological Chemistry, 2002. 277(32): p. 28942-28947.
Pedrotty, D.M., et al., Engineering skeletal myoblasts: roles of three-dimensional culture and electrical stimulation. American Journal of Physiology-Heart and Circulatory Physiology, 2005. 288(4): p. H1620-H1626.
Björnineen, M., et al., Electrically stimulated adipose stem cells on polypyrrole-coated scaffolds for smooth muscle tissue engineering. Annals of biomedical engineering, 2017. 45(4): p. 1015-1026.
Mahmoudifard, M., et al., The different fate of satellite cells on conductive composite electrospun nanofibers with graphene and graphene oxide nanosheets. Biomedical Materials, 2016. 11(2): p. 025006.
Shin, S.R., et al., Graphene-based materials for tissue engineering. Advanced drug delivery reviews, 2016. 105: p. 255-274.0
Jo, S.B., et al., Nano-graphene oxide/polyurethane nanofibers: mechanically flexible and myogenic stimulating matrix for skeletal tissue engineering. Journal of tissue engineering, 2020. 11: p. 2041731419900424.1;
Rauti, R., et al., Graphene oxide nanosheets reshape synaptic function in cultured brain networks. ACS nano, 2016. 10 (4): p. 4459-4471.
Fabbro, A., et al., Graphene-based interfaces do not alter target nerve cells. ACS nano, 2016. 10(1): p. 615-623.
Hong, S.W., et al., Enhanced neural cell adhesion and neurite outgrowth on graphene-based biomimetic substrates. BioMed research international, 2014. 2014.
Ryan, A.J., et al., Electroconductive biohybrid collagen/pristine graphene composite biomaterials with enhanced biological activity. Advanced Materials, 2018. 30(15): p. 1706442.
Graphene Nanoplatelets Non Functionalized. Available from: https://www.cheaptubes.com/product/graphene-nanoplatelets-non-functionalized/ As captured May 9, 2024.
Shen, M.-Y., et al., Mechanical properties and tensile fatigue of graphene nanoplatelets reinforced polymer nanocomposites. Journal of Nanomaterials, 2013. 2013.
Nagiah, N., et al., Development and characterization of coaxially electrospun gelatin coated poly (3-hydroxybutyric acid) thin films as potential scaffolds for skin regeneration. Materials Science and Engineering: C, 2013. 33(7): p. 4444-4452.
Schroder, D.K., Resistivity, in Semiconductor Material and Device Characterization. 2005.
Ding, Y., M.A. Invernale, and G.A. Sotzing, Conductivity Trends of PEDOT-PSS Impregnated Fabric and the Effect of Conductivity on Electrochromic Textile. ACS Applied Materials & Interfaces, 2010. 2(6): p. 1588-1593.
Ku, S.H., S.H. Lee, and C.B. Park, Synergic effects of nanofiber alignment and electroactivity on myoblast differentiation. Biomaterials, 2012. 33(26): p. 6098-6104.
Dai, J., et al., Effects of functionalized graphene nanoplatelets on the morphology and properties of phenolic resins. Journal of Nanomaterials, 2016. 2016.
Chatterjee, S., et al., Mechanical reinforcement and thermal conductivity in expanded graphene nanoplatelets reinforced epoxy composites. Chemical Physics Letters, 2012. 531: p. 6-10.
Vilay, V., et al., Improvement of microstructures and properties of biodegradable PLLA and PCL blends compatibilized with a triblock copolymer. Materials Science and Engineering: A, 2010. 527(26): p. 6930-6937.
Li, W., et al., A facile method to produce graphene oxide-g-poly(L-lactic acid) as an promising reinforcement for PLLA nanocomposites. Chemical Engineering Journal, 2014. 237: p. 291-299.
Sheng, S.-J., et al., Mechanical and thermal property characterization of poly-l-lactide (PLLA) scaffold developed using pressure-controllable green foaming technology. Materials Science and Engineering: C, 2015. 49: p. 612-622.
Chieng, B.W., et al., Poly (lactic acid)/poly (ethylene glycol) polymer nanocomposites: effects of graphene nanoplatelets. Polymers, 2014. 6(1): p. 93-104.
Palama, I.E., et al., Micropatterned polyelectrolyte nanofilms promote alignment and myogenic differentiation of C2C12 cells in standard growth media. Biotechnology and bioengineering, 2013. 110(2): p. 586-596.
Uehara, T.M., et al., Fabrication of random and aligned electrospun nanofibers containing graphene oxide for skeletal muscle cells scaffold. Polymers for Advanced Technologies, 2020.
Wu, S., et al., Living nanofiber yarn-based woven biotextiles for tendon tissue engineering using cell tri-culture and mechanical stimulation. Acta biomaterialia, 2017. 62: p. 102-115.
Li, W.J., et al., Electrospun nanofibrous structure: a novel scaffold for tissue engineering. Journal of Biomedical Materials Research: An Official Journal of The Society for Biomaterials, The Japanese Society for Biomaterials, and The Australian Society for Biomaterials and the Korean Society for Biomaterials, 2002. 60(4): p. 613-621.
Saveh Shemshaki N, Kan HM, Barajaa M, Otsuka T, Lebaschi A, Mishra N, Nair LS, Laurencin CT. Muscle degeneration in chronic massive rotator cuff tears of the shoulder: Addressing the real problem using a graphene matrix. Proc Natl Acad Sci U S A. Aug. 16, 2022;119(33):e2208106119. doi: 10.1073/pnas.2208106119. Epub Aug. 8, 2022. PMID: 35939692; PMCID: PMC9388153.
Kausar, A.; Ahmad, I.; Zhao, T.; Aldaghri, O.; Ibnaouf, K.H .; Eisa, M.H. Nanocomposite Nanofibers of Graphene-Fundamentals and Systematic Developments. J. Compos. Sci. 2023, 7, 323.
Saveh-Shemshaki N, Barajaa MA, Otsuka T, Mirdamadi ES, Nair LS, Laurencin CT. Electroconductivity, a regenerative engineering approach to reverse rotator cuff muscle degeneration. Regen Biomater. Nov. 1, 20231;10: rbad099. doi: 10.1093/rb/rbad099. PMID: 38020235; PMCID: PMC10676522.
Shemshaki NS, Kan HM, Barajaa MA, Lebaschi A, Otsuka T, Mishra N, Nair LS, Laurencin CT. Efficacy of a Novel Electroconductive Matrix To Treat Muscle Atrophy and Fat Accumulation in Chronic Massive Rotator Cuff Tears of the Shoulder. ACS Biomater Sci Eng. Oct. 9, 2023;9(10):5782-5792. doi: 10. 1021/acsbiomaterials.3c00585. Epub Sep. 28, 2023. PMID: 37769114.

\* cited by examiner

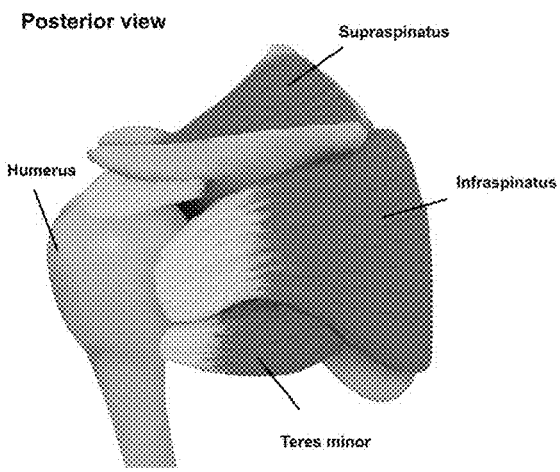
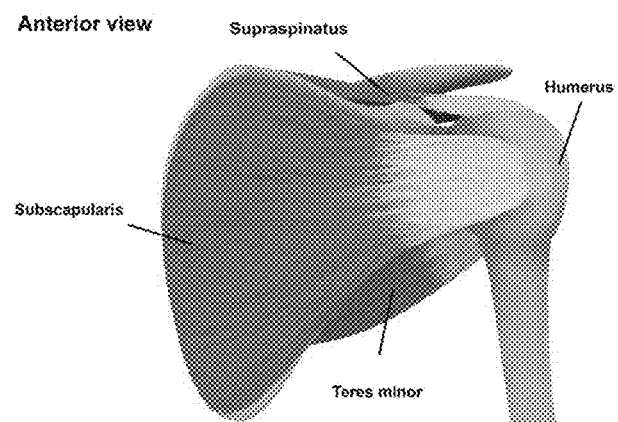
Fig. 1A
Fig. 1B
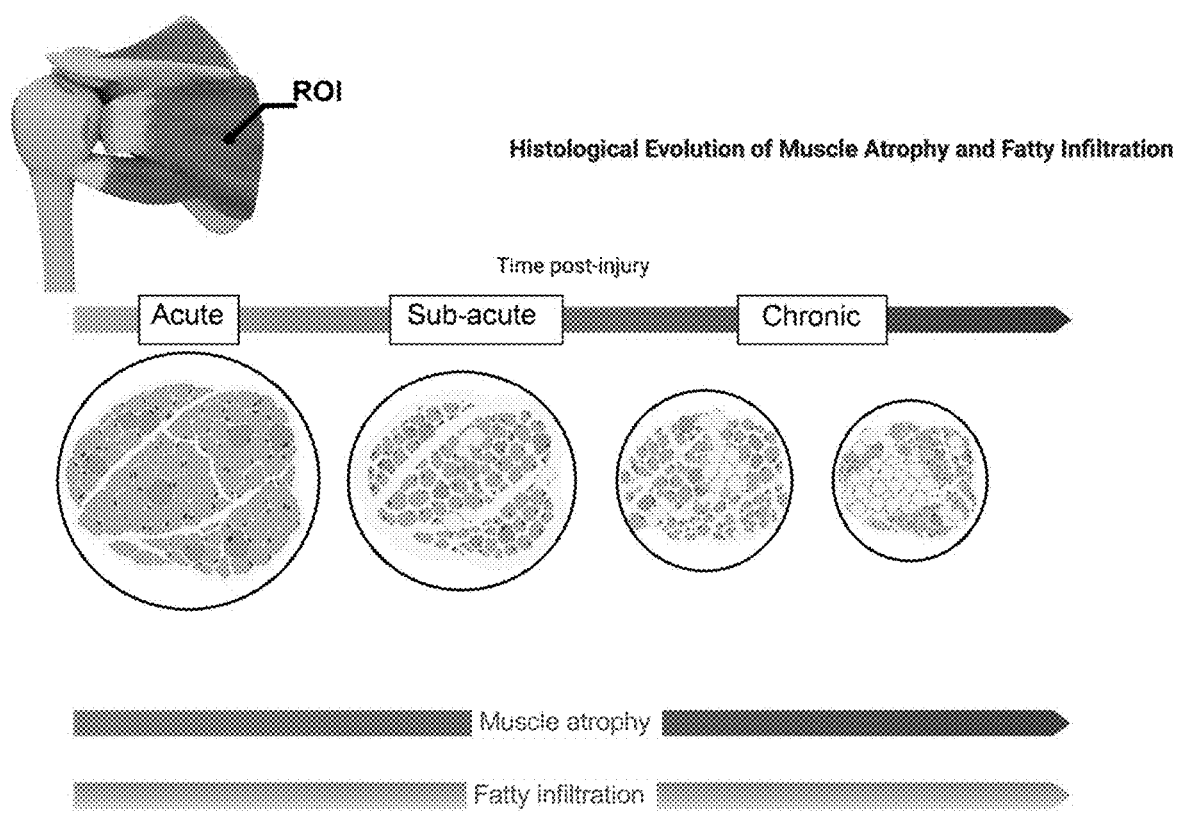
Fig. 2

GRAPHENE-BASED NANOFIBERS FOR SKELETAL MUSCLE TISSUE REGENERATION

RELATED APPLICATIONS

This application claims the benefit of U.S. Provisional Patent Application No. 63/041,594, filed Jun. 19, 2020, which is incorporated by reference herein in its entirety.

BACKGROUND

Skeletal muscle comprises 40-45% of the total human body mass and consists of bundles of aligned muscle fibers. The growth and maintenance of muscle are supported by muscle stem cells that participate in the myogenesis process by differentiating into myoblasts. While the regeneration potential of muscle cells provides an intrinsic repair mechanism for minor injuries and damage, this repair mechanism cannot regenerate severe diseases and massive injuries, such as skeletal myopathies and volumetric muscle loss. Since current strategies cannot achieve satisfactory results for the treatment of severe muscle injuries, there remains a pressing need to develop novel tissue regeneration strategies to address current challenges.

SUMMARY

Methods and apparatuses for skeletal muscle regeneration are generally disclosed herein.

In one aspect, aspect disclosed herein are scaffolds comprising nanofibers, wherein the nanofibers comprise a mixture of graphene nanoplatelets and a biocompatible polymer.

In some embodiments of the scaffold, the biocompatible polymer comprises collagen, gelatin, chitosan, hyaluronic acid (HA), silk fibroin, polylactide (PLA), polyurethane (PU), poly(ε-caprolactone) (PCL), poly(DL-lactide) (PDLLA), poly(ether ester) based on poly(ethylene oxide) (PEE based on PEO), polybutylene terephthalate (PBT), polyglycolide (PGA), poly(L-lactide-co-glycolide) (PLGA), poly(lactic acid-glycolic acid) (PLAGA), poly(ethylene-co-vinylacetate) (PEVA), poly(L-lactic acid (PLLA), or poly(L-lactide-co-ε-caprolactone) (PLLA-CL).

In some embodiments of the scaffold, the biocompatible polymer comprises poly(L-lactic acid (PLLA).

In some embodiments of the scaffold, the scaffold comprises about 75 wt % of biocompatible polymer to about 99.9 wt % of biocompatible polymer, about 80 wt % of biocompatible polymer to about 99.8 wt % of biocompatible polymer, about 85 wt % of biocompatible polymer to about 99.7 wt % of biocompatible polymer, about 90 wt % of biocompatible polymer to about 99.7 wt % of biocompatible polymer, about 91 wt % of biocompatible polymer to about 99.6 wt % of biocompatible polymer, about 92 wt % of biocompatible polymer to about 99.5 wt % of biocompatible polymer, about 94 wt % of biocompatible polymer to about 99.5 wt % of biocompatible polymer, about 95 wt % of biocompatible polymer to about 99.5 wt % of biocompatible polymer, about 96 wt % of biocompatible polymer to about 99.5 wt % of biocompatible polymer, about 97 wt % of biocompatible polymer to about 99.5 wt % of biocompatible polymer, about 98 wt % of biocompatible polymer to about 99.5 wt % of biocompatible polymer, or about 98.5 wt % of biocompatible polymer to about 99.5 wt % of biocompatible polymer.

In some embodiments of the scaffold, the scaffold consists of about 92 wt % of biocompatible polymer to about 99.5 wt % of biocompatible polymer.

In some embodiments of the scaffold, the scaffold consists of about 98 wt % of biocompatible polymer to about 99.5 wt % of biocompatible polymer.

In some embodiments of the scaffold, the scaffold comprises about 0.1 wt % of graphene nanoplatelets to about 25 wt % of graphene nanoplatelets, about 0.2 wt % of graphene nanoplatelets to about 20 wt % of graphene nanoplatelets, about 0.3 wt % of graphene nanoplatelets to about 15 wt % of graphene nanoplatelets, about 0.3 wt % of graphene nanoplatelets to about 10 wt % of graphene nanoplatelets, about 0.4 wt % of graphene nanoplatelets to about 9 wt % of graphene nanoplatelets, about 0.5 wt % of graphene nanoplatelets to about 8 wt % of graphene nanoplatelets, about 0.5 wt % of graphene nanoplatelets to about 6 wt % of graphene nanoplatelets, about 0.5 wt % of graphene nanoplatelets to about 5 wt % of graphene nanoplatelets, about 0.5 wt % of graphene nanoplatelets to about 4 wt % of graphene nanoplatelets, about 0.5 wt % of graphene nanoplatelets to about 3 wt % of graphene nanoplatelets, about 0.5 wt % of graphene nanoplatelets to about 2 wt % of graphene nanoplatelets, or about 0.5 wt % of graphene nanoplatelets to about 1.5 wt % of graphene nanoplatelets.

In some embodiments of the scaffold, the scaffold consists of about 0.5 wt % of graphene nanoplatelets to about 8 wt % of graphene nanoplatelets.

In some embodiments of the scaffold, the scaffold consists of about 0.5 wt % of graphene nanoplatelets to about 2 wt % of graphene nanoplatelets.

In some embodiments of the scaffold, the nanofibers comprise uniaxial nanofibers.

In some embodiments of the scaffold, the nanofibers comprise a random orientation.

In some embodiments of the scaffold, the nanofibers comprise an ordered orientation.

In some embodiments of the scaffold, the ordered orientation comprises a substantially parallel orientation.

In some embodiments of the scaffold, the nanofibers comprise an average diameter of about 400 nm to about 1200 nm, about 400 nm to about 1100 nm, about 400 nm to about 1000 nm, about 400 nm to about 900 nm, about 450 nm to about 850 nm, about 500 nm to about 800 nm, about 550 nm to about 750 nm, or about 600 nm and 700 nm.

In some embodiments of the scaffold, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise pristine graphene nanoplatelets.

In some embodiments of the scaffold, at least about 90%, at least about 95%, at least about 96%, at least about 97%, at least about 98%, at least about 99% of the graphene nanoplatelets comprise pristine graphene nanoplatelets.

In some embodiments of the scaffold, at least about 99% of the graphene nanoplatelets comprise pristine graphene nanoplatelets.

In some embodiments of the scaffold, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise functionalized graphene nanoplatelets.

In some embodiments of the scaffold, at least about 90%, at least about 95%, at least about 96%, at least about 97%, at least about 98%, or at least about 99% of the graphene nanoplatelets comprise functionalized graphene nanoplatelets.

In some embodiments of the scaffold, at least about 99% of the graphene nanoplatelets comprise functionalized graphene nanoplatelets.

In some embodiments of the scaffold, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise pristine graphene nanoplates and functionalized graphene nanoplatelets.

In some embodiments of the scaffold, at least about 90%, at least about 95%, at least about 96%, at least about 97%, at least about 98%, or at least about 99% of the graphene nanoplatelets comprise pristine graphene nanoplates and functionalized graphene nanoplatelets.

In some embodiments of the scaffold, at least about 99% of the graphene nanoplatelets comprise pristine graphene nanoplates and functionalized graphene nanoplatelets.

In some embodiments of the scaffold, the scaffold has a porosity of about 50% to about 99.9%, a porosity of about 55% to about 99%, a porosity of about 60% to about 95%, a porosity of about 65% to about 92.5%, a porosity of about 70% and about 90%, a porosity of about 75% and about 90%, a porosity of about 80% to about 90%, a porosity of about 82% to about 89%, or a porosity of about 83% to about 88%.

In another aspect, disclosed herein are methods for making the scaffold. In some embodiments, the method comprises the steps of: (a) mixing graphene nanoplatelets in an organic solvent to produce a mixture; (b) dissolving a biocompatible polymer in the mixture of (a) to produce a dissolved polymer mixture; (c) dispensing the dissolved polymer mixture through an aperture exposed to an electrical potential to produce nanofibers; and (d) collecting the nanofibers.

In some embodiments of the method for making the scaffold, the organic solvent is selected from 1,1,1,3,3,3-hexa-fluoro-2-propanol (HFIP), N-methylpyrrolidinone (NMP), dihydrolevoglucosenone (cyrene), dimethylsulfoxide (DMSO), and dimethylformamide (DMF).

In some embodiments of making the scaffold, the organic solvent is 1,1,1,3,3,3-hexa-fluoro-2-propanol (HFIP).

In some embodiments of the method for making the scaffold, the nanofibers are collected in a random orientation or an ordered orientation.

In some embodiments of the method for making the scaffold, the ordered orientation comprises nanofibers oriented in a substantially parallel orientation.

In some embodiments of the method for making the scaffold, the dispensing of the dissolved polymer mixture through an aperture exposed to an electrical potential is performed by an apparatus (e.g., an electrospinning machine).

In some embodiments of the method for making the scaffold, the biocompatible polymer comprises collagen, gelatin, chitosan, hyaluronic acid (HA), silk fibroin, polylactide (PLA), polyurethane (PU), poly(ε-caprolactone) (PCL), poly(DL-lactide) (PDLLA), poly(ether ester) based on poly(ethylene oxide) (PEE based on PEO), polybutylene terephthalate (PBT), polyglycolide (PGA), poly(L-lactide-co-glycolide) (PLGA), poly(lactic acid-glycolic acid) (PLAGA), poly(ethylene-co-vinylacetate) (PEVA), poly(L-lactic acid (PLLA), or poly(L-lactide-co-ε-caprolactone) (PLLA-CL).

In some embodiments of the method for making the scaffold, the biocompatible polymer comprises poly(L-lactic acid (PLLA).

In some embodiments of the method for making the scaffold, the scaffold comprises about 1 wt % of biocompatible polymer to about 50 wt % of biocompatible polymer, about 2 wt % of biocompatible polymer to about 40 wt % of biocompatible polymer, about 3 wt % of biocompatible polymer to about 30 wt % of biocompatible polymer, about 4 wt % of biocompatible polymer to about 25 wt % of biocompatible polymer, about 5 wt % of biocompatible polymer to about 20 wt % of biocompatible polymer, about 6 wt % of biocompatible polymer to about 15 wt % of biocompatible polymer, about 7.5 wt % of biocompatible polymer to about 12.5 wt %, about 8 wt % to about 12 wt % of biocompatible polymer, about 9 wt % to about 11 wt % of biocompatible polymer, or about 10% of biocompatible polymer prior to dispensing the dissolved polymer mixture through an aperture exposed to an electrical potential.

In some embodiments of the method for making the scaffold, the scaffold consists of about 92 wt % of biocompatible polymer to about 99.5 wt % of biocompatible polymer prior to dispensing the dissolved polymer mixture through an aperture exposed to an electrical potential.

In some embodiments of the method for making the scaffold, the scaffold consists of about 98 wt % of the biocompatible polymer to about 99.5 wt % of the biocompatible polymer prior to dispensing the dissolved polymer mixture through an aperture exposed to an electrical potential.

In some embodiments of the method for making the scaffold, the scaffold comprises about 0.1 wt % to about 25 wt % of graphene nanoplatelets, about 0.2 wt % to about 20 wt % of graphene nanoplatelets, about 0.3 wt % to about 15 wt % of graphene nanoplatelets, about 0.3 wt % of graphene nanoplatelets to about 10 wt % of graphene nanoplatelets, about 0.4 wt % of graphene nanoplatelets to about 9 wt % of graphene nanoplatelets, about 0.5 wt % of graphene nanoplatelets to about 8 wt % of graphene nanoplatelets, about 0.5 wt % of graphene nanoplatelets to about 6 wt % of graphene nanoplatelets, about 0.5 wt % of graphene nanoplatelets to about 5 wt % of graphene nanoplatelets, about 0.5 wt % of graphene nanoplatelets to about 4 wt % of graphene nanoplatelets, about 0.5 wt % of graphene nanoplatelets to about 3 wt % of graphene nanoplatelets, about 0.5% of graphene nanoplatelets to about 2 wt % of graphene nanoplatelets, about 0.5 wt % of graphene nanoplatelets to about 1.5 wt % of graphene nanoplatelets.

In some embodiments of the method for making the scaffold, the scaffold consists of about 0.5 wt % of graphene nanoplatelets to about 8 wt % of graphene nanoplatelets.

In some embodiments of the method for making the scaffold, the scaffold consists of about 0.5 wt % of graphene nanoplatelets to about 2 wt % of graphene nanoplatelets.

In some embodiments of the method for making the scaffold, the graphene nanoplatelets comprise pristine graphene nanoplatelets.

In some embodiments of the method for making the scaffold, the graphene nanoplatelets comprise functionalized graphene nanoplatelets.

In some embodiments of the method for making the scaffold, the nanofibers produced by dispensing the dissolved polymer mixture through an aperture exposed to an electrical potential comprise uniaxial nanofibers.

In another aspect, disclosed herein are methods for repairing a muscle or tendon tear, comprising implanting the scaffolds disclosed herein, wherein one end of the scaffold is attached to a proximal end of a torn muscle or tendon and another end of the scaffold is attached to a distal end of a torn muscle or tendon.

In some embodiments of the method for repairing a muscle or tendon tear, the tendon tear is a rotator cuff tendon tear.

In some embodiments of the method for repairing a muscle or tendon tear, the rotator cuff tendon tear comprises a full-thickness rotator cuff tendon tear.

In some embodiments of the method for repairing a muscle or tendon tear, the rotator cuff tear is a chronic rotator cuff repair.

In some embodiments of the method for repairing a muscle or tendon tear, the tendon tear is selected from an Achilles tendon tear, a patellar tendon tear, a forearm extensor tear, and a tibialis posterior tear.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the invention. No attempt is made to show structural details of the invention in more detail than may be necessary for a fundamental understanding of the invention and various ways in which it may be practiced.

FIG. 1A and FIG. 1B show rotator cuff anatomy and the involved tendons including the supraspinatus, infraspinatus, teres minor, and the subscapularis providing a posterior view (FIG. 1A) and an anterior view (FIG. 1B).

FIG. 2 shows muscle atrophy and fatty infiltration of rotator cuff muscles in a sub-acute and chronic injury.

FIG. 8A and FIG. 8B show live/dead fluorescent images of cell-seeded scaffolds after 2 hours, 1 day, 3 days, 7 days and 14 days for scaffolds of 0, 0.5, 1.0 and 1.5% GnP content (FIG. 8A) and 2, 4, 6 and 8% GnP content (FIG. 8B), followed by quantitation (FIG. 8C).

FIG. 9A for immunofluorescent images of myotubes differentiated for seven days; FIG. 9B through FIG. 9D for quantitation) or differentiation media (DM; FIG. 9E for immunofluorescent images of myotubes differentiated for seven days; FIG. 9F through FIG. 9H for quantitation).

FIG. 12A shows a schematic illustration of myogenic regulatory factors, FIG. 12B and FIG. 12C show immunofluorescent images of MyoD and MyoG after 3 days on growth media (GM; FIG. 12B), 3 days on differentiation media (DM; FIG. 12C) and 5 days on growth media (GM; FIG. 12D), and 5 days on differentiation media (DM; FIG. 12E).

FIG. 13A shows immunofluorescent images of myotubes differentiated for 7 days on aligned scaffolds grown on GM, followed by quantification of myotube length (FIG. 13B), fusion index (FIG. 13C) and maturation index (FIG. 13D). FIG. 13E shows immunofluorescent images of myotubes differentiated for 7 days on aligned scaffolds grown on DM, followed by quantification of myotube length (FIG. 13F), fusion index (FIG. 13G) and maturation index (FIG. 13H).

FIG. 14A shows quantification of myotube length, followed by fusion index (FIG. 14B) and maturation index (FIG. 14C).

DETAILED DESCRIPTION

Figure 3A:
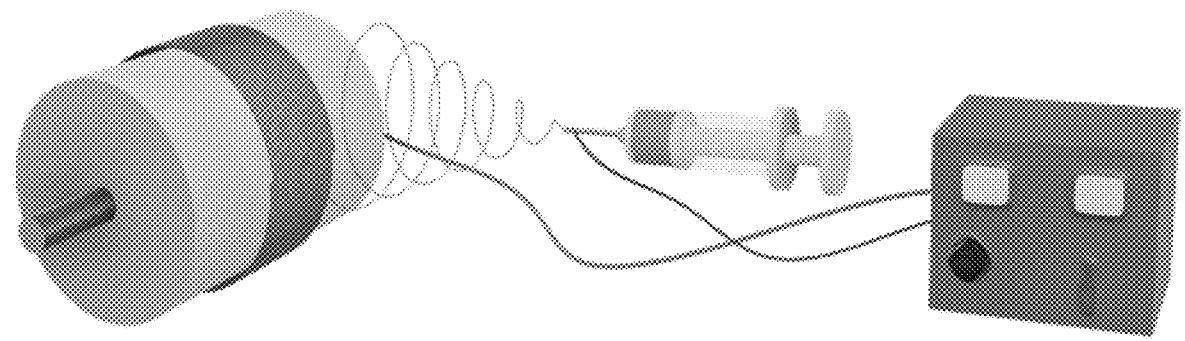
FIG. 3A and FIG. 3B show a schematic of electrospinning setups for fabrication of aligned nanofibers (FIG. 3A) and random nanofibers (FIG. 3B). The supply voltage provides the electric field between the collector and the nozzle. The polymeric solution is subject to an electric field, and the nanofibrous mats are retrieved on a collector.

A number of terms are defined below. As used herein, the singular forms "a," "an", and "the" include plural referents unless the context clearly dictates otherwise.

Unless otherwise apparent from the context, the term "about" encompasses insubstantial variations, such as values within a standard margin of error of measurement (e.g., SEM) of a stated value. For example, the term "about" as used herein when referring to a measurable value such as a parameter, an amount, a temporal duration, can encompass variations of +/−10% or less, +/−5% or less, or +/−1% or less or less of and from the specified value. Designation of a range of values includes all integers within or defining the range, and all subranges defined by integers within the range. As used herein, statistical significance means p≤0.05.

Unless the context clearly requires otherwise, throughout the description and the claims, the words "comprise", "comprising", "including" and the like are to be construed in an inclusive sense as opposed to an exclusive or exhaustive sense; that is to say, in the sense of "including, but not limited to". The words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All embodiments of any aspect of the disclosure can be used in combination unless the context clearly dictates otherwise.

Generally, disclosed herein are nanofiber-based scaffolds as well as methods of making and using such nanofiber scaffolds.

Scaffolds of the Invention and Methods of Making Thereof

Provided herein are scaffolds including nanofibers, which nanofibers include a mixture of graphene nanoplatelets and one or more biocompatible polymers. In some embodiments, the biocompatible polymer includes one or more of collagen, gelatin, chitosan, hyaluronic acid (HA), silk fibroin, polylactide (PLA), polyurethane (PU), poly(ε-caprolactone) (PCL), poly(DL-lactide) (PDLLA), poly(ether ester) based on poly(ethylene oxide) (PEE based on PEO), polybutylene terephthalate (PBT), polyglycolide (PGA), poly(l-lactide-co-glycolide) (PLGA), poly(lactic acid-glycolic acid) (PLAGA), poly(ethylene-co-vinylacetate) (PEVA), poly(l-lactic acid (PLLA), and poly(l-lactide-co-ε-caprolactone) (PLLA-CL). In some embodiments, the biocompatible polymer includes poly(l-lactic acid (PLLA), and in some embodiments, the biocompatible polymer is poly(l-lactic acid (PLLA).

Scaffolds disclosed herein can include varying amounts of biocompatible polymer and graphene nanoplatelets. The amount of biocompatible polymer and/or graphene nanoplatelets in the disclosed scaffolds can be expressed in terms of weight percent (% wt) of the scaffold. As used herein the term "weight percent" or "% wt" means the percentage by weight of the specified component (e.g., biocompatible polymer, graphene nanoplatelets) based upon the total weight of the composition (e.g., the disclosed scaffold).

In some embodiments, the disclosed scaffold comprises about 75 wt % of biocompatible polymer to about 99.9 wt % of biocompatible polymer, about 80 wt % of biocompatible polymer to about 99.8 wt % of biocompatible polymer, about 85 wt % of biocompatible polymer to about 99.7 wt % of biocompatible polymer, about 90 wt % of biocompatible polymer to about 99.7% of biocompatible polymer, about 91 wt % of biocompatible polymer to about 99.6 wt % of biocompatible polymer, about 92 wt % of biocompatible polymer to about 99.5 wt % of biocompatible polymer, about 94 wt % of biocompatible polymer to about 99.5 wt % of biocompatible polymer, about 95 wt % of biocompatible polymer to about 99.5 wt % of biocompatible polymer, about 96 wt % of biocompatible polymer to about 99.5 wt % of biocompatible polymer, about 97 wt % of biocompatible polymer to about 99.5 wt % of biocompatible polymer, about 98 wt % of biocompatible polymer to about 99.5 wt % of biocompatible polymer, or about 98.5 wt % of biocompatible polymer to about 99.5 wt % of biocompatible polymer. In some embodiments, the biocompatible polymer is present at about 92 wt % to about 99.5 wt % in the disclosed scaffold. In some embodiments, the biocompatible polymer is present at about 98 wt % to about 99.5 wt % in the disclosed scaffold.

As described elsewhere herein, graphene nanoplatelet abundance can affect numerous physical properties of the scaffold, including conductivity, elasticity (e.g., elongation at break), Young's modulus, and ultimate strength. Graphene nanoplatelet abundance can also affect cells (e.g., myoblasts, myocytes) that interact with the scaffolds of the disclosure, such as maturation index, fusion index and myotube length. In some embodiments, the scaffolds disclosed herein comprises about 0.1 wt % of graphene nanoplatelets to about 25 wt % of graphene nanoplatelets, about 0.2 wt % of graphene nanoplatelets to about 20 wt % of graphene nanoplatelets, about 0.3 wt % of graphene nanoplatelets to about 15 wt % of graphene nanoplatelets, about 0.3 wt % to about 10 wt %, about 0.4 wt % of graphene nanoplatelets to about 9 wt % of graphene nanoplatelets, about 0.5 wt % of graphene nanoplatelets to about 8 wt % of graphene nanoplatelets, about 0.5 wt % of graphene nanoplatelets to about 6 wt % of graphene nanoplatelets, about 0.5 wt % of graphene nanoplatelets to about 5 wt % of graphene nanoplatelets, about 0.5 wt % of graphene nanoplatelets to about 4 wt % of graphene nanoplatelets, about 0.5 wt % of graphene nanoplatelets to about 3 wt % of graphene nanoplatelets, about 0.5 wt % of graphene nanoplatelets to about 2 wt % of graphene nanoplatelets, or about 0.5 wt % of graphene nanoplatelets to about 1.5 wt % of graphene nanoplatelets. In some embodiments, the scaffolds disclosed herein comprise about 0.5 wt % of graphene nanoplatelets to about 8 wt % of graphene nanoplatelets. In some embodiments, the scaffolds disclosed herein consist of about 0.5 wt % of graphene nanoplatelets to about 2 wt % of graphene nanoplatelets.

The orientation of the scaffold nanofibers can influence, e.g., myoblast growth, differentiation, and migration. Thus, in some embodiments the scaffolds disclosed herein include uniaxial nanofibers, randomly oriented nanofibers, ordered nanofibers, substantially parallel nanofibers, and combinations thereof. For instance, a scaffold can include regions of differently or distinctly oriented fibers to promote cellular responses characteristic of each type of fiber orientation on those distinct areas of the scaffold. Substantially parallel fibers in the middle of a scaffold may promote rapid growth, migration, and differentiation of myoblasts in that region of the scaffold, while nanofibers of a different orientation (e.g., random) on either side of the scaffold may promote different but desirable cellular characteristics in those regions that complement the cells in the central, parallel nanofiber region.

In some embodiments, the nanofibers comprise an average diameter of about 400 nm to about 1200 nm, about 400 nm to about 1100 nm, about 400 nm to about 1000 nm, about 400 nm to about 900 nm, about 450 nm to about 850 nm, about 500 nm to 800 nm, about 550 nm to about 750 nm, or about 600 nm to about 700 nm.

In some embodiments, the biocompatible polymer comprises one or more of collagen, gelatin, chitosan, hyaluronic acid (HA), silk fibroin, polylactide (PLA), polyurethane (PU), poly(ε-caprolactone) (PCL), poly(DL-lactide) (PDLLA), poly(ether ester) based on poly(ethylene oxide) (PEE based on PEO), polybutylene terephthalate (PBT), polyglycolide (PGA), poly(L-lactide-co-glycolide) (PLGA), poly(lactic acid-glycolic acid) (PLAGA), poly(ethylene-co-vinylacetate) (PEVA), poly(L-lactic acid (PLLA), or poly(L-lactide-co-ε-caprolactone) (PLLA-CL). In some embodiments, the biocompatible polymer comprises poly(L-lactic acid (PLLA). In some embodiments, the biocompatible polymer is poly(L-lactic acid (PLLA).

Also disclosed herein are methods for making the scaffolds as described herein. In some embodiments, the disclosed methods include the steps of (a) mixing graphene nanoplatelets in one or more solvents to produce a mixture; (b) dissolving a biocompatible polymer in the mixture of (a) to produce a dissolved polymer mixture; (c) dispensing the dissolved polymer mixture through an aperture exposed to an electrical potential to produce nanofibers; and/or (d) collecting the nanofibers.

In some embodiments, the solvent is an organic solvent. Exemplary organic solvents include, but are not limited to, 1,1,1,3,3,3-hexa-fluoro-2-propanol (HFIP), N-methylpyrrolidinone (NMP), dihydrolevoglucosenone (cyrene), dimethylsulfoxide (DMSO), and dimethylformamide (DMF). In some embodiments, the organic solvent is HFIP.

In some embodiments, the nanofibers can be collected in a random orientation or an ordered orientation. Ordered nanofiber orientation includes, e.g., substantially parallel, substantially uniaxial, or substantially biaxial (e.g., perpendicular or crossing at a non-normal angle). Dispensing of the dissolved polymer mixture through an aperture exposed to an electrical potential can be done by hand or by an apparatus. In some embodiments, dispensing of the dissolved polymer through the aperture exposed to the electrical potential is done by an apparatus. In certain embodiments, the apparatus comprises an electrospinning machine.

The finished scaffolds can include varying amounts of biocompatible polymer and graphene nanoplatelets as was discussed above and herein.

Further, prior to dispensing the dissolved polymer mixture through an aperture exposed to an electrical potential (i.e., solvent is present) the biocompatible polymer is also present. For example, in some embodiments, prior to dispensing the dissolved polymer mixture through an aperture exposed to an electrical potential, the scaffold comprises about 1 wt % of biocompatible polymer to about 50 wt % of biocompatible polymer, about 2 wt % of biocompatible polymer to about 40 wt % of biocompatible polymer, about 3 wt % of biocompatible polymer to about 30 wt % of biocompatible polymer, about 4 wt % of biocompatible polymer to about 25 wt % of biocompatible polymer, about 5 wt % of biocompatible polymer to about 20 wt % of biocompatible polymer, about 6 wt % of biocompatible polymer to about 15 wt % of biocompatible polymer, about 7.5 wt % of biocompatible polymer to about 12.5 wt % of biocompatible polymer, about 8 wt % of biocompatible polymer to about 12 wt % of biocompatible polymer, about 9 wt % of biocompatible polymer to about 11 wt % of biocompatible polymer, or about 10 wt % of biocompatible polymer.

In some embodiments, the biocompatible polymer is present at about 92 wt % to about 99.5 wt % of the scaffold after nanofiber dispensing, collection, and drying. In some embodiments, the biocompatible polymer is present at about 98 wt % to about 99.5 wt % of the scaffold after nanofiber dispensing, collection, and drying.

In some embodiments, the scaffolds disclosed herein comprise about 0.1 wt % of graphene nanoplatelets to about 25 wt % of graphene nanoplatelets, about 0.2 wt % of graphene nanoplatelets to about 20 wt % of graphene nanoplatelets, about 0.3 wt % of graphene nanoplatelets to about 15 wt % of graphene nanoplatelets, about 0.3 wt % of graphene nanoplatelets to about 10 wt % of graphene nanoplatelets, about 0.4 wt % of graphene nanoplatelets to about 9 wt % of graphene nanoplatelets, about 0.5 wt % of graphene nanoplatelets to about 8 wt % of graphene nanoplatelets, about 0.5 wt % of graphene nanoplatelets to about 6 wt % of graphene nanoplatelets, about 0.5 wt % of graphene nanoplatelets to about 5 wt % of graphene nanoplatelets, about 0.5 wt % of graphene nanoplatelets to about 4 wt % of graphene nanoplatelets, about 0.5 wt % of graphene nanoplatelets to about 3 wt % of graphene nanoplatelets, about 0.5 wt % of graphene nanoplatelets to about 2 wt % of graphene nanoplatelets, or about 0.5 wt % of graphene nanoplatelets to about 1.5 wt % of graphene nanoplatelets as a wt % of the scaffold. In some embodiments, the scaffolds disclosed herein comprise about 0.5 wt % of graphene nanoplatelets to about 8 wt % of graphene nanoplatelets. In some embodiments, the scaffolds disclosed herein comprise about 0.5 wt % of graphene nanoplatelets to about 2 wt % of graphene nanoplates.

Graphene has a molecular structure comprising a single layer of carbon atoms bonded in a hexagonal lattice structure. Graphene nanoplatelets (named for their platelet-like shape) are stacks of graphene sheets in a two-dimensional nano-particulate format. Graphene nanoplatelets ("GnPs") can be dispersed into other materials to enhance their properties. GnPs vary in number of atomic layers but typically comprise between about 1-15 nm thickness or about 3-10 nm thickness; and sub-micron to 100 μm diameter or about 1-15 μm diameter. GnPs have edges that are readily chemically modified for enhanced dispersion in polymers. Chemical modifications can include, for example, $-NH_2$, $-COOH$, $-N_2$ functionalization, and the like. Pristine graphene refers to graphene in its unoxidized form.

In some embodiments, the GnPs comprise pristine graphene nanoplatelets. In other embodiments, the graphene nanoplatelets comprise functionalized graphene nanoplatelets. Some embodiments include both functionalized graphene nanoplatelets and non-functionalized or pristine graphene nanoplatelets.

In some embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise pristine graphene nanoplatelets.

In some embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise functionalized nanoplatelets In some embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise a combination of pristine graphene nanoplatelets and functionalized nanoplatelets.

In some embodiments, at least about 90%, at least about 95%, at least about 96%, at least about 97%, at least about 98%, at least about 99% of the graphene nanoplatelets comprise pristine graphene nanoplatelets.

In some embodiments, at least about 90%, at least about 95%, at least about 96%, at least about 97%, at least about 98%, at least about 99% of the graphene nanoplatelets comprise functionalized graphene nanoplatelets.

In some embodiments, at least about 90%, at least about 95%, at least about 96%, at least about 97%, at least about 98%, at least about 99% of the graphene nanoplatelets comprise a combination of pristine graphene nanoplatelets and functionalized graphene nanoplatelets.

In some embodiments, at least about 99% of the graphene nanoplatelets comprise pristine graphene nanoplatelets.

In some embodiments, at least about 99% of the graphene nanoplatelets comprise functionalized nanoplatelets.

In some embodiments, at least about 99% of the graphene nanoplatelets comprise a combination of pristine graphene nanoplatelets and functionalized graphene nanoplatelets.

Scaffolds can be made to various degrees of porosity. Porosity can affect cellular interaction with the scaffold. In some embodiments, the scaffold comprises a porosity of about 50% to about 99.9%, a porosity of about 55% to about 99%, a porosity of about 60% to about 95%, a porosity of about 65% to about 92.5%, a porosity of about 70% to about 90%, a porosity of about 75% to about 90%, of about 80% to about 90%, a porosity of about 82% to about 89%, or a porosity of about 83% to about 88%.

Methods of Treatment
Muscle and Tendon Tears

Also disclosed herein are methods for repairing or treating a muscle or tendon tear, comprising implanting a scaffold of the disclosure in a subject (e.g., a human or a non-human animal) in need thereof. In some embodiments, the method comprises attaching one end of the scaffold to a proximal end of a torn muscle or tendon and the opposite end of the scaffold is attached to a distal end of a torn muscle or tendon. Any muscle or tendon may be eligible for repair with a scaffold of the disclosure, and in some embodiments, the tendon tear is a rotator cuff tendon tear, which, in some embodiments, comprises a full-thickness rotator cuff tendon tear. In some embodiments, the tendon tear is a chronic rotator cuff tear. In some embodiments, the tendon tear is an Achilles tendon tear.

In some embodiments, disclosed herein are methods for repairing or treating a muscle or tendon tear. Such methods include implanting a scaffold of the disclosure, wherein one end of the scaffold is attached to a proximal end of a torn muscle or tendon and the opposite end of the scaffold is attached to a distal end of a torn muscle or tendon. In some embodiments, the tendon tear is a rotator cuff tendon tear. In some embodiments, the repair is a a chronic rotator cuff repair. In some embodiments, the tendon tear is selected from an Achilles tendon tear, a patellar tendon tear, a forearm extensor tear, a tibialis posterior tear, and other tendon tear (e.g., a shoulder tear, a rotator cuff tear, a bicep tendon tear, a labral tear, and the like).

Muscle Regeneration

Skeletal muscle is an electrically excitable tissue. Applying or incorporating guidance cues in a biocompatible scaffold can improve interactions between the scaffold and cells and facilitate myoblast communication, growth, and development.

Disclosed herein is a biomimetic scaffold structure that comprises an electroactive biomaterial comprising pristine graphene nanoplatelets and aligned nanofibrous structures that can simultaneously serve as two guidance cues for muscle regeneration. Aligned nanofibrous scaffolds can mimic the bundle of aligned fibers and multinucleated myotubes in skeletal muscle tissue, and the incorporation of electroactive materials into this biomimetic structure facilitates electrical signal propagation.

In some embodiments, aligned and randomly oriented nanofibers comprising pristine graphene nanoplatelets (as opposed to non-pristine graphenes such as graphene oxide or reduced graphene oxide with a variety of natural and synthetic materials) and poly (L-lactic acid) (PLLA) were fabricated into a substrate (or "scaffold") to promote successful regeneration of skeletal muscle both in vitro and in vivo.

In some embodiments, the addition of pristine graphene nanoplatelets into PLLA nanofibers provides electrical conductivity and mechanical strength for both aligned and random orientations, as compared with a pure PLLA scaffold. In some embodiments, the topographical and electrical cues provided by the scaffolds described herein affect muscle cell proliferation and differentiation as demonstrated in mouse C2C12 myoblasts cultured on the scaffolds without external electrical stimulation. In some embodiments, the topographical and electrical cues provided by the scaffolds affect muscle cell proliferation and differentiation synergistically.

In some embodiments, the alignment of the nanofibers in a scaffold significantly guided myoblast orientation and myotube elongation, and in some embodiments, the incorporation of pristine graphene nanoplatelets into highly aligned PLLA nanofibers significantly increases myotube length, fusion and, maturation indices in both standard growth media and differentiative media. In some embodiments, the alignment of nanofibers was the most influential factor for myotubes elongation, and pristine graphene nanoplatelets significantly promotes fusion and maturation of the myotubes.

In some embodiments, the scaffold can be used for a novel treatment strategy for repair of chronic full-thickness rotator cuff tears as shown in a rat chronic full-thickness rotator cuff tear model. In some embodiments, the graphene scaffold can reduce fatty infiltration and reverse muscle atrophy in a chronic rotator cuff tear model. In some embodiments, highly aligned, pristine graphene-based nanofibers are disclosed for use in skeletal muscle regeneration.

Utility of Muscle Regeneration for Shoulder Injury

Shoulder stability and movement are controlled by a group of muscles whose tendons are collectively called the rotator cuff (RC). RC tendons consist of the supraspinatus, infraspinatus, teres minor, and subscapularis and connect the muscles surrounding the scapula to the humerus through tendon-bone insertions. These tendons as a group support the rotation and stability of the humerus (FIG. 1).

RC repair is one of the most frequent orthopedic procedures, especially among athletes, workers, and the adult population in general, with more than 200,000 repair procedures performed per year in the United States. RCTs are classified based on the tear shape, size, and the number of torn tendons as 1) partial or incomplete tears, which involve only part of the tendon thickness, and 2) full-thickness tears which involve the entire thickness of one or more tendons. The delay between the time of RC injury and surgical repair is one of the most observed challenges. The duration between repair is described by category, specifically "acute," "sub-acute," and "chronic". An acute RC injury involves the immediate repair of the injury while sub-acute and chronic refer to a prolonged duration between the time of injury and repair. Sub-acute and chronic RCTs are often associated with a set of pathological changes that include muscle atrophy, fatty infiltration, and fibrosis (FIG. 2). In the initial days post-injury, the migration of inflammatory cells leads to the apoptosis of muscle fibers.

These challenges result in a high retear rate after surgery, particularly for full thickness tears, and as a result significant research has focused on RC repair, including various suture techniques (e.g., single row and double row), the use of tissue transplants (e.g., allograft, xenograft, autograft, decellularized structures), and tissue regeneration strategies. Clinically, current surgical strategies, including suture techniques and tissue transplants, have failed to regenerate RCTs satisfactorily. As both surgical and non-surgical strategies have failed to achieve satisfactory results to treat full-thickness RCTs, novel tissue regeneration strategies are provided herein to address current challenges.

Skeletal Muscle Regenerative Engineering

The growth and maintenance of muscle are supported by muscle stem cells that undergo myogenesis by differentiating into myoblasts. While this regeneration potential provides an intrinsic repair mechanism for minor muscle injuries and damage, this repair mechanism cannot physically support muscle to prevent fatty infiltration and atrophy after RCTs. Indeed, severe damage to muscle tissues prevents muscle stem cell recruitment and activation, thus limiting regeneration. However, the activation of fibroblasts results in collagen deposition and subsequently fibrosis and scar tissue formation, which generally leads to patient suffering and reduced functionality.

The current standard treatment for muscle regeneration is to engraft healthy autologous tissue from an uninjured site. Despite the success of autograft transplantation, around 10% of these procedures fail due to infection and necrosis. Moreover, autografts suffer limitations such as donor morbidity and limited availability.

Electroconductive Materials

An important step in tissue regeneration is constructing an effective biomimetic scaffold, which supports cell growth and provides appropriate synergistic regulation cues. The electroconductive materials disclosed herein include carbon-based composites and conductive polymers. Such electroconductive materials display the physical and chemical properties of polymers and the electrical characteristics of metals and, as shown herein, can provide a cue to promote muscle regeneration by improving the interactions between materials and cells.

The following are provided for exemplification purposes only and are not intended to limit the scope of the invention described in broad terms above. All references cited in this disclosure are incorporated herein by reference.

EXAMPLES

Example 1: Fabrication of Electrospun Scaffolds

Figure 3B:
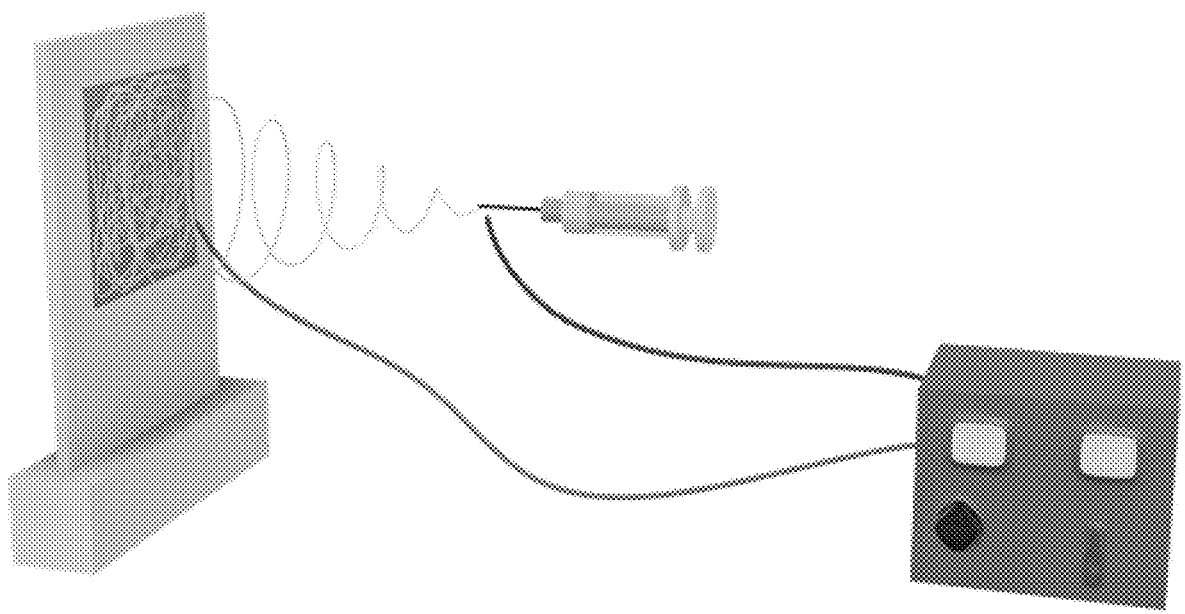
Figure 4:
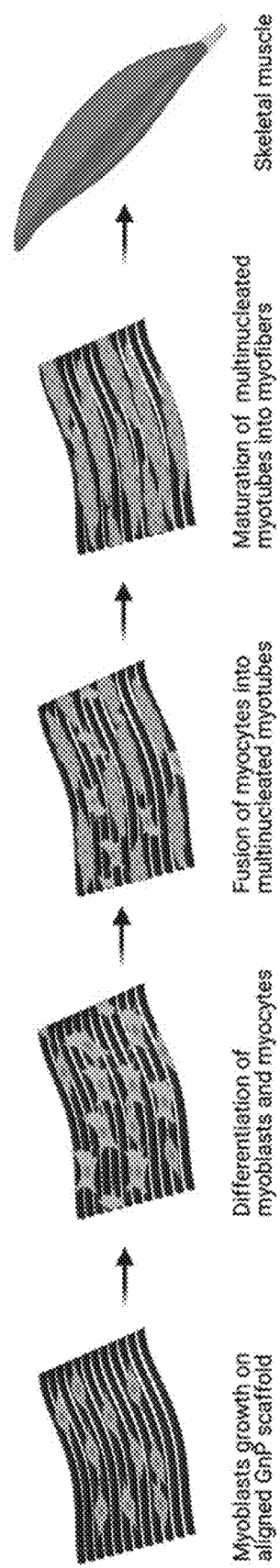
FIG. 4 shows myoblast growth and differentiation on aligned nanofibers.

Electrospinning was used to fabricate a layer of nanofibers with a small pore size and high surface area. In this method, a flow of polymeric solution is drawn from the nozzle to form a droplet at the tip of the nozzle by a combination of forces include electrostatic charge, mechanical pumping, and gravity (FIG. 3). By applying a sufficiently high voltage, the surface tension of the droplet cannot overcome the electrostatic charge, and a polymer jet forms. Evaporation of the solvent during the flight increases the surface charge density, which causes elongation of the erupted jet and the formation of nanofibers.

The electrospin solutions were prepared by adding different amount of GnPs include 0.5 mg/ml, 1 mg/ml, 1.5 mg/ml, 2 mg/ml, 4 mg/ml, 6 mg/ml, and 8 mg/ml in 5 ml hexafluoroisopropanol (HFIP) and stirring for six hours at room temperature. PLLA (500 mg) was then added to the GnP/HFIP suspension, followed by stirring overnight at room temperature to obtain a homogenous composite suspension. For pure PLLA scaffolds, 500 mg of PLLA was directly added to 5 ml HFIP and stirred overnight. Electrospinning of uniaxial nanofibers was performed in a horizontal electrospinning setup. The prepared solution was loaded into a plastic syringe with a 20G stainless steel needle from Nordson EFD (OH, USA). For randomly oriented nanofibers, an Aluminum plate was used as the collector during the electrospinning process with a 0.75 mL/hr flow rate, 17 Kv potential, and 20 cm as the distance between the needle and the collector. A rotating mandrel was optimized at 2400 rpm as the collector during electrospinning to fabricate highly aligned nanofibers. Following the electrospinning, the fabricated mats were dried overnight under vacuum and used for characterization and in vitro studies.

Materials:

Poly (L-lactide) (PLLA, inherent viscosity 2.0-2.7 dl/g) was purchased from Corbion Purac (KS, USA). Non-functionalized GnPs were obtained from Cheap Tubes Inc (VT, USA). 1,1,1,3,3,3-Hexa-fluoro-2-propanol (HFIP) was obtained from Sigma-Aldrich (MO, USA). All chemicals were used without further purifications.

Example 2: Characterization of Scaffolds

Scanning electron microscopy (SEM): The micromorphology of the nanofibers was assessed via scanning electron microscopy (SEM, JEOL, USA) to find the optimized electrospinning parameters based on the SEM images. The fibrous mats were mounted onto the SEM sample studs and coated with gold using a sputter for 3 minutes. The diameters of the electrospun nanofibers were measured by Image J software (National Institutes of Health, USA). The average and standard deviation of the nanofiber diameters were calculated from 50 random measurements per image.

Figure 6A:
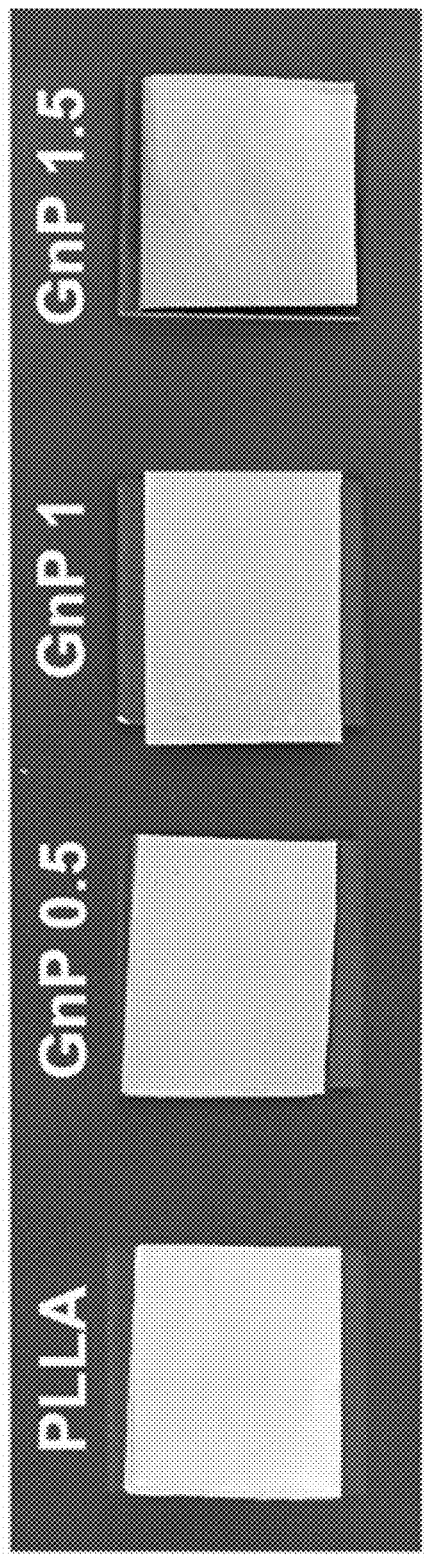
FIG. 6A through FIG. 6E show visualization (for example, photographs (FIG. 6A); scanning electron microscopy (SEM) images (FIG. 6B, FIG. 6C)) and characterization (average fiber diameter (FIG. 6D); percent porosity (FIG. 6E)) of various ratios of randomly oriented graphene nanofibers and graphene nanoplatelets (GnPs).
Figure 6A:
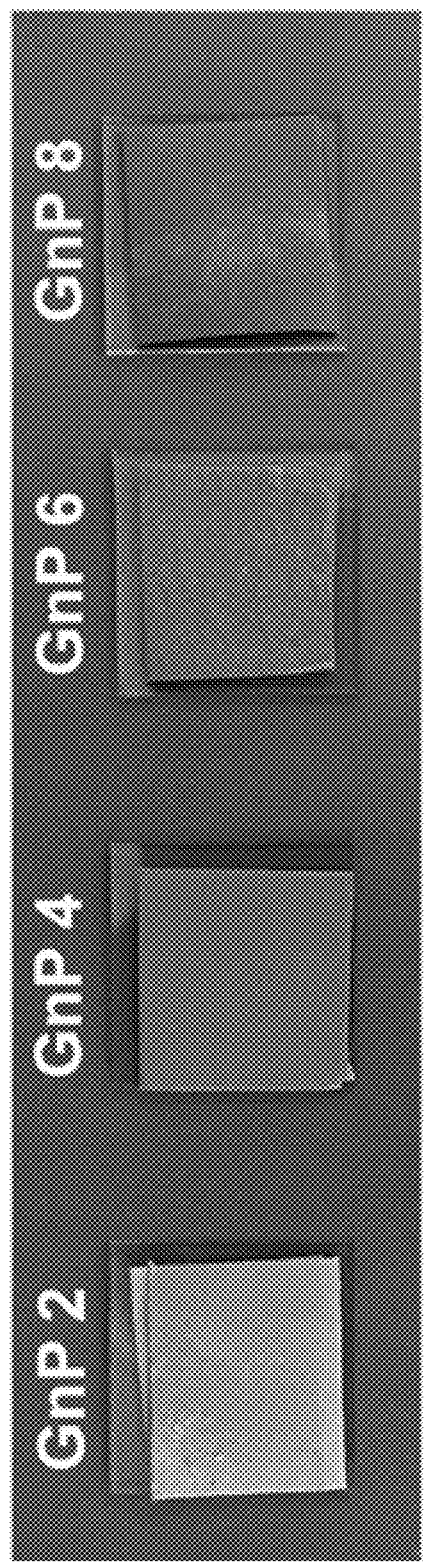
Figure 6B:
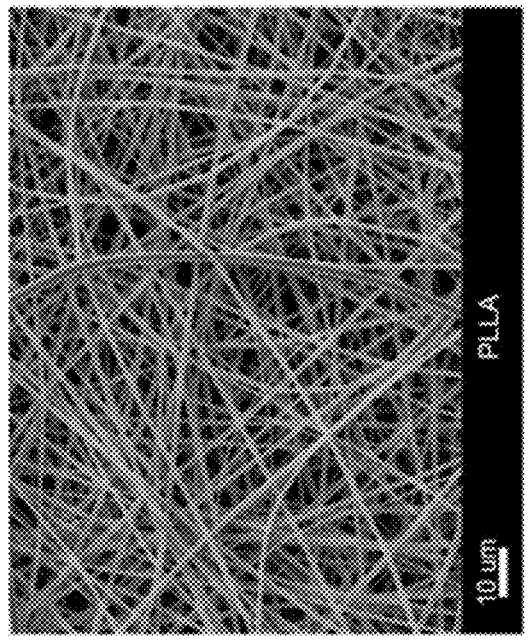
Figure 6B:
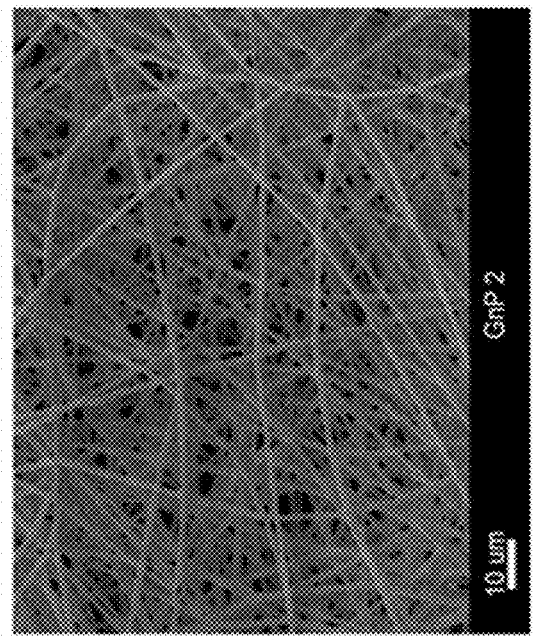
Figure 6B:
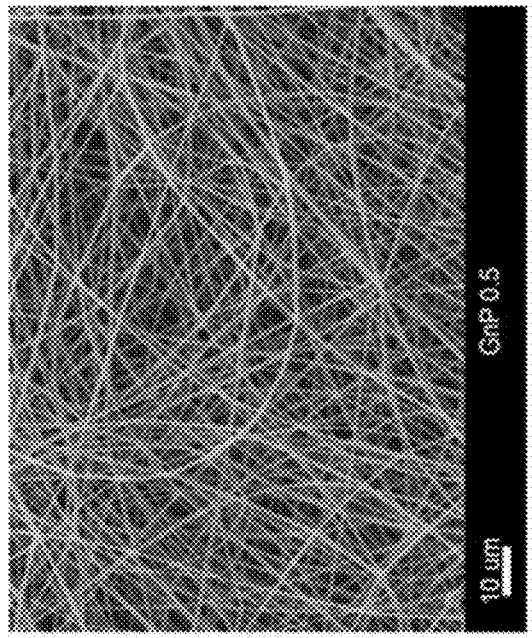
Figure 6B:
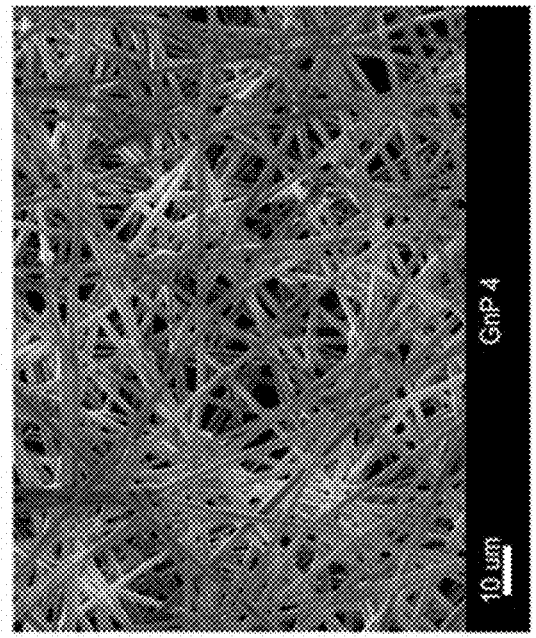
Figure 6C:
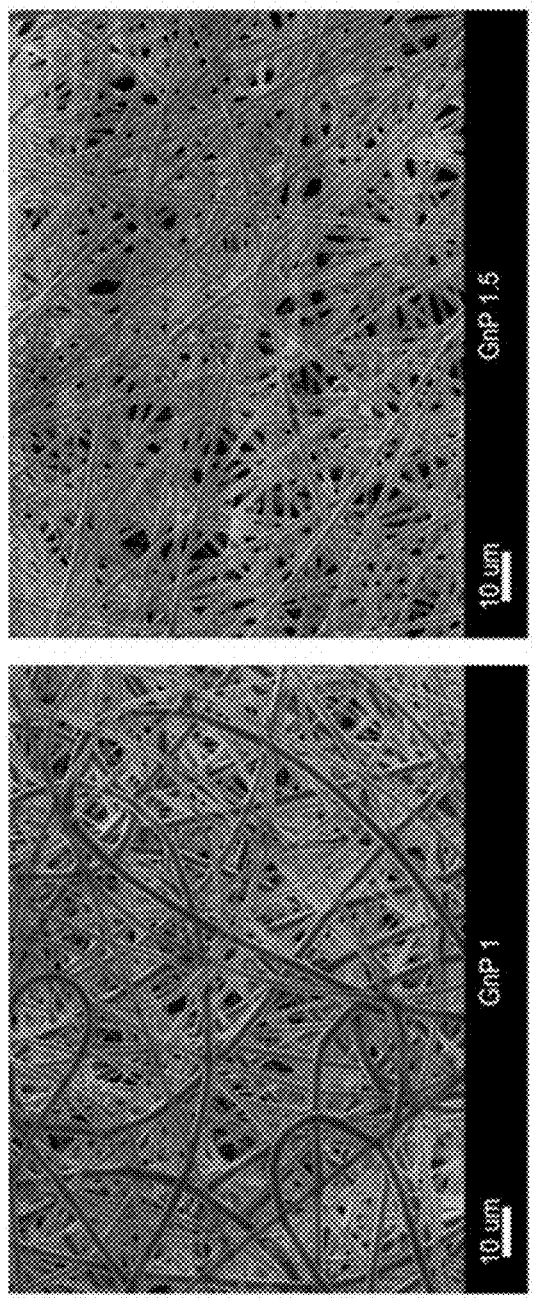
Figure 6C:
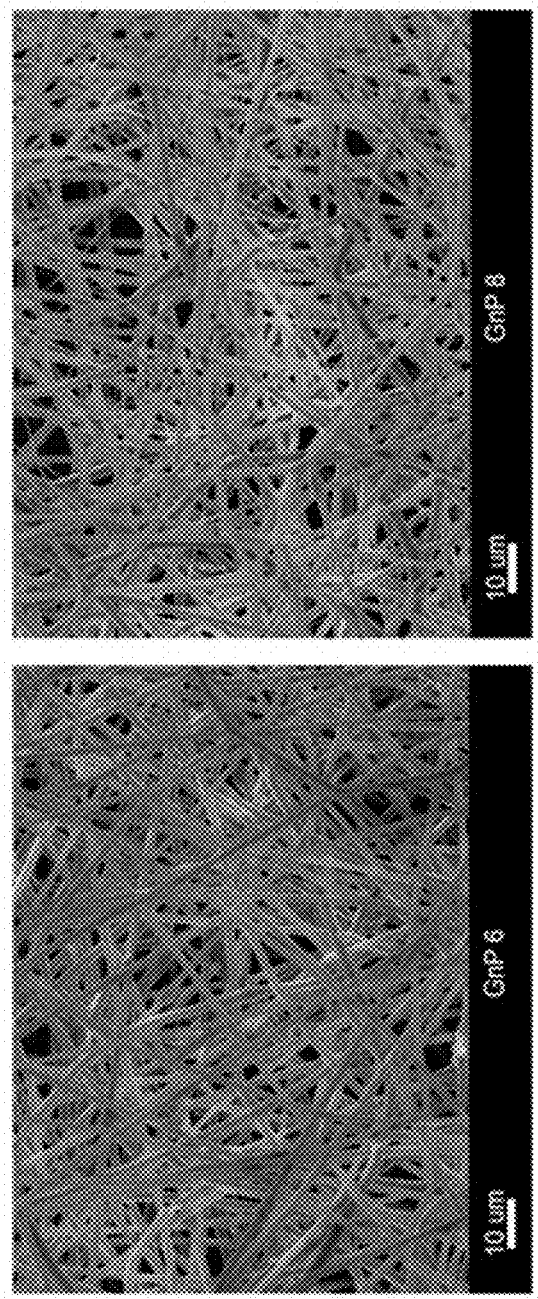
Figure 6D:
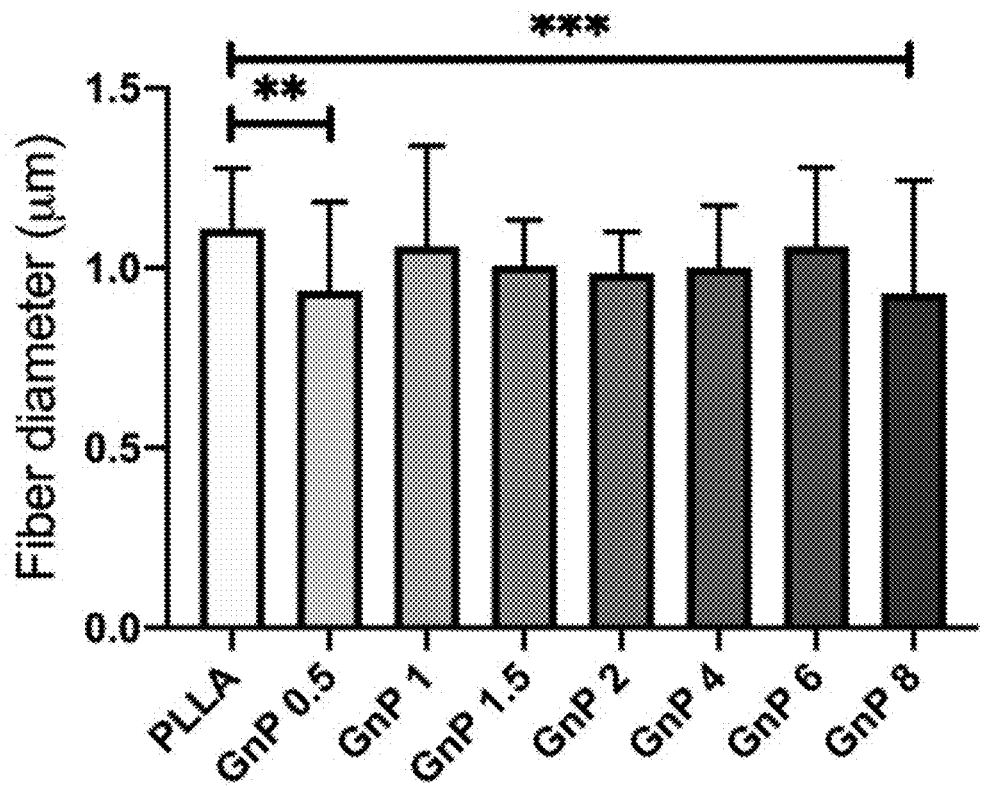
Figure 6E:
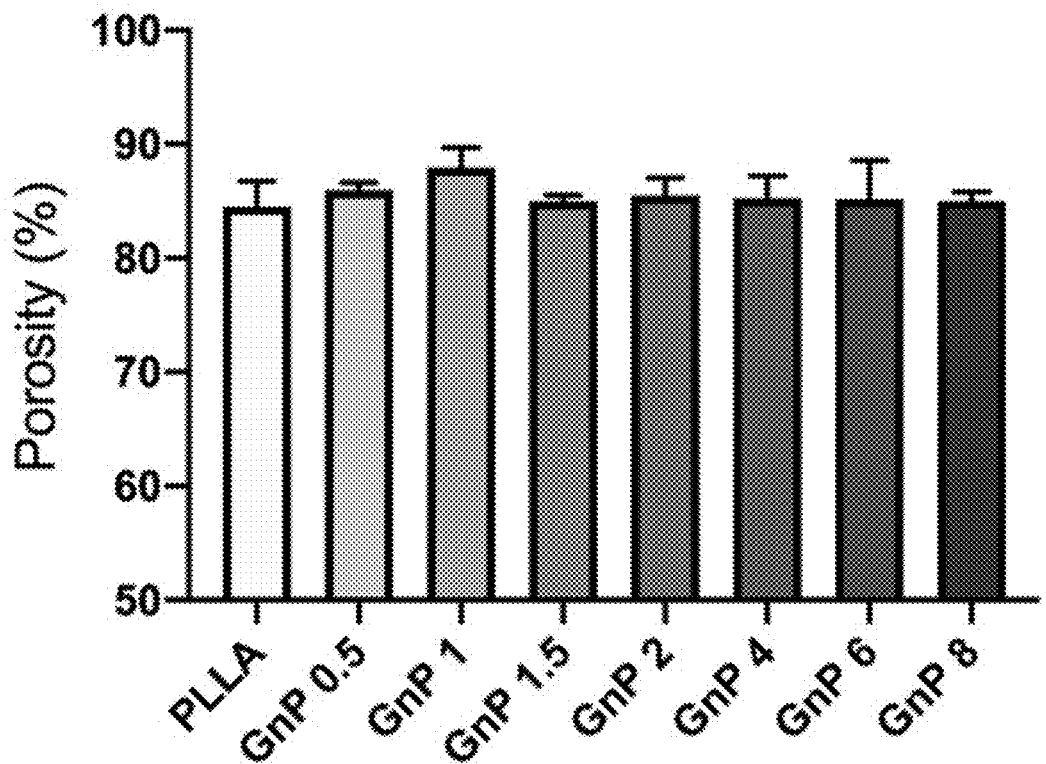

FIGS. 6A-6C show photographs and SEM micrographs of the scaffolds with different concentrations of GnPs. The color of all the samples except pure PLLA was grey, and the color intensity increased for the higher concentration of GnPs (FIG. 6A). SEM images demonstrate the fabrication of uniform and bead-free nanofibers with random orientation for all GnP concentrations (FIGS. 6B and 6C). The beads are one of the most common defects for electrospun nanofibers. The incorporation of GnP might have increased the surface charge density of the jet during electrospinning which subsequently resulted in sufficient elongation of the jet and the formation of uniform nanofibers. As shown in FIGS. 6D and 6E, adding a small amount of GnPs into the polymeric solution showed negligible effects on the mean diameter of the fibers and porosity of the mats. The mean diameter of the random fibers for pure PLLA was 1110±167 nm which decreased to 928.9±314-1061±218 nm for GnP incorporated scaffolds (FIG. 6D; ns=P>0.05, n=50). As shown in FIG. 6E, the porosity of the nanofibrous mats was in the range of 84.5%-87.9% (ns=P>0.05, =P≤0.01, *=P≤0.001; n=5).

Porosity of the Scaffolds:

The porosity of the electrospun fibers was calculated by the following equations:

$$\text{Porosity (\%)} = \left(1 - \frac{\text{fiber mat apparent density}}{\text{Bulk density of scaffold}\left(\frac{mg}{mm^3}\right)}\right) \times 100$$

fiber apparent density $$\left(\frac{mg}{mm^3}\right) = \left[\frac{\text{fiber mat mass (mg)}}{\text{fiber mat thickness (mm)} \times \text{fiber mat area (mm}^2)}\right]$$

Fourier Transform Infrared Spectroscopy (FTIR):

The attenuated total reflection Fourier Transform Infrared Spectroscopy (ATR-FTIR) spectrum of each sample was recorded by a Nicolet iS10 spectrometer (Thermo Scientific, USA), equipped with a SMART iTR accessory and controlled by Omnic 8.0 software. The spectra were obtained with about 200 scans per sample in the range of 650-4000 $cm^{-1}$.

Figure 7A:
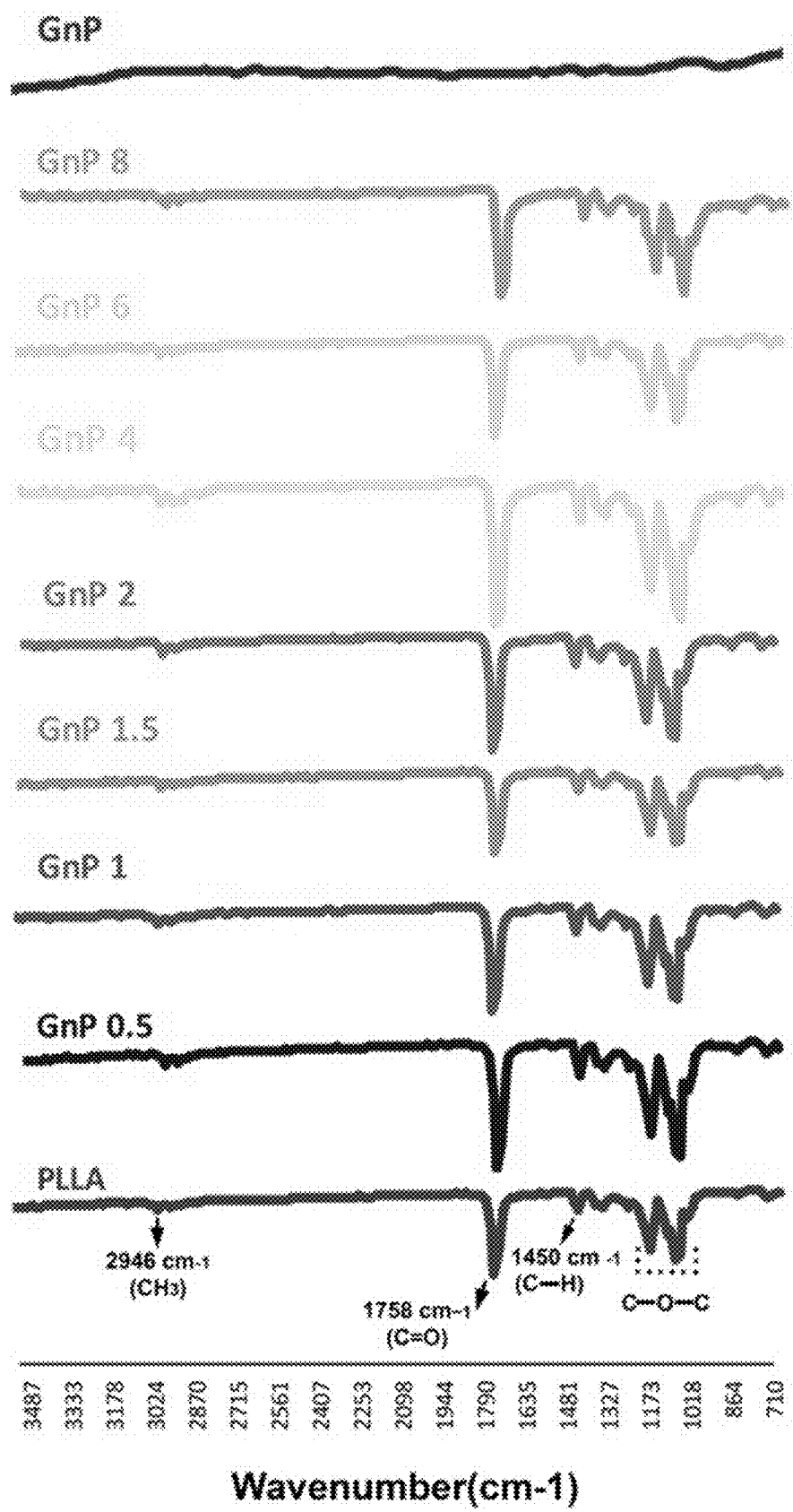
FIG. 7A through FIG. 7E show different characterizations of various ratios of randomly oriented graphene nanofibers and graphene nanoplatelets (GnPs), including FTIR spectra (FIG. 7A), electrical conductivity (FIG. 7B), and mechanical properties such as elongation percentage at break (FIG. 7C), ultimate strength (FIG. 7D) and Young's modulus (FIG. 7E).

FIG. 7A shows the FTIR spectra of the samples with different concentrations of GnPs. The result of the pristine GNPs confirmed the absence of functional groups. As shown in FIG. 7A all PLLA incorporated samples demonstrated a significant absorption band corresponds to the PLLA carbonyl group at 1758 $cm^{-1}$ (C=O). The peaks at 1080 $cm^{-1}$, 1450 $cm^{-1}$, and 2946 $cm^{-1}$ belong to C—O antisymmetric stretching, C—H deformation vibration, and C—H stretching of methyl groups, respectively. The vibrations correspond to C—O—C stretching were at 1357 $cm^{-1}$, 1265 $cm^{-1}$, 1188 $cm^{-1}$. The surface functional group characterization indicated that no significant structural change or molecular chain interaction has occurred during the fabrication process of scaffolds.

Electrical Conductivity:

The conductivity of the scaffolds (1 inch×1 inch, n=4) was measured using a four-point probe technique in an Alessi probe station. The space between the probes was adjusted based on this formula $$t \leq \frac{S}{2},$$

where s is me distance between reference electrodes, and t is the thickness of the sample. The resistivity of the conductive matrix is equal to:

$$\rho(\Omega.cm) = \frac{\pi \times t}{Ln(2)} \times \frac{V}{I} = 4.532 \times t \times \frac{V}{I}.$$

And the conductivity is the inverse of resistivity and equal to:

$$\sigma(S/cm) = \frac{1}{\rho},$$

where σ is conductivity, ρ is the resistivity of the sample, V is the voltage difference and I is the current difference between electrodes.

Figure 7B:
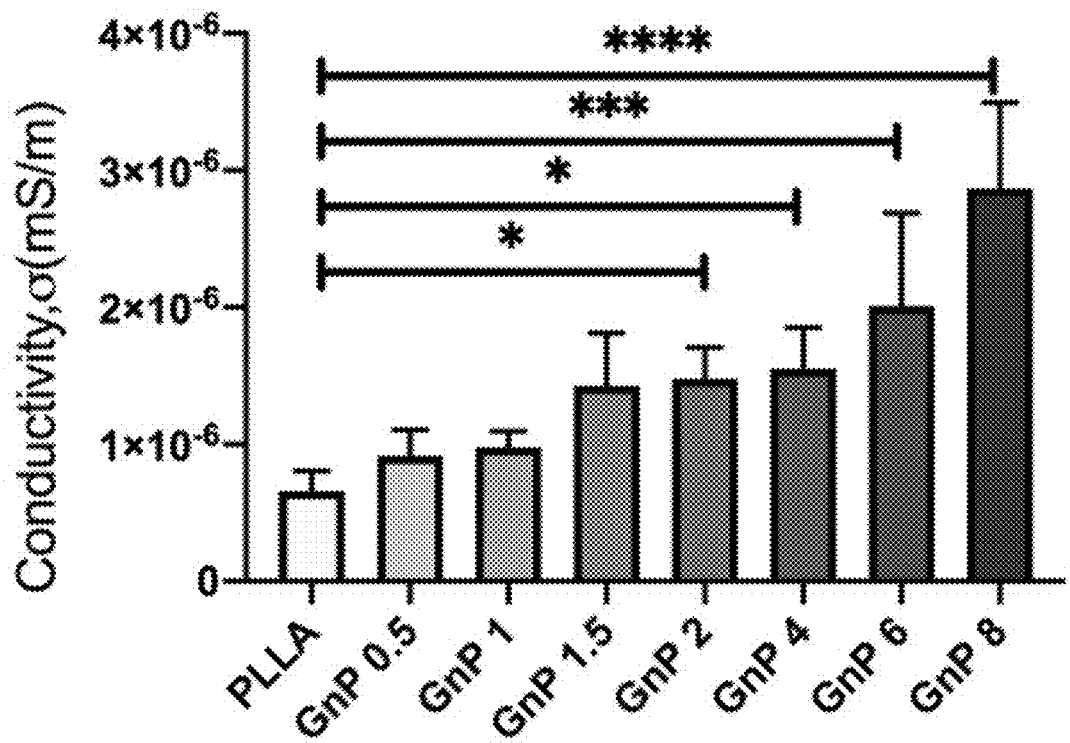

The pure PLLA nanofibers showed the lowest conductivity of $6.58\times10^{-7}\pm1.49\times10^{-7}$ (mS/m) (FIG. 7B). However, the combination of GnPs into the PLLA nanofibers increased the conductivity of the scaffolds to $2.87\times10^{-6}\pm6.27\times10^{-7}$ (mS/m) for GnP 8. The four-point probe results indicated the homogeneous incorporation of GnPs into PLLA nanofibers increased the surface conductivities of the scaffolds according to the concentration of GnPs.

Mechanical Properties:

The mechanical properties of the aligned and randomly oriented scaffolds with different concentrations of GnPs were characterized using an Instron machine tester (3 samples per group). To perform the mechanical testing, the scaffold was mounted in parallel with the axis of displacement of the Instron uniaxial testing machine at a strain rate of 10 mm/min. The ultimate tensile strength, Young's modulus, and elongation at break of the scaffolds were calculated and compared with control groups.

Figure 7C:
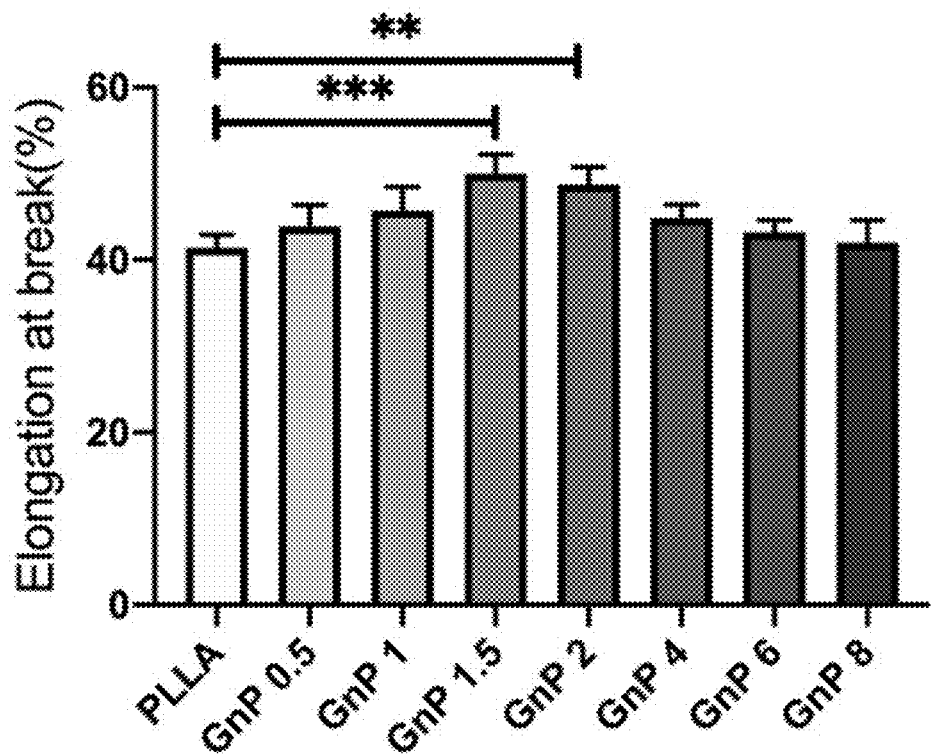
Figure 7D:
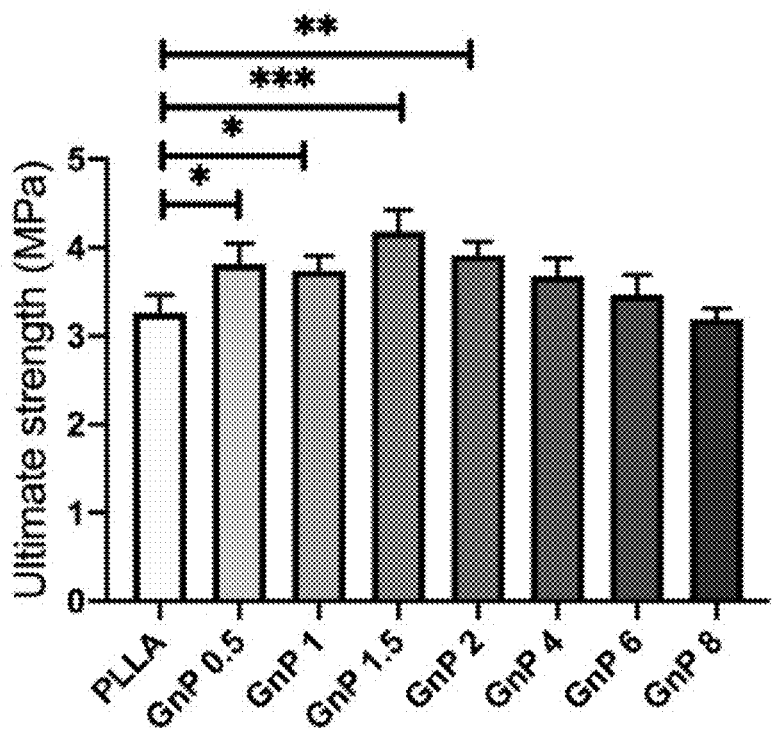
Figure 7E:
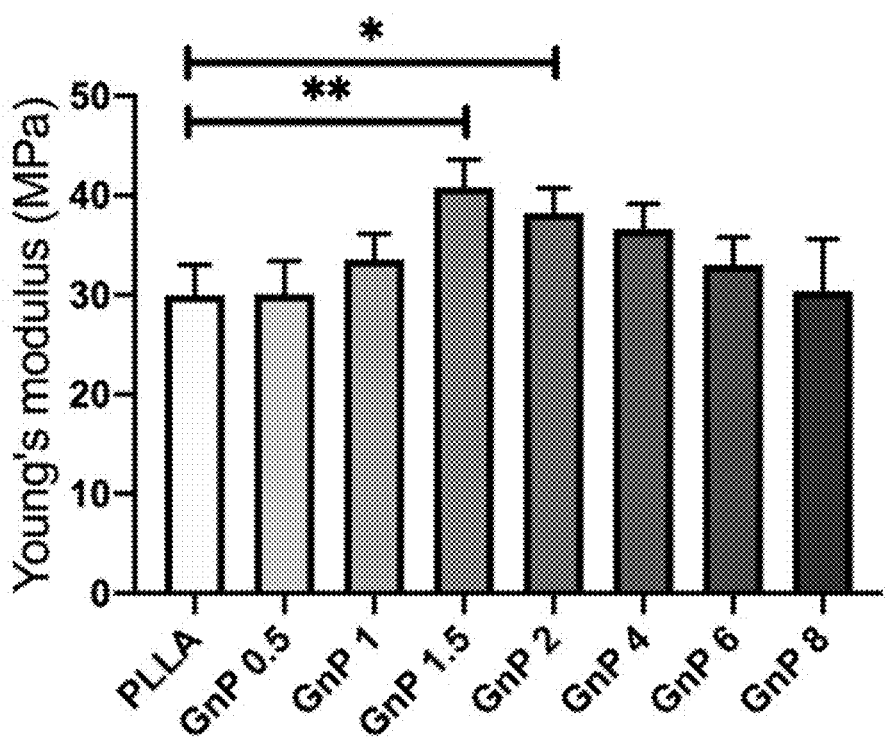

FIGS. 7C-7E show the mechanical properties of the GnPs/PLLA nanofibers with random orientation. The addition of a small amount of GnPs (GnP 0.5) did not change the elasticity and Young's modulus of the scaffold compared with pure PLLA (FIGS. 7C-7E). Though, by increasing the concentration of GnP, the elasticity, tensile strength, and Young's modulus of the scaffolds increased (FIGS. 7C-7E). GnP 1.5 demonstrated the most desirable mechanical properties compared with the other group members. The tensile strength and modulus decreased for higher concentrations of GnPs (GnP 4, 6, and 8), which may be attributed to non-uniform dispersion of the GnPs inside the fibers. GnPs show large Van der Waals forces and strong π-π interactions, which can limit the functioning of GnP-based composite by the aggregation of graphene sheets. Thus, the non-uniform dispersion of GnPs in high concentrations can cause a decrease in tensile strength. Also, the addition of GnPs decreased the elasticity, which can be attributed to the movement restriction of PLLA chains as the result of the large aspect ratio of GnPs and the interaction between GnPs and PLLA. Overall, the incorporation of GnPs reinforced the electrospun nanofibrous scaffolds. Particularly, low concentrations of GnPs significantly enhanced the tensile strength, tensile modulus, and elasticity of the scaffolds compared with pure PLLA. (ns=P>0.05, *=P≤0.05, =P≤0.01, *=P≤0.001, ****=P≤0.0001; n=4 for electrical conductivity and n=3 for mechanical properties).

Example 3: In Vitro Testing of Scaffolds

C2C12 Cell Culture:

C2C12 myoblasts (ATCC CRL-1772, USA) were used to study the effects of guidance cues on cell proliferation and differentiation. Cells were cultured in standard growth media (GM) consist of Dulbecco's Modified Eagle Medium (DMEM, from Gibco, USA) supplemented with 10% fetal bovine serum (FBS, from Gibco, USA) and 1% penicillin/streptomycin (p/s, from Gibco, USA). The scaffolds (1 cm×1 cm) were sterilized by immersion in 70% ethanol and irradiation with UV for 30 min/side, followed by subsequent washing with PBS.

The scaffolds were seeded with cells at a density of 50,000 cells/scaffold and incubated at 37° C., 5% CO2 to adhere for an hour before adding GM. The cell-seeded scaffolds were cultured with GM for 3 days, 7 days, and 14 days and the GM was changed every 3 days. To investigate cell differentiation, the myoblasts were seeded on the scaffolds in both GM and differentiation media (DM, DMEM supplemented with 5% horse serum and 1% p/s) for an additional 7 days. The cell-seeded scaffolds were incubated at 37° C., 5% $CO_2$, and the media was changed every other day.

Myoblast Viability and Proliferation:

The scaffolds were assayed for cell viability and proliferation using live/dead assay and Cell Counting Kit-8 (CCK-8) assay. For live/dead assay, cell-seeded scaffolds were incubated with ethidium homodimer-1 (4 μM; red fluorescence, from Thermofisher, USA) and calcein-AM (2 μM; green fluorescence, from Thermofisher, USA) in phosphate-buffered saline (PBS) for 10 min at 37° C. in a 5% $CO_2$ atmosphere incubator. Then, samples were immediately examined using confocal microscopy (ZEISS LSM 880). The cell proliferation was determined using CCK8 assay (from dojindo) for 8 samples per group (4 samples without cells as a background control for each group). The assay was performed after 1, 3, 5, and 7 days of incubation in GM. Then, 10% CCK-8 solution per well was added into the media, and samples were incubated for 2 hours at 37° C., 5% $CO_2$ in the dark (100 μL complete medium and 10 μL CCK-8 solution per well was considered as control). The values of OD 450 nm were measured using a microplate reader.

Figure 8A:
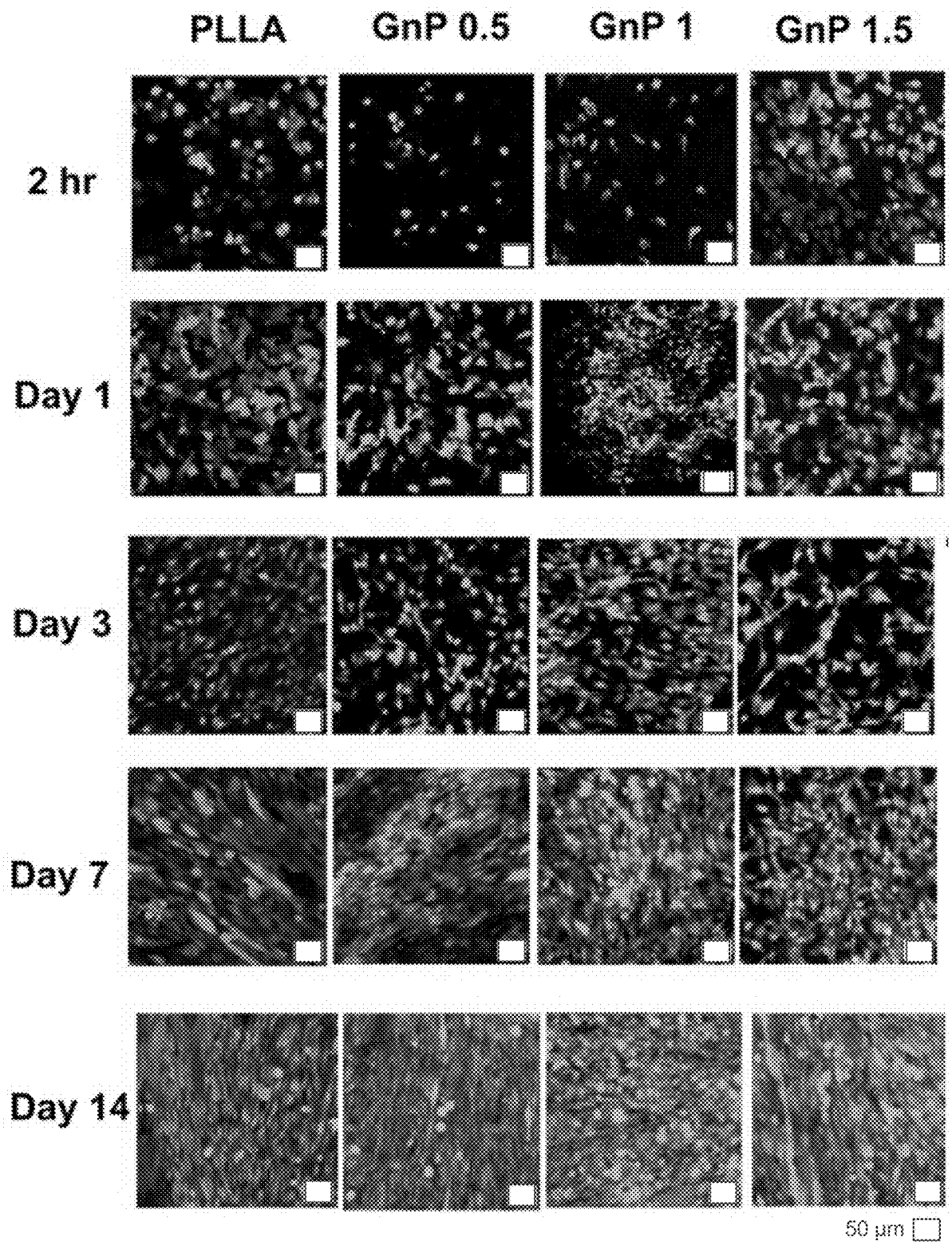
FIG. 8A through FIG. 8C show cell attachment, viability and proliferation in the presence of graphene nanofiber scaffolds.
Figure 8B:
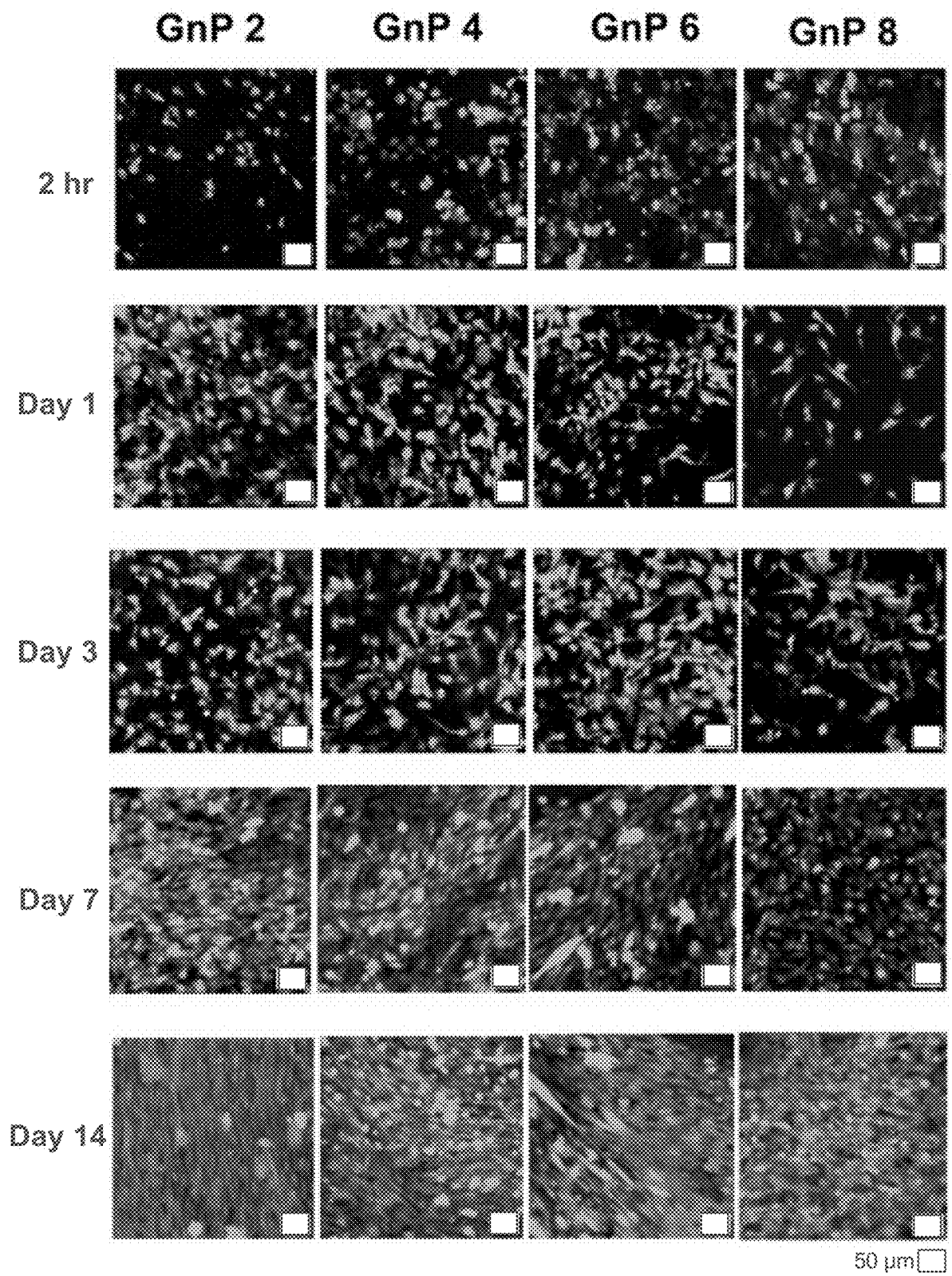
Figure 8C:
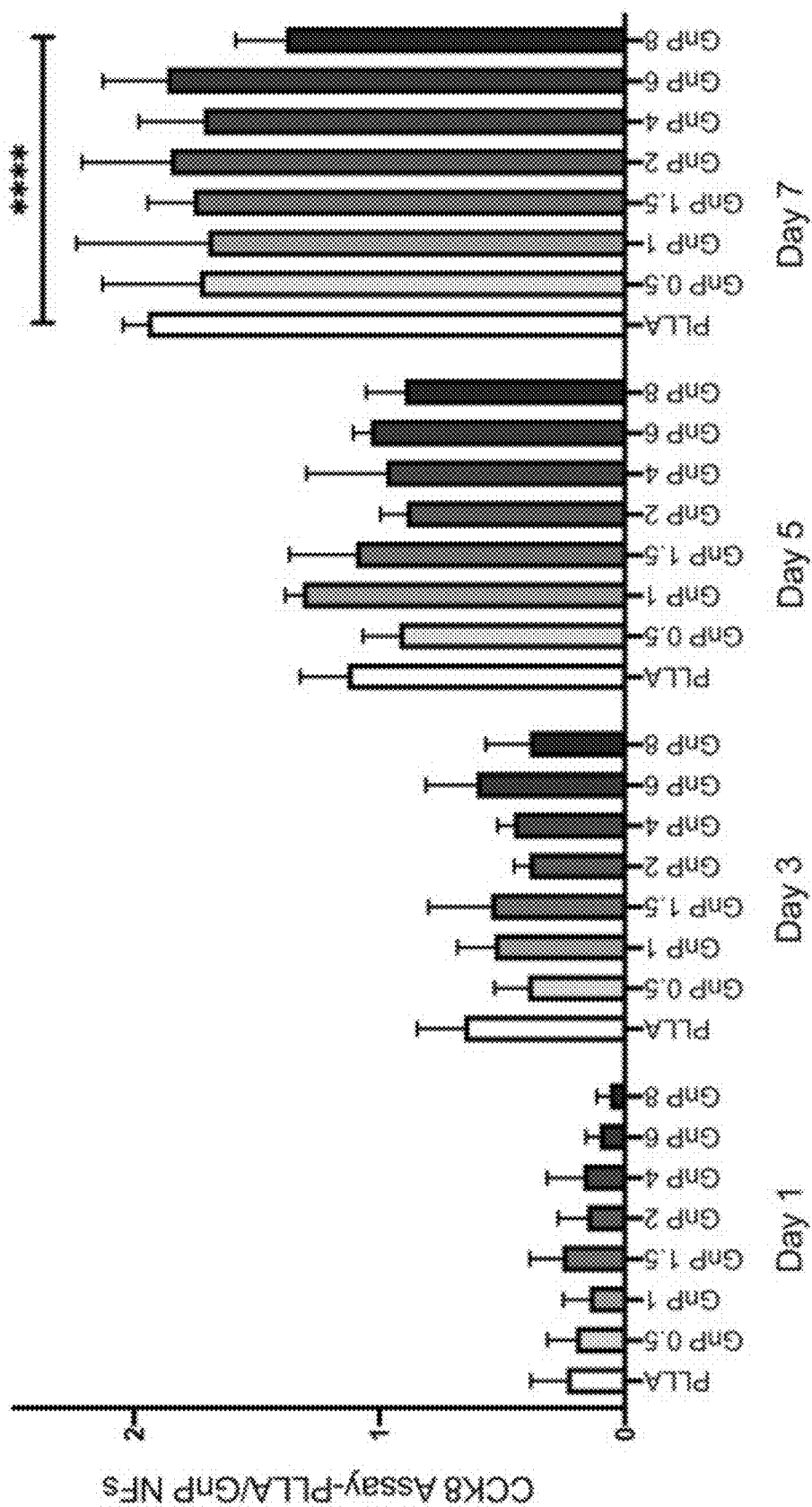

FIG. 8A shows successful cell attachment on the scaffolds two hours after cell culture. Based on the results, the majority of the myoblasts were viable, and all concentrations of GnPs supported the cell viability 24 hours post-seeding. The myoblasts viability and proliferation demonstrated a significant increase after three days, suggesting that the GnP-based scaffolds were cytocompatible. To quantitatively define the viability of the cells and the effect of GnPs on myoblasts proliferation, the CCK-8 assay was used. As shown in FIG. 8B, there was no significant difference regarding initial cell proliferation among the scaffolds one day post-seeding. However, three days after cell culturing, the number of viable cells increased. The results of cells metabolic activity are consistent with live/dead images and confirm the biocompatibility and the potential of the GnP-based scaffolds to support myoblast growth (FIG. 8). These results show that incorporating GnPs into PLLA scaffolds did not induce significant toxicity to the cells. We further evaluated the myotube formation to define the optimum concentration of GnPs, which can significantly induce myogenic differentiation. * denotes a significant difference compared with pure PLLA scaffold, n=4.

Myotube Formation Analysis:

The myotube formation was determined by immunostaining with MyoD, Myogenin (MyoG), and myosin heavy chain (MHC). The cell-seeded scaffolds were washed with PBS and fixed with 4% paraformaldehyde (Sigma-Aldrich, USA) for 5 min. The scaffolds were then washed with PBS and permeabilized with 0.1% Triton X-100 (Sigma-Aldrich, USA) for 3 min. After washing the scaffolds with PBS, the cells were blocked with 10% bovine serum albumin (BSA) (Sig-ma-Aldrich, USA) solution in PBS for 1 h followed by three times washing with 1% BSA in PBS. All steps were conducted at room temperature. Following this, the cells were incubated with primary antibodies (Anti-MyoD1 antibody (1 μg/mL, ab16148), Anti-Myogenin antibody (1 μg/mL, ab1835), and Myosin 4 Monoclonal Antibody (MF20, 1:50, DSHB) for 1 h. Then the scaffolds were incubated with secondary antibody (Alexa Fluor 488-conjugated rabbit anti-mouse IgG, 1:200, abcam (ab6725), USA) for 45 min in the dark followed by incubation with DAPI (1:1000, Thermo Fisher Scientific, USA) for 20 min. All the steps were conducted at room temperature followed by three times washing with 1% BSA in PBS. The stained cells were imaged with a confocal microscope, and the myotube length, fusion index, and maturation index were measured for each group. The fusion index was determined by the percent of myotubes with more than two nuclei, and the maturation index was calculated as the ratio of myotubes with more than five nuclei versus the total number of nuclei.

Figure 9A:
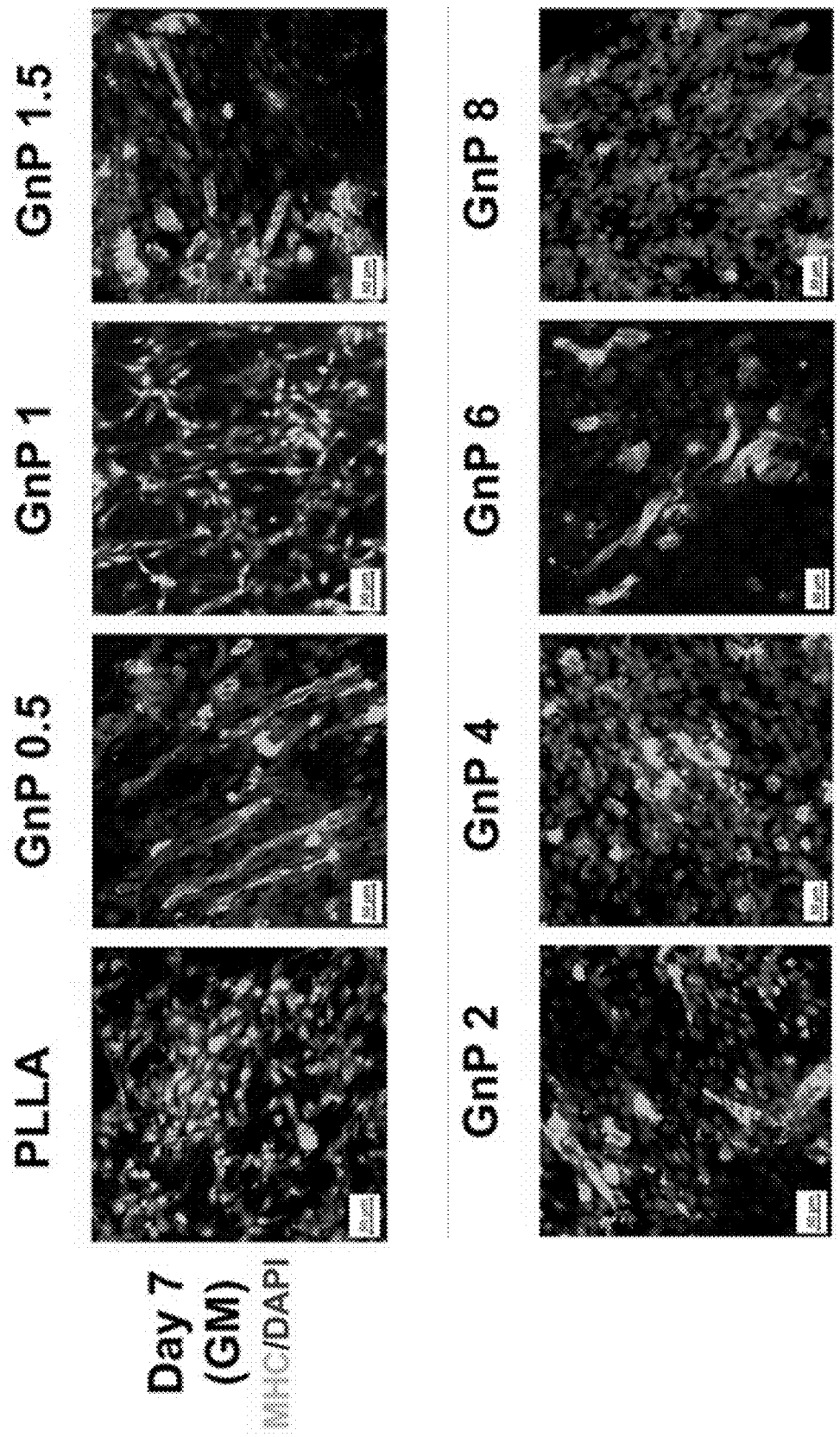
FIG. 9A through FIG. 9H show myotube differentiation and characterization after 7 days in growth media (GM.
Figure 9B:
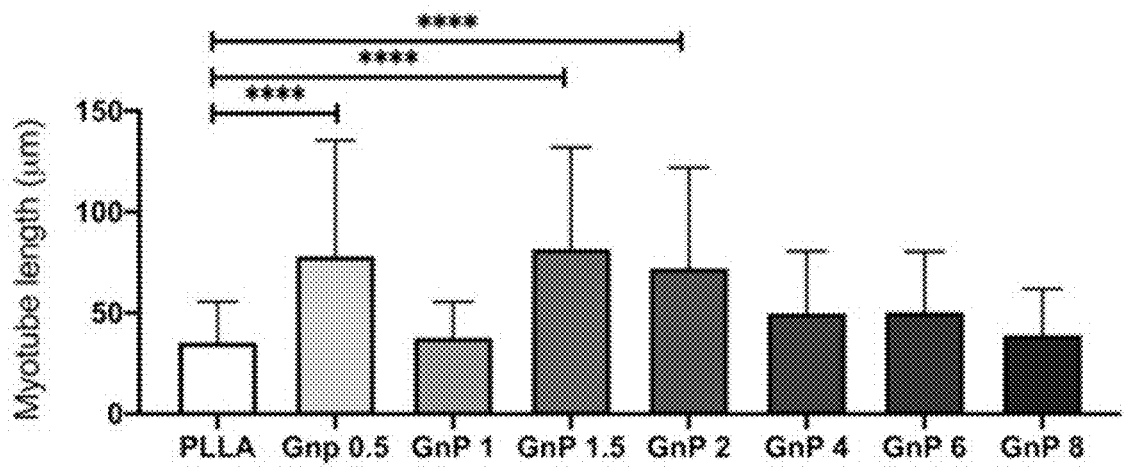
Figure 9C:
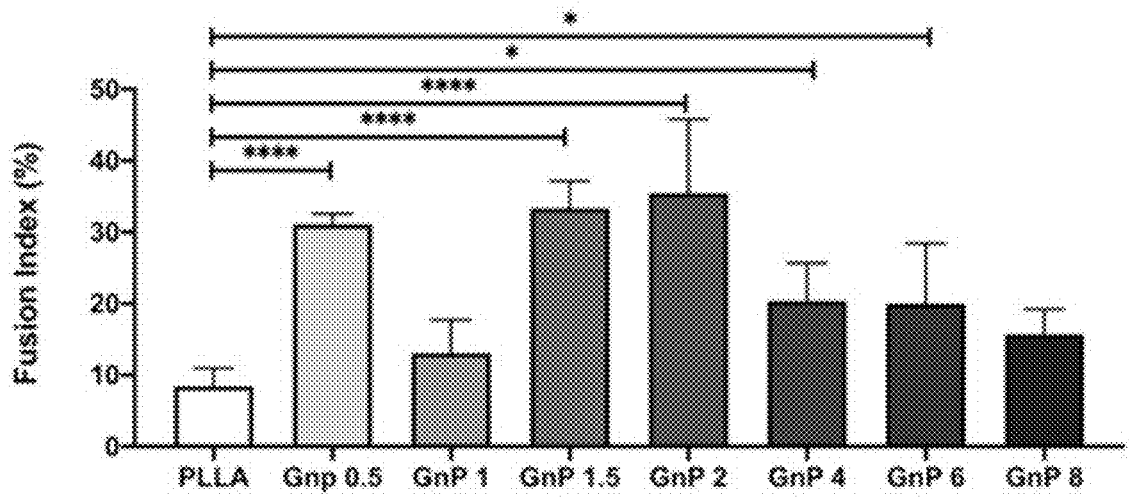
Figure 9D:
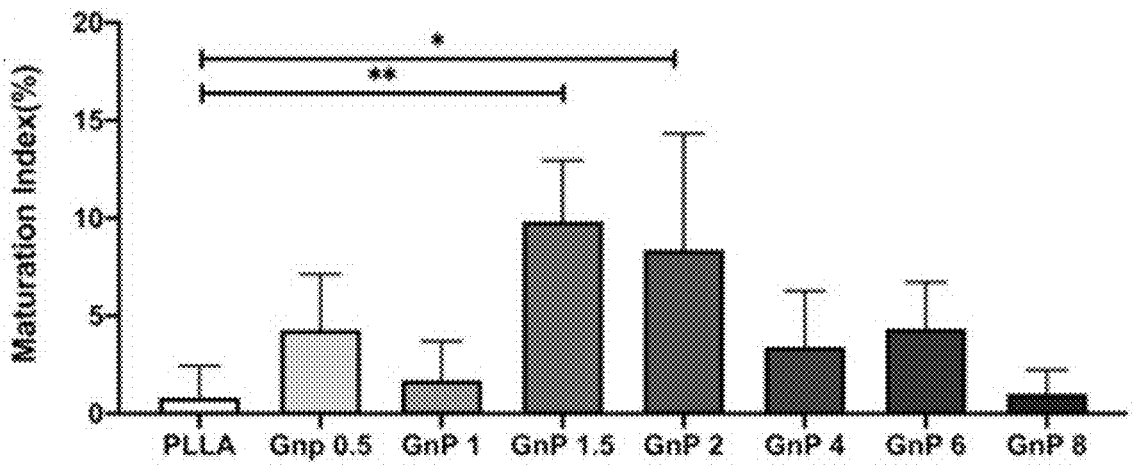

As shown in FIG. 9A, no significant myotubes were observed on the PLLA scaffold in GM. However, compared with the PLLA scaffold, GnP incorporation induced more myotube formation. The myotube length significantly increased from 35.46±20.09 μm for PLLA to 78.07±57.53 μm, 81.75±50.14 μm, and 72.07±49.86 μm for GnP 0.5, GnP 1.5, and GnP 2, respectively (FIG. 9B). The fusion and maturation indices were calculated to investigate the ability of the scaffolds to induce C2C12 myoblasts to fuse together and form multinucleate myotubes. The fusion index was determined by the percent of myotubes with more than two nuclei, and the maturation index was calculated as the ratio of myotubes with more than five nuclei versus the total number of nuclei. As shown in FIG. 9C, the fusion index significantly increased by the addition of GnPs in GnP 0.5 (31.08±1.522%), GnP 1.5 (33.31±3.841%), and GnP 2 (35.43±10.34%) compared with pure PLLA (8.446±2.526%). Also, similar results were observed for the maturation index and GnP 1.5 (9.84±3.1%) and GnP 2 (8.378±5.947%) showed the highest values of maturation compared with pure PLLA and other groups. The addition of GnPs (GnP 4, GnP 6, and GnP 8) demonstrated the higher value of myotube length, fusion, and maturation indices compared with pure PLLA; however, these results did not show significant outcomes compared with GnP 0.5, GnP 1.5, and GnP 2.

Figure 9E:
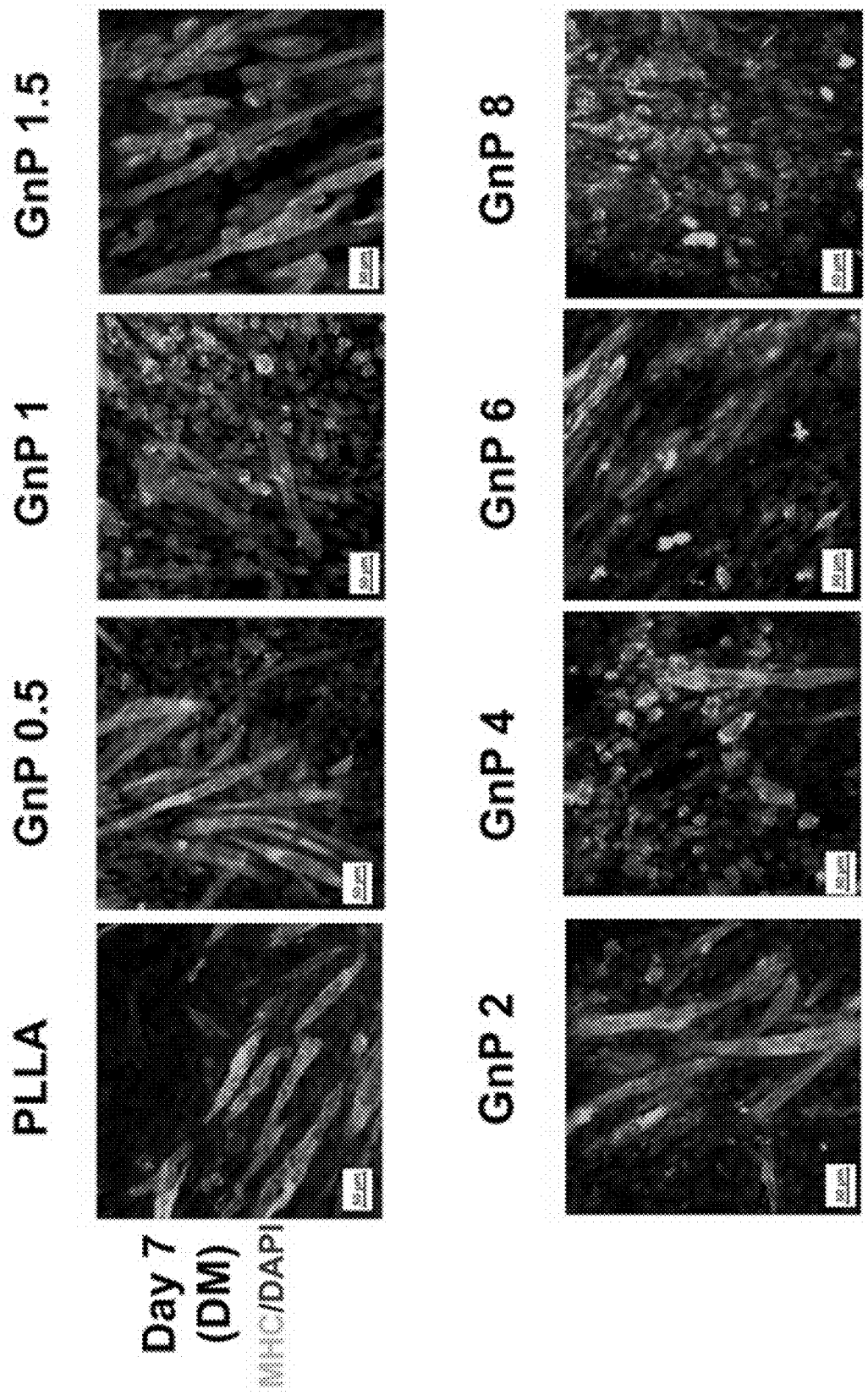
Figure 9F:
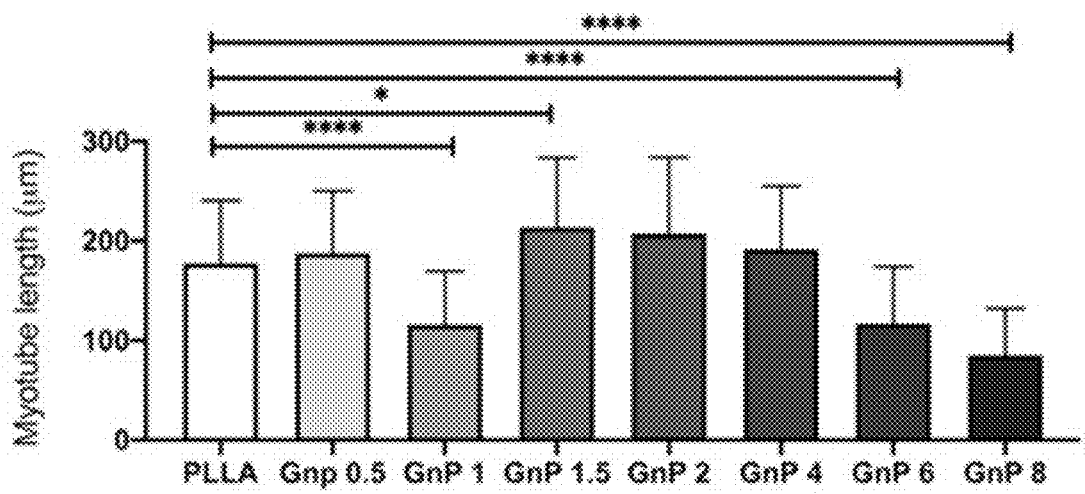
Figure 9G:
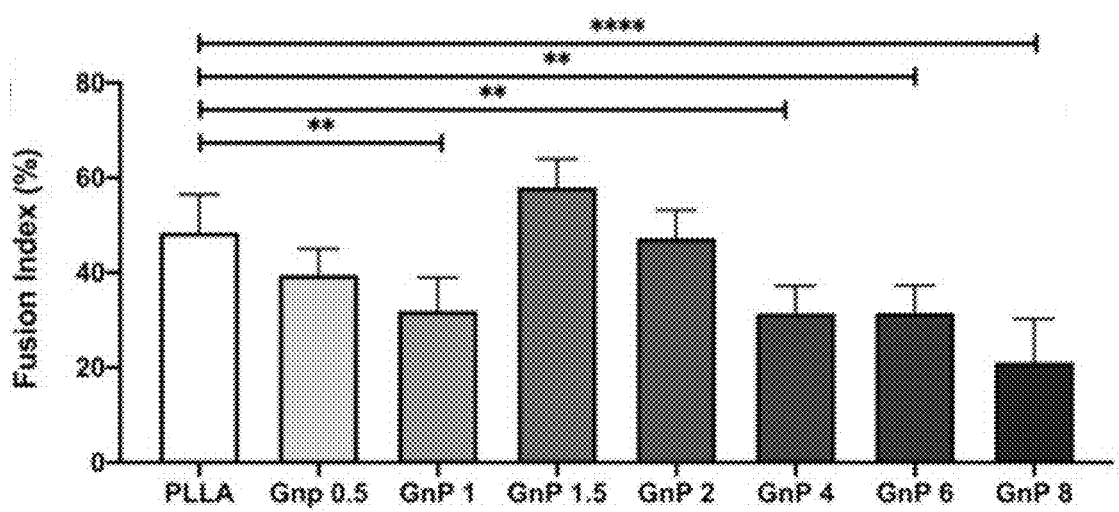
Figure 9H:
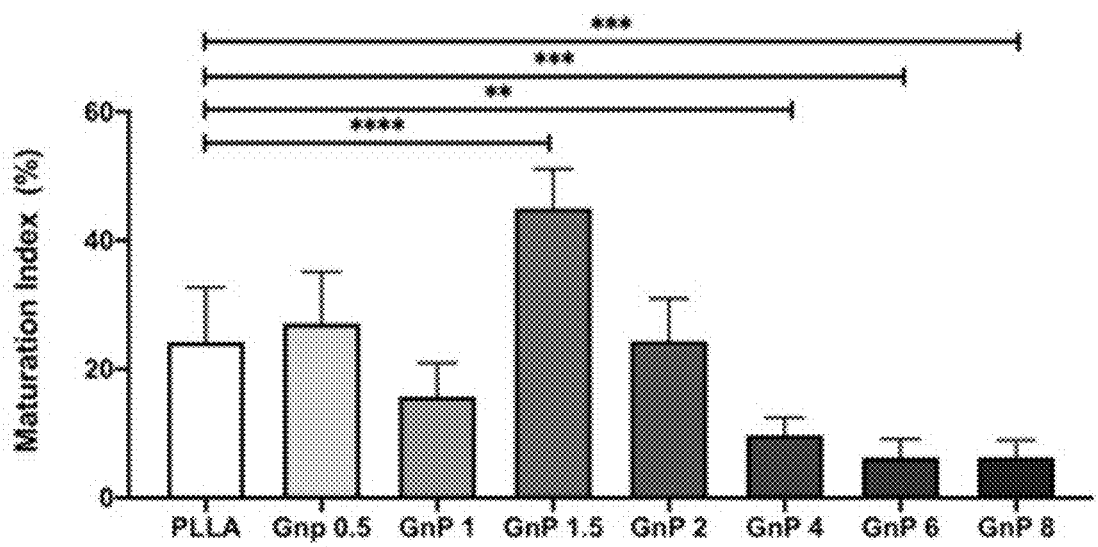

The results of myotube formation and maturation on the scaffolds in GM showed the significant efficacy of GnPs as an electrical cue for muscle tissue regeneration without the need for external electrical stimulation. C2C12 myoblasts usually start differentiation and myotube fusion/maturation in DM. Studies show that to induce C2C12 to differentiate, their proliferation ability needs to be inhibited by decreasing the serum concentration and adding specific protein. Here, it was shown that even in standard GM, the GnP-based scaffolds can induce both myoblast proliferation and differentiation (FIG. 8 and FIGS. 9A-9D). Further, the differentiation potential of the scaffolds in DM was evaluated. FIG. 9E exhibited the significant formation of myotubes on all scaffolds. The length of myotube, fusion and maturation indices were significantly increased, and PLLA, GnP 0.5, GnP 1.5, and GnP 2 demonstrated the best myotube morphologies compared with other groups. As shown in FIG. 9F, the myotube length increased to 177.5±63.05 187.7±62.36 μm, 213.4±70.32 μm, and 207.3±76.48 μm for pure PLLA, GnP 0.5, GnP 1.5, and GnP 2, respectively. A similar enhancement was observed for fusion and maturation indices (FIGS. 9G and 9H). The fusion index increased to 48.46±7.968% for pure PLLA, 39.48±5.547% for GnP 0.5, 57.97±5.99% for GnP 1.5, and 47.25±5.917% for GnP 2 (FIG. 9G). GnP 1.5 showed the highest value of maturation index (44.99±6.09%), which is significantly higher than other groups as indicated in FIG. 9H. Based on the results, GnP 0.5, GnP 1.5, and GnP 2 exhibited the highest values compared with other GnP-based groups in both GM and DM. Accordingly, GnP 0.5, GnP 1.5, and GnP 2 were selected for the next step. * denotes significant difference compared with pure PLLA scaffold, ns=P>0.05, *=P≤0.05, =P≤0.01, *=P≤0.001, ****=P≤0.0001; n=5.

Figure 10A:
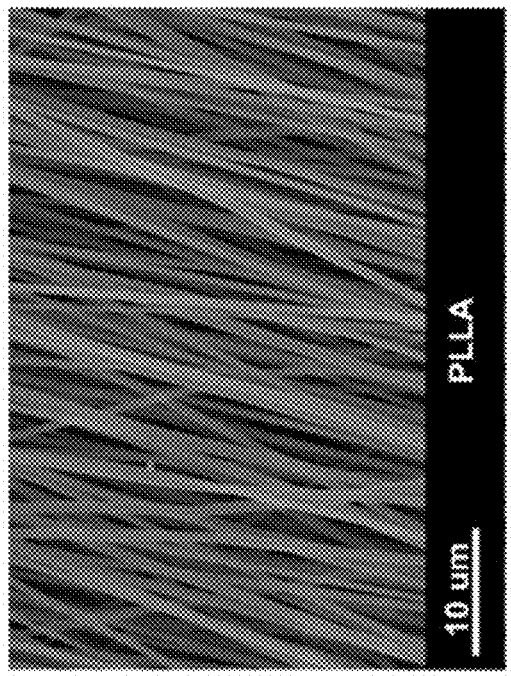
FIG. 10A through FIG. 10E show visualization (SEM images (FIG. 10A)) and characterization (fiber diameter (FIG. 10B) and mechanical properties such as ultimate strength (FIG. 10C) Young's modulus (FIG. 10D and elongation percentage at break (FIG. 10E) of various ratios of aligned nanofibers and GnPs.
Figure 10A:
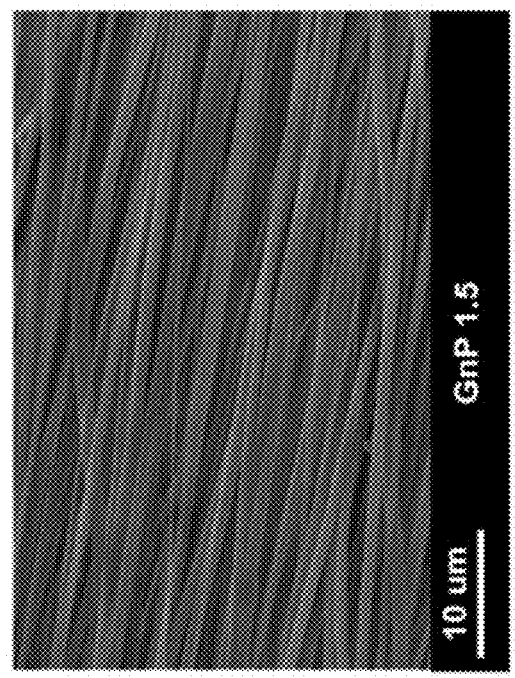
Figure 10A:
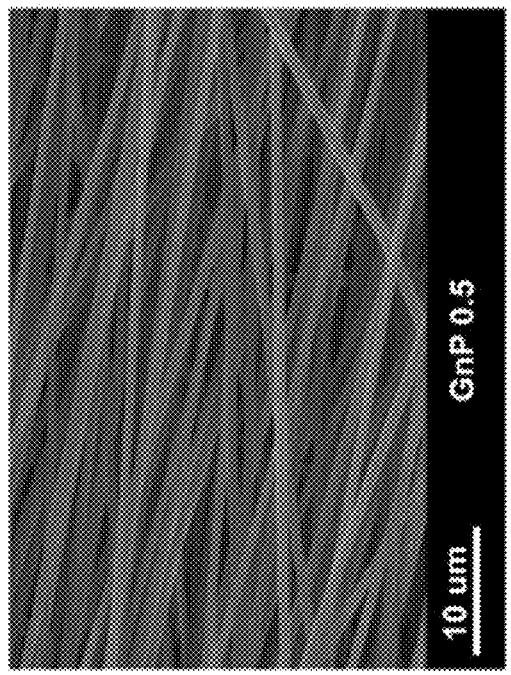
Figure 10A:
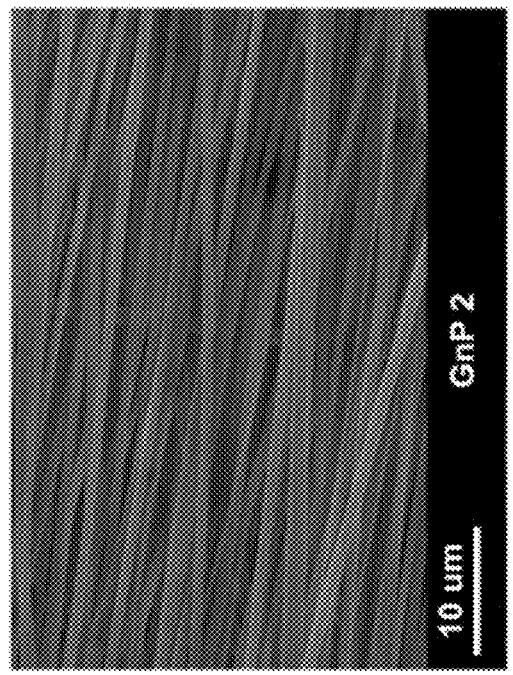
Figure 10B:
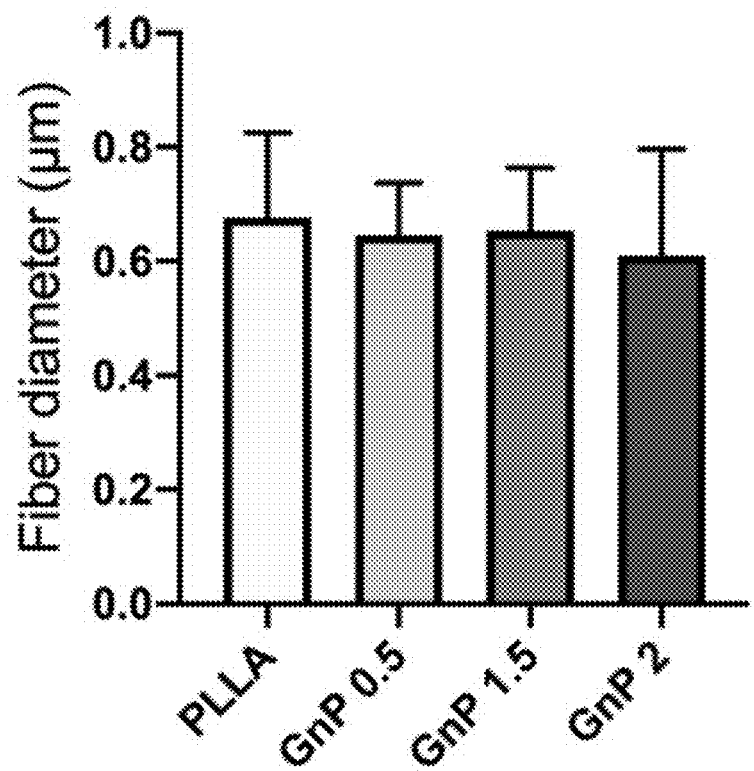
Figure 10C:
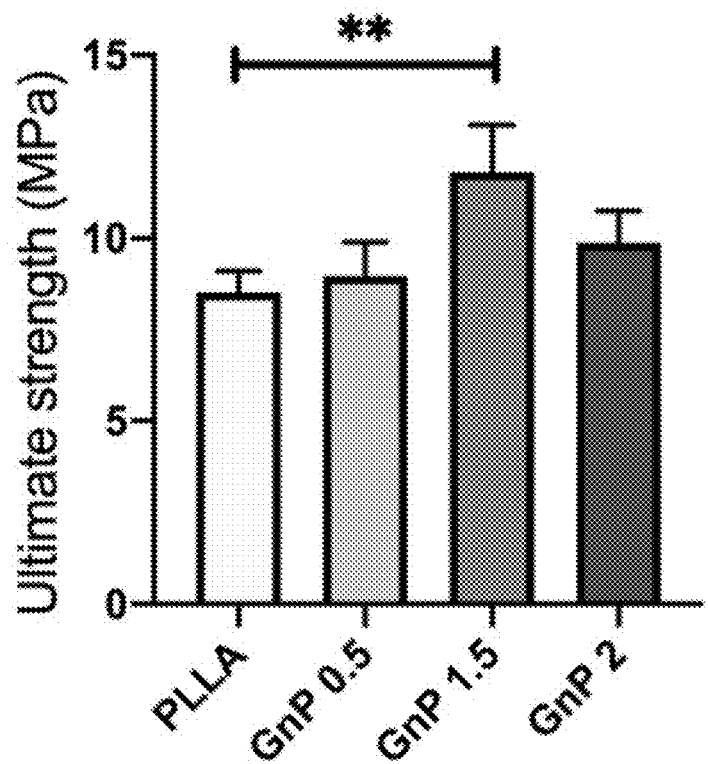
Figure 10D:
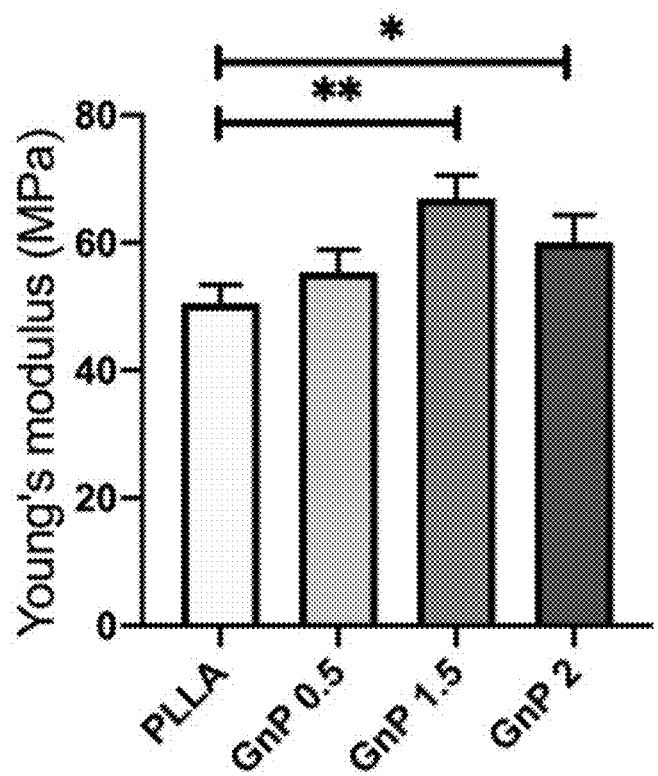
Figure 10E:
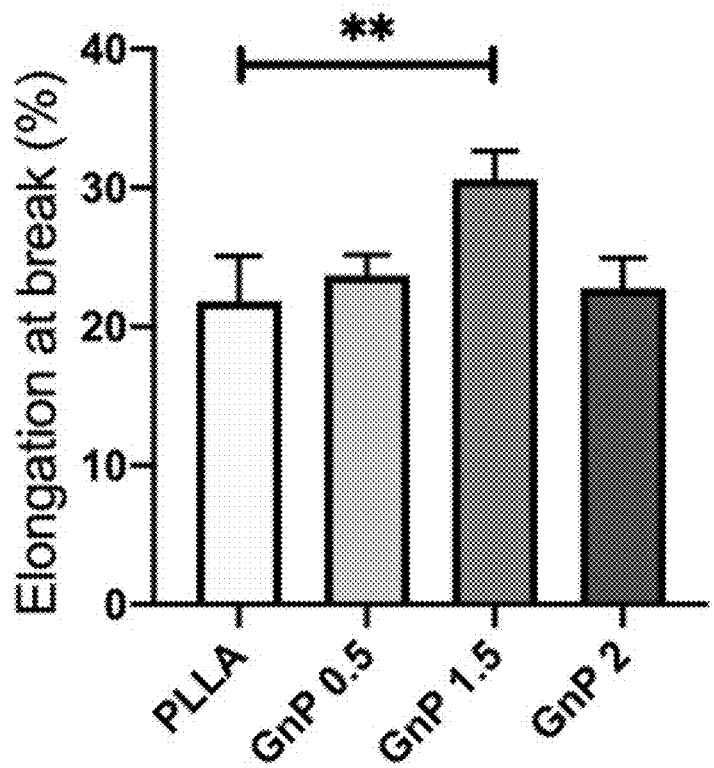

Skeletal muscle is composed of highly aligned and long multinucleated myotubes created through the fusion and differentiation of myoblasts. The aligned orientation of the scaffolds provided herein provide a vital topographical cue to mimic the natural structure of muscle tissue and enhance myoblast growth and differentiation compared with random fibers. To fabricate highly aligned nanofibers, a high-speed drum was used in the collector region. FIG. 10A shows the SEM images of the fabricated scaffolds. There are no significant differences among the average diameters of the nanofibers. The average diameter of the aligned nanofibers decreased to 676.7±149.1 nm, 645.3±91.84 nm, 652.6±110.8 nm, and 610±186.1 nm for PLLA, GnP 0.5, GnP 1.5, and GnP 2, respectively (FIG. 10B; ns=P>0.05, n=50). The alignment of the nanofibers significantly improved the mechanical properties of the scaffolds compared with randomly oriented scaffolds (FIG. 10C-10E). The ultimate tensile strength of GnP 1.5 showed the highest value of 11.80±1.296 MPa compared with pure PLLA (8.523±0.5862 MPa), GnP 0.5 (8.973±0.9151 MPa), and GnP 2 (9.870±0.8445 MPa). The results of Young's modulus and elongation at break showed significant increases to 66.93±3.645 MPa and 30.63±2.011 for GnP 1.5. Based on the results, the minimum value of ultimate tensile strength and Young's Modulus (8.523±0.5862 MPa and 50.57±2.884 MPa for pure PLLA) of aligned scaffolds are higher than the maximum value of those for randomly oriented scaffolds (4.183±0.2421 MPa and 40.81±2.803 MPa for GnP 1.5, respectively). These results are consistent with previous studies suggesting that the fabrication of aligned nanofibers can significantly increase the tensile strength and modulus of the nanofibers and decrease their elasticity compared with randomly oriented fibers. For FIGS. 10C-10E, ns=P>0.05, *=P≤0.05, **=P≤0.01.

Figure 11:
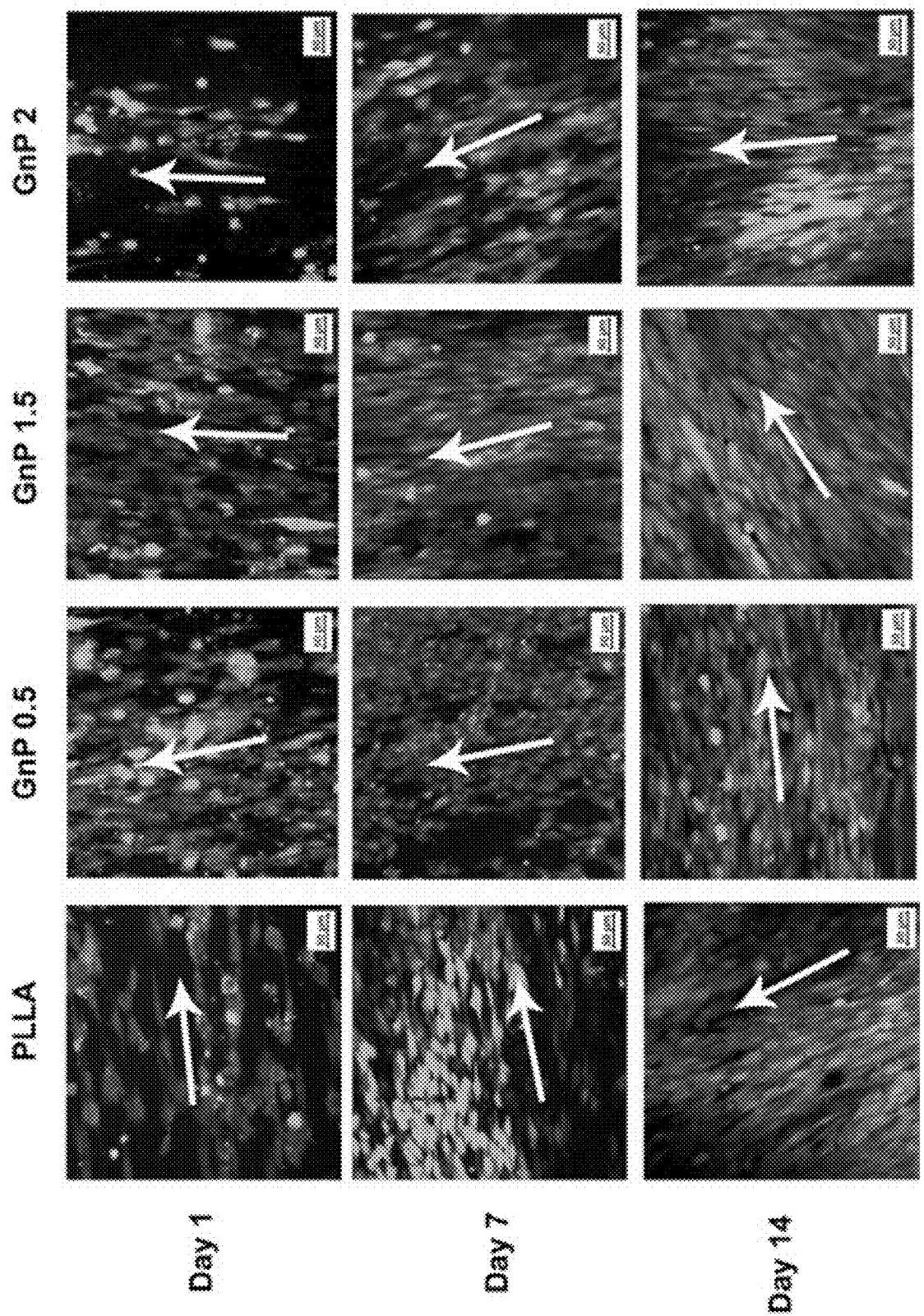
FIG. 11 shows fluorescent images of myoblasts grown over 14 days on aligned scaffolds with varying amounts of GnPs.
Figure 12A:
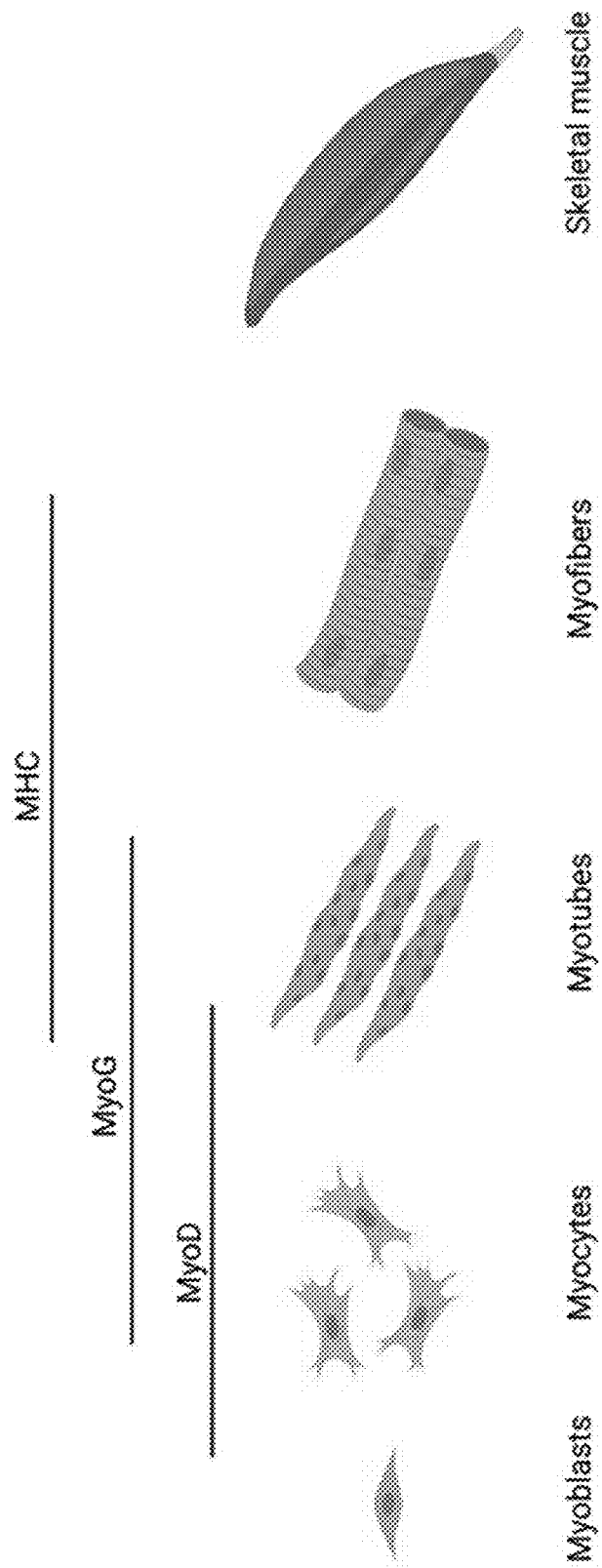
FIG. 12A through FIG. 12E show the synergistic effects of the topographical and electrical cues on myoblast differentiation and myotube formation in GM and DM.
Figure 12B:
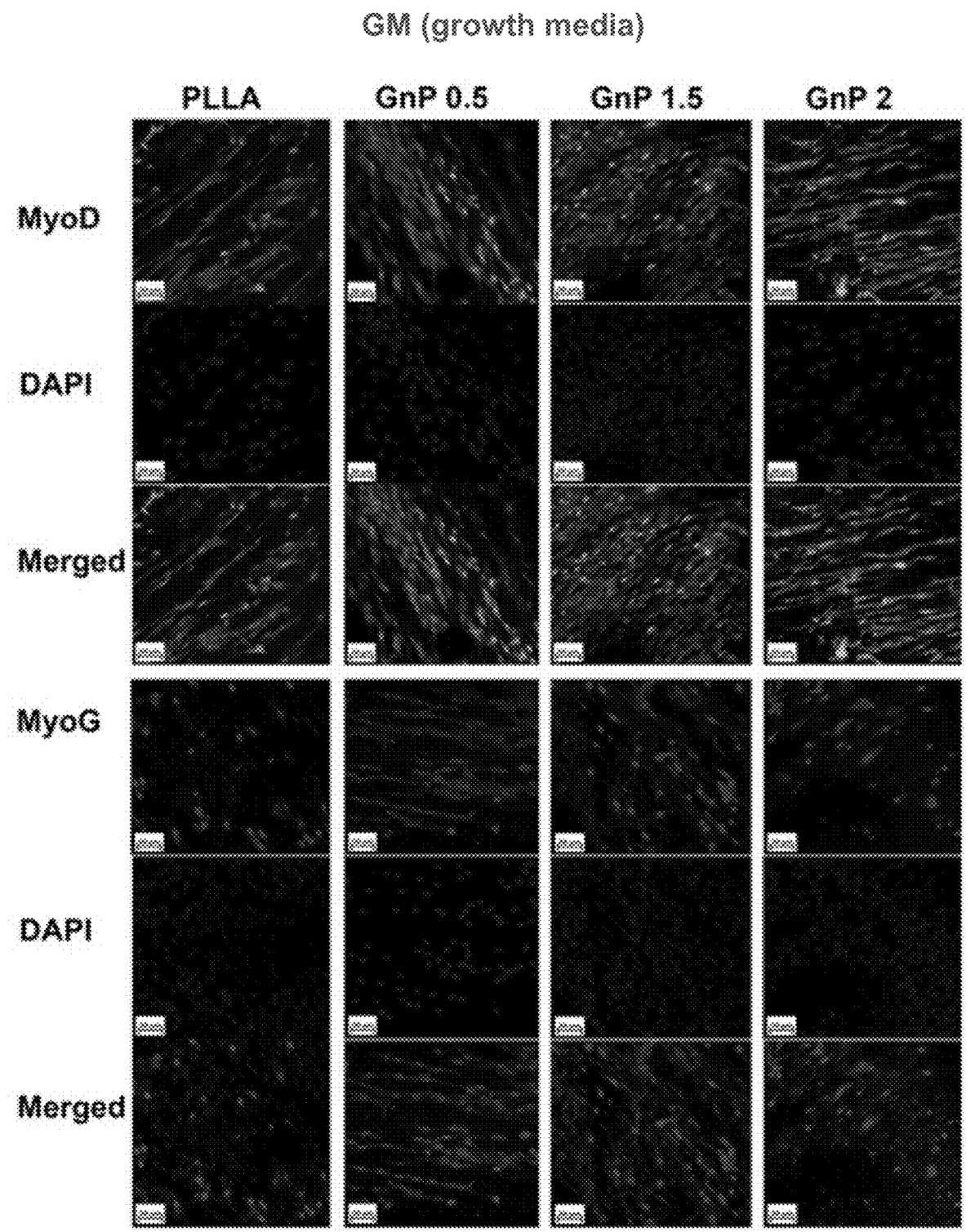
Figure 12C:
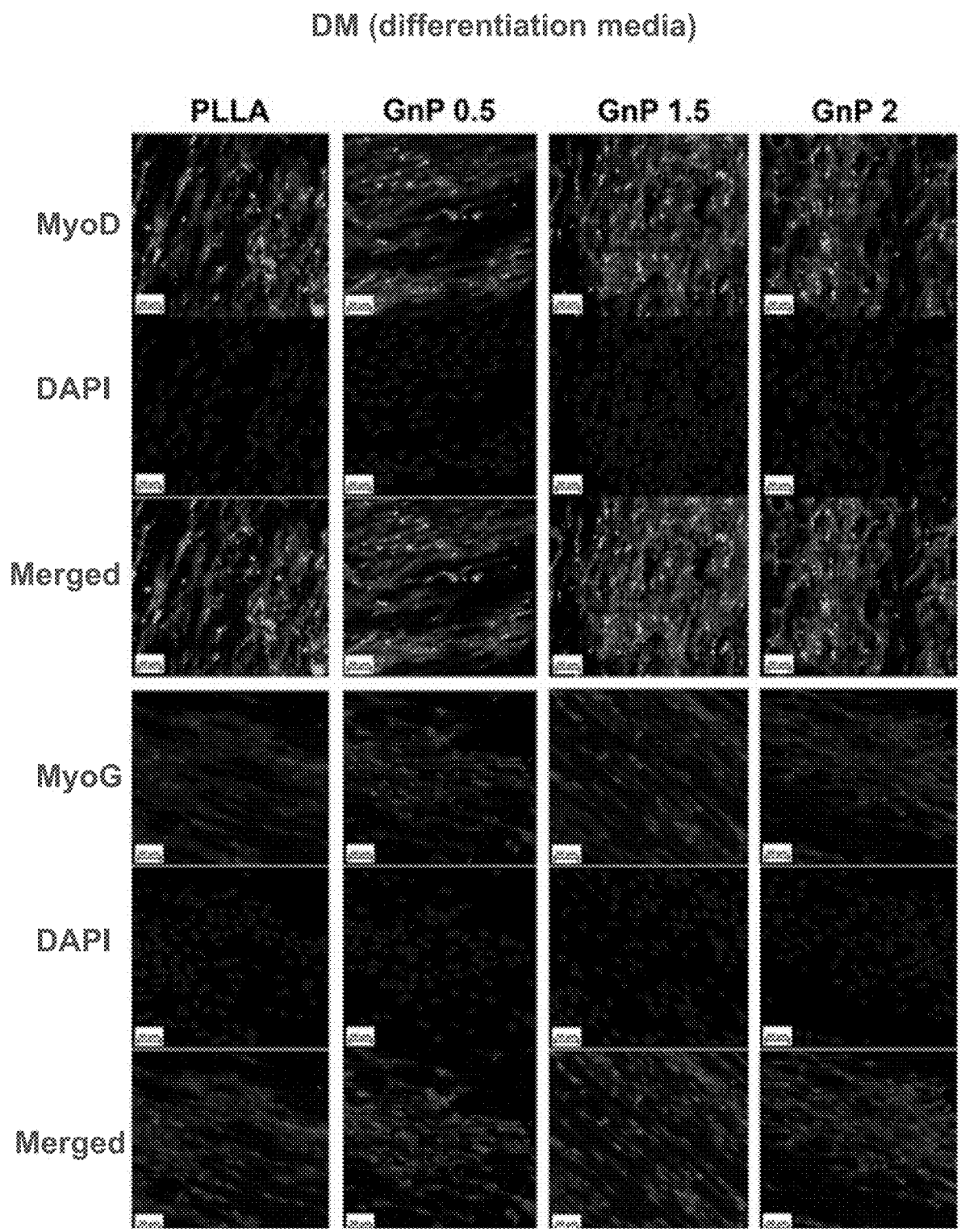
Figure 12D:
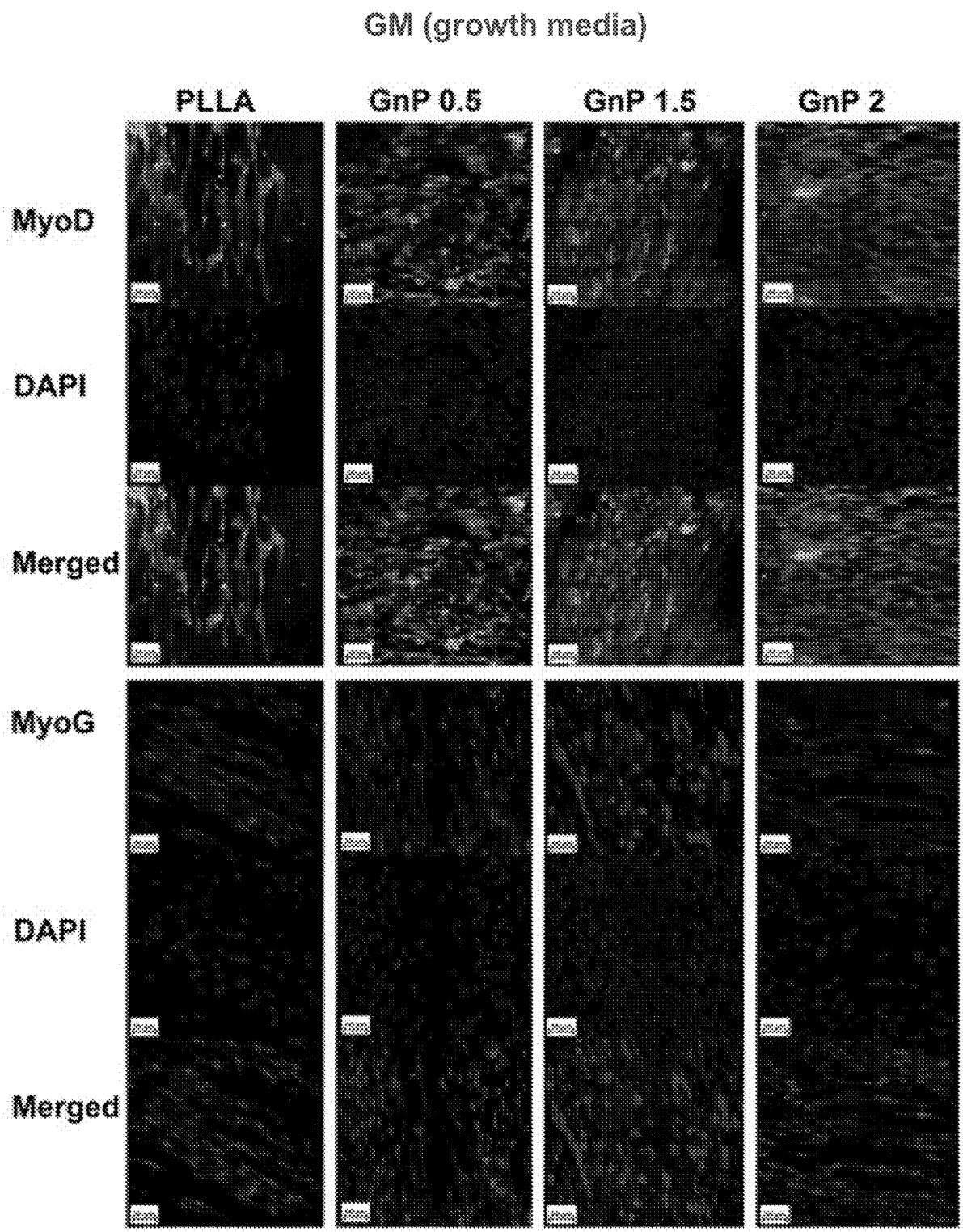
Figure 12E:
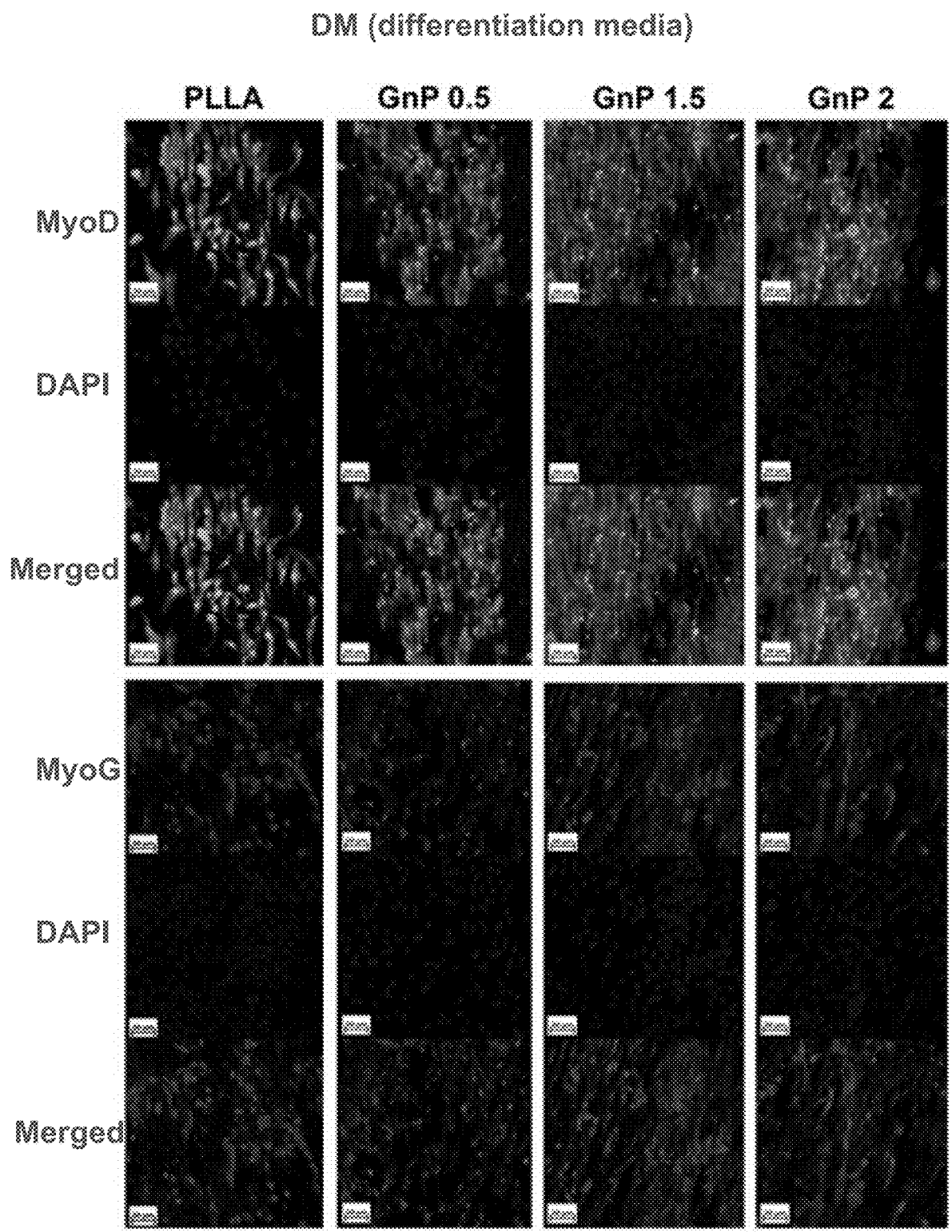
Figure 13A:
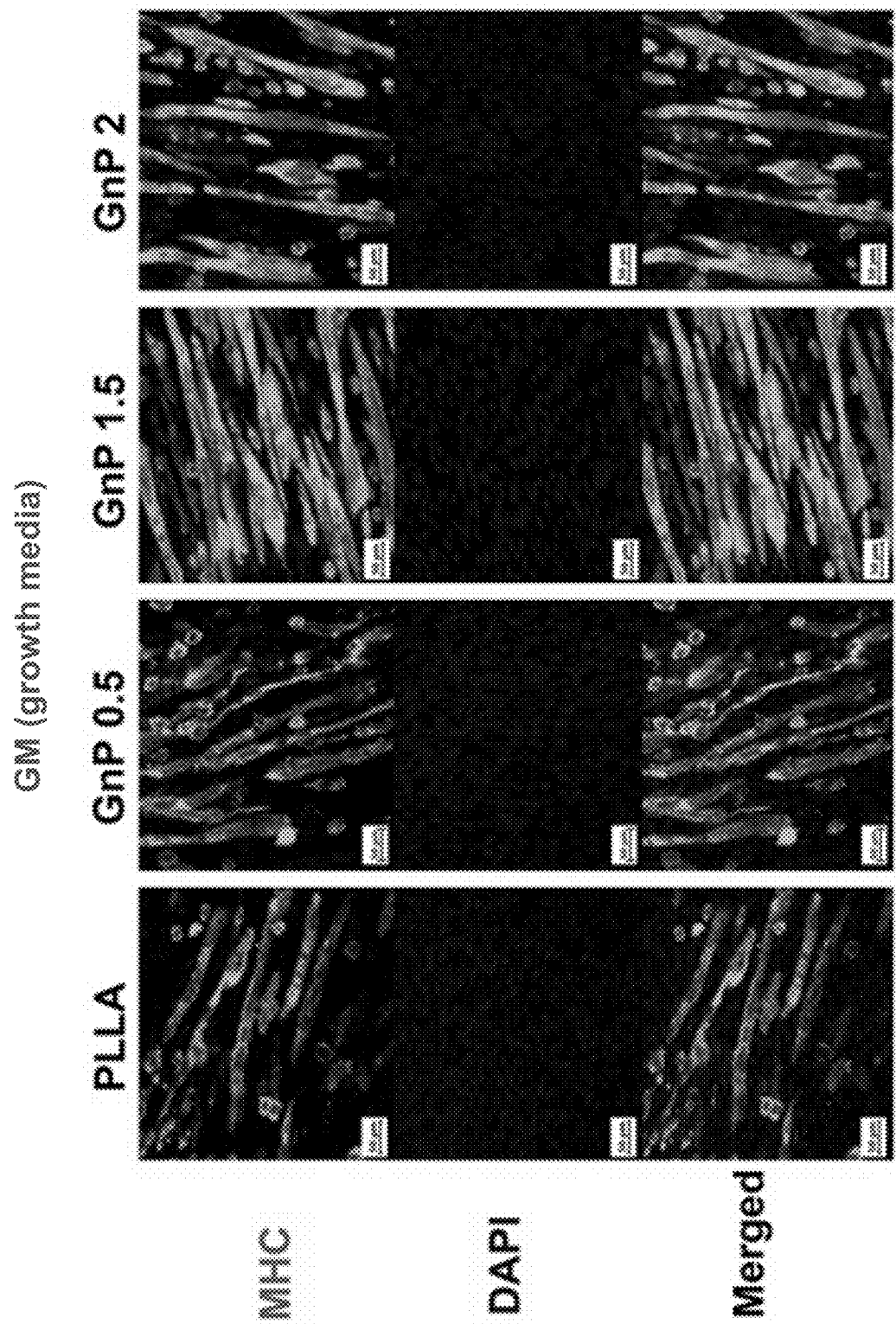
FIG. 13A through FIG. 13H show that the aligned electroconductive scaffolds successfully induced muscle cell alignment and stimulated myotube formation compared with the aligned PLLA scaffold and randomly oriented scaffolds in both GM and DM.
Figure 13B:
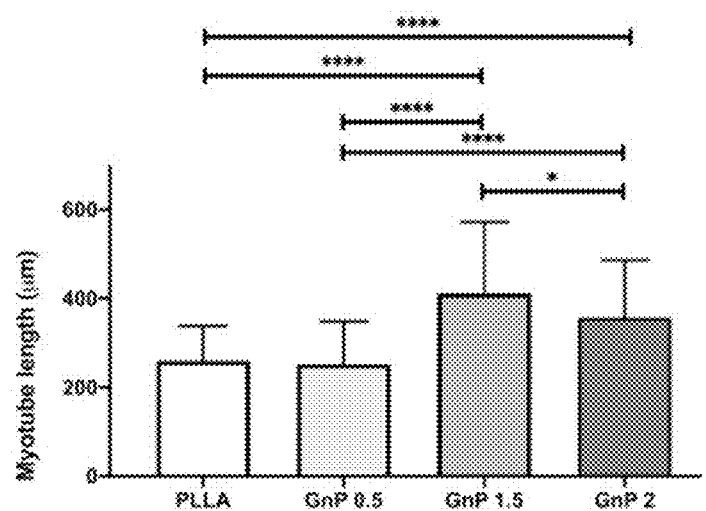
Figure 13C:
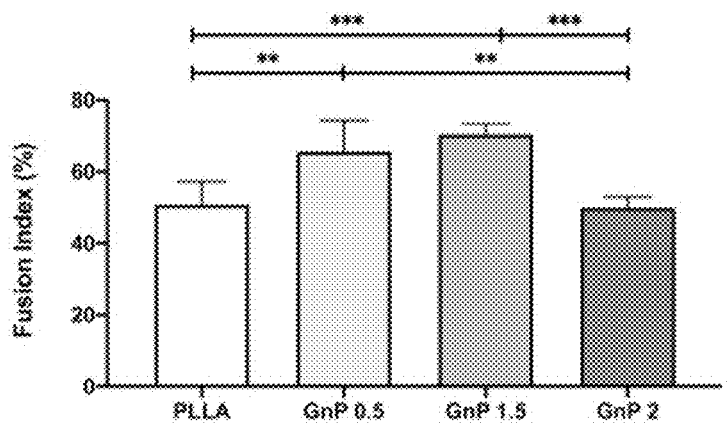
Figure 13D:
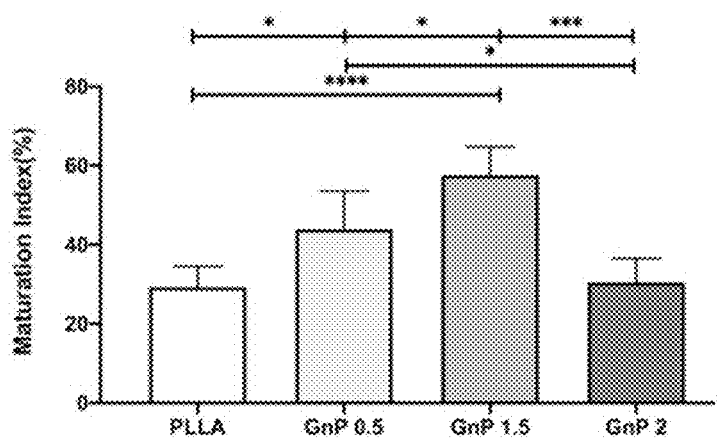
Figure 13E:
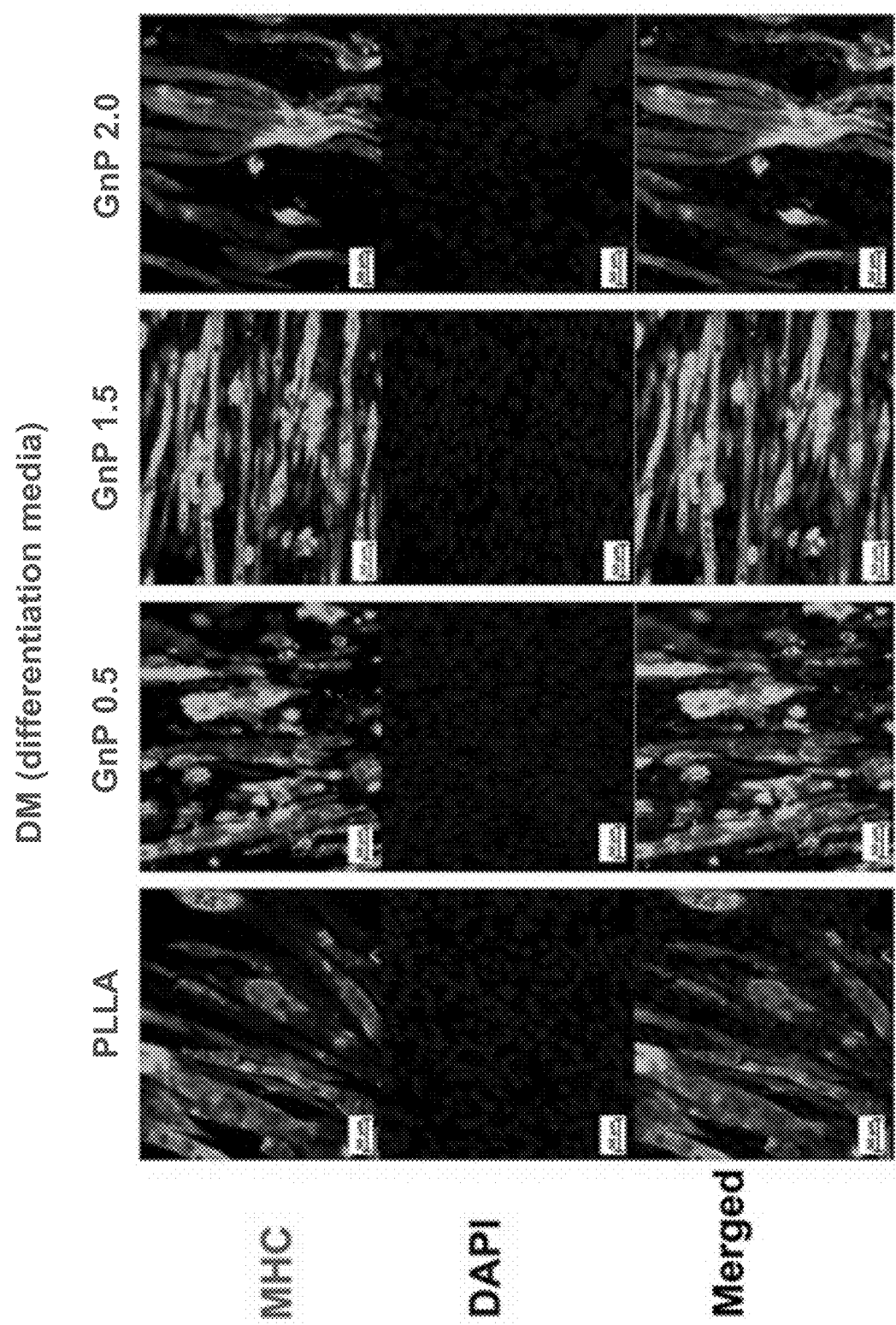
Figure 13F:
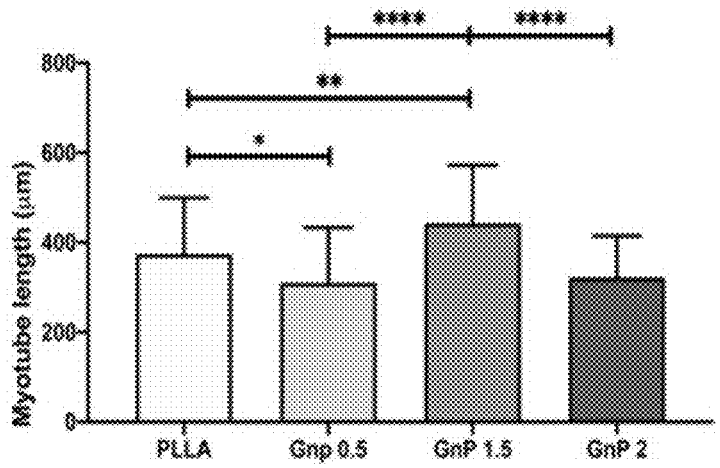
Figure 13G:
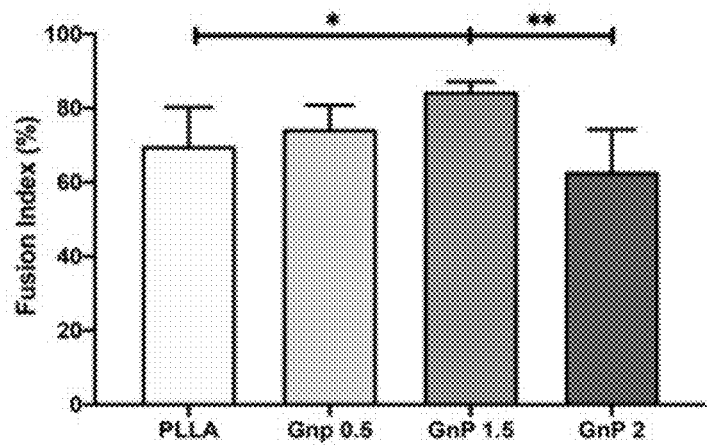
Figure 13H:
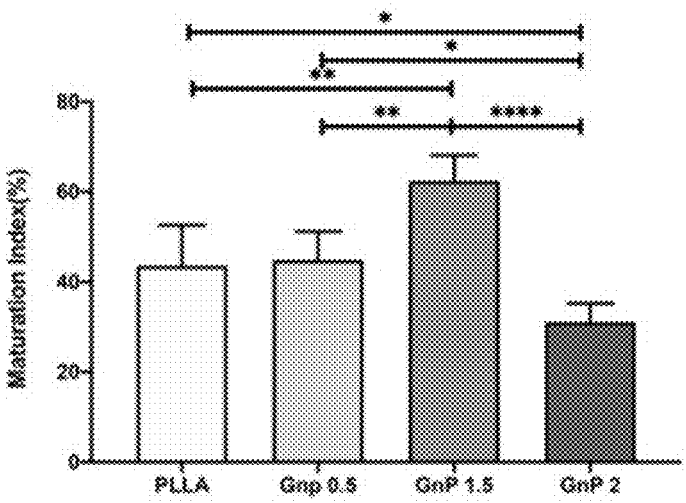

The cell viability and differentiation potential of the aligned scaffolds were analyzed by fluorescent imaging upon seeding the scaffolds with C2C12 myoblast. All scaffolds supported cell viability and growth after 1, 7, and 14 days in GM (FIG. 11). Arrows show the main directions of the aligned nanofibers, and the myoblasts aligned with nanofiber direction, inducing cell orientation.

FIGS. 12B-12E show the synergistic effects of the topographical and electrical cues on myoblast differentiation and myotube formation in GM and DM. As shown in the immunofluorescent images, all GnP scaffolds induced C2C12 myoblast to express MyoD and MyoG in both GM and DM after 3 and 5 days. MyoD plays a role in the early stage of myogenesis, while MyoG shows a late effect on skeletal muscle and is mainly involved in the fusion and differentiation of myocytes. FIG. 12 demonstrates the potential of GnP scaffolds to express myogenic regulatory factors.

FIGS. 13A-13H show that the aligned electroconductive scaffolds successfully induced muscle cell alignment and stimulated myotube formation compared with the aligned PLLA scaffold and randomly oriented scaffolds in both GM and DM. To quantify myotubes formation and maturation, the length, fusion, and maturation indices of the fused myotubes were calculated. Based on the results, the differentiation indices of the myotubes on the aligned GnP 1.5 were significantly greater than other scaffolds. The guidance cues significantly induced the myoblasts differentiation and GnP 1.5 showed the highest fusion and maturation indices compared with other scaffolds in both GM and DM.

FIGS. 13A-13D show immunofluorescent images of myotubes differentiated for 7 days on aligned scaffolds in GM and immune-stained for MHC (green) and nucleus (blue). Quantification of Myotube length,) Fusion index, Maturation index, (ns=P>0.05, *=P≤0.05, =P≤0.01, *=P≤0.001, ****=P≤0.0001; n=5). FIG. 13E-13H: Immunofluorescent images of myotubes differentiated for 7 days on aligned scaffolds in DM and immune-stained for MHC (green) and nucleus (blue). Quantification of Myotube length,) Fusion index, Maturation index, (ns=P>0.05, *=P≤0.05, =P≤0.01, *=P≤0.001, ****=P≤0.0001; n=5).

The synergistic effects of nanofibers alignment and incorporation of GnPs is shown in FIG. 14. In general, the incorporation of GnP into the aligned nanofibers can induce myotube elongation and maturation without the need for any external factors such as DM or electrical stimulation. By using GnP, myoblast differentiation showed no significant differences in GM compared with DM. However, based on the results, culturing the PLLA scaffold in DM is essential for myogenesis. Thus, it is demonstrated that GnP alone can induce myogenesis and show a similar differentiation potential to standard DM.

Figure 14A:
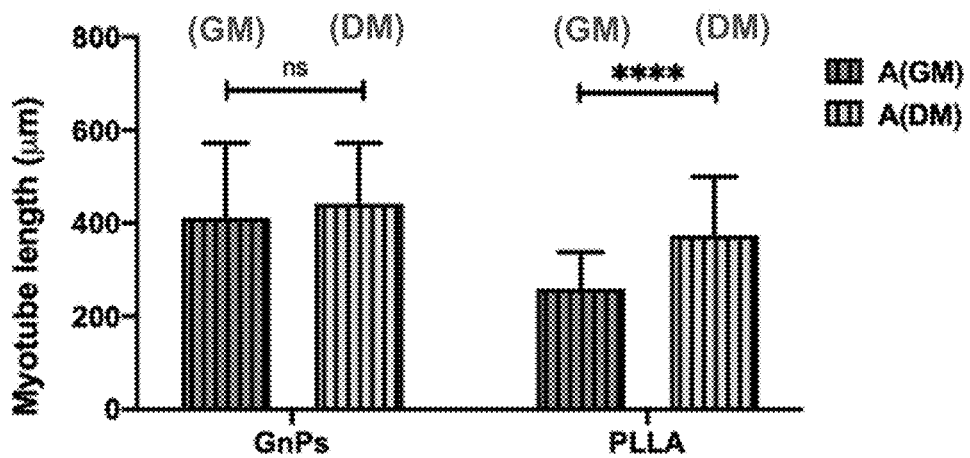
FIG. 14A through FIG. 14C show a characterization of myotubes grown on aligned scaffolds with GnPs versus PLLA, each in the presence of GM or DM.
Figure 14B:
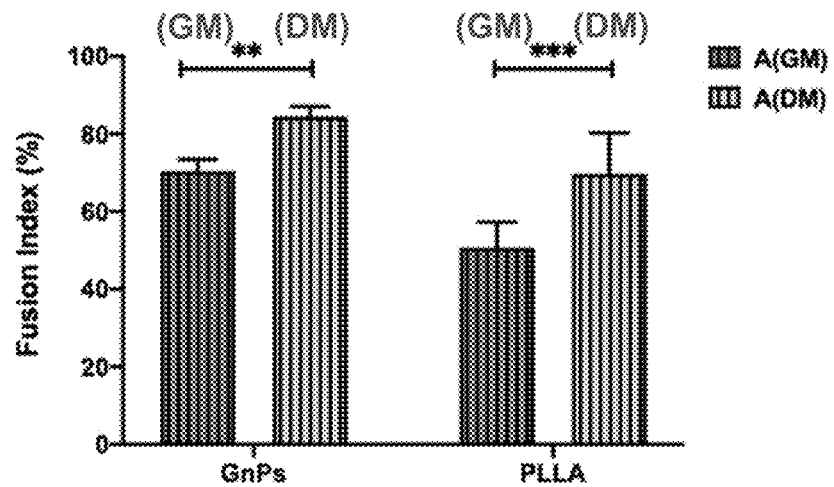
Figure 14C:
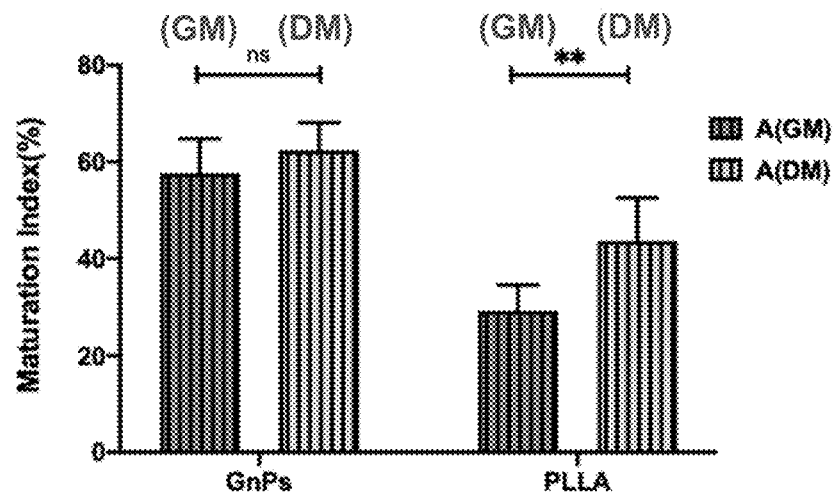
Figure 15:
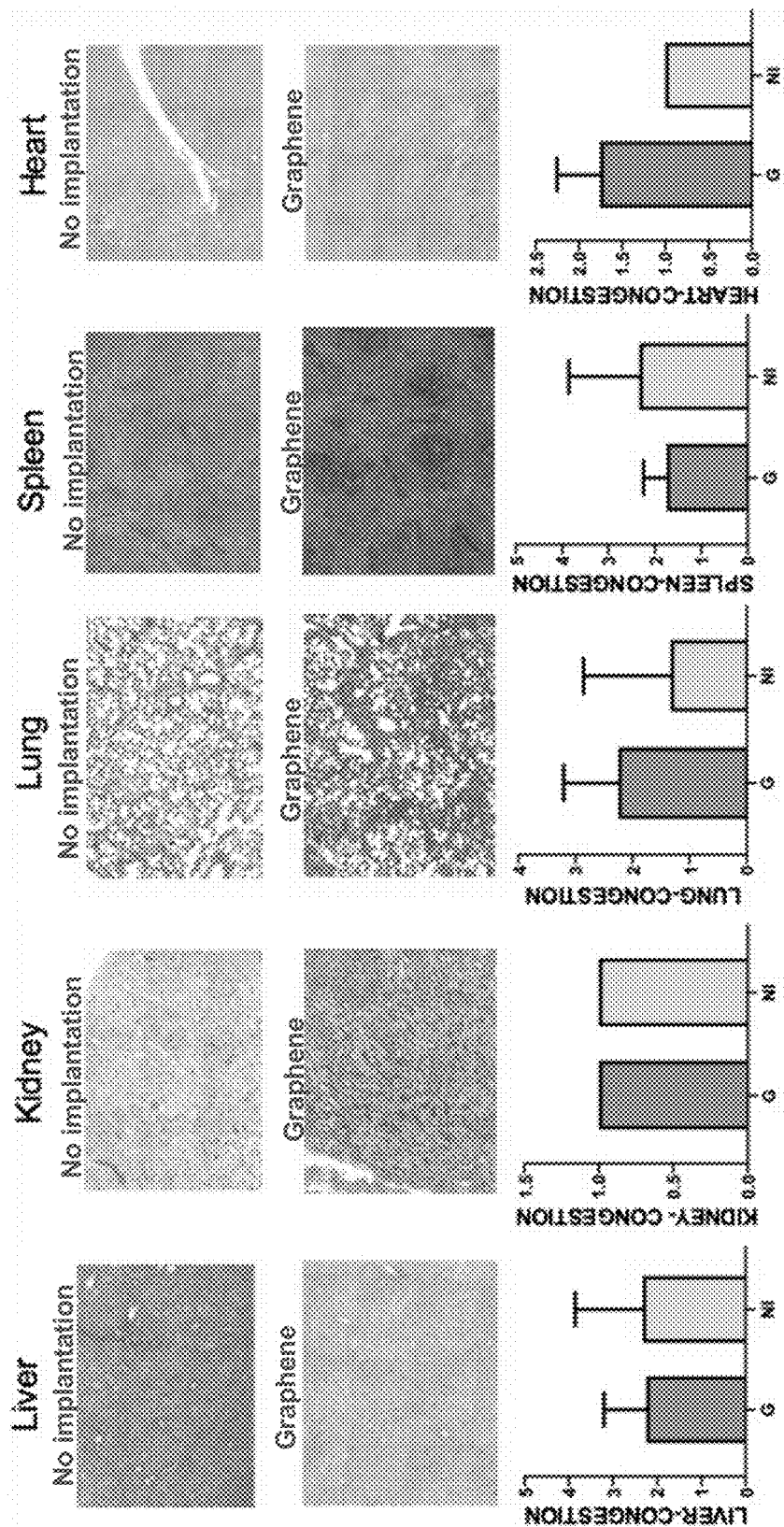
FIG. 15 shows histological images of various tissues into which GnP 1.5-containing scaffolds were implanted showing no obvious tissue damage, inflammation or toxicity.

FIGS. 14A-14C show quantification of A) Myotube length, B) Fusion index, C) Maturation index, (ns=P>0.05, *=P≤0.05, =P≤0.01, *=P≤0.001, ****=P≤0.0001; n=5).

These results demonstrate that topography has a dominant role in myotube elongation and electroactive material has a dominant role in the fusion and maturation of myotubes. Importantly, the results indicate that the combination of the topographic and electroactive guidance cues provides the synergistic effects on the elongation and maturation of myotubes.

Example 4: In Vivo Testing of Scaffolds

Following the in vitro study, the regenerative potential of GnP 1.5 was validated in a rat model of full-thickness rotator cuff tears.

Figure 5A:
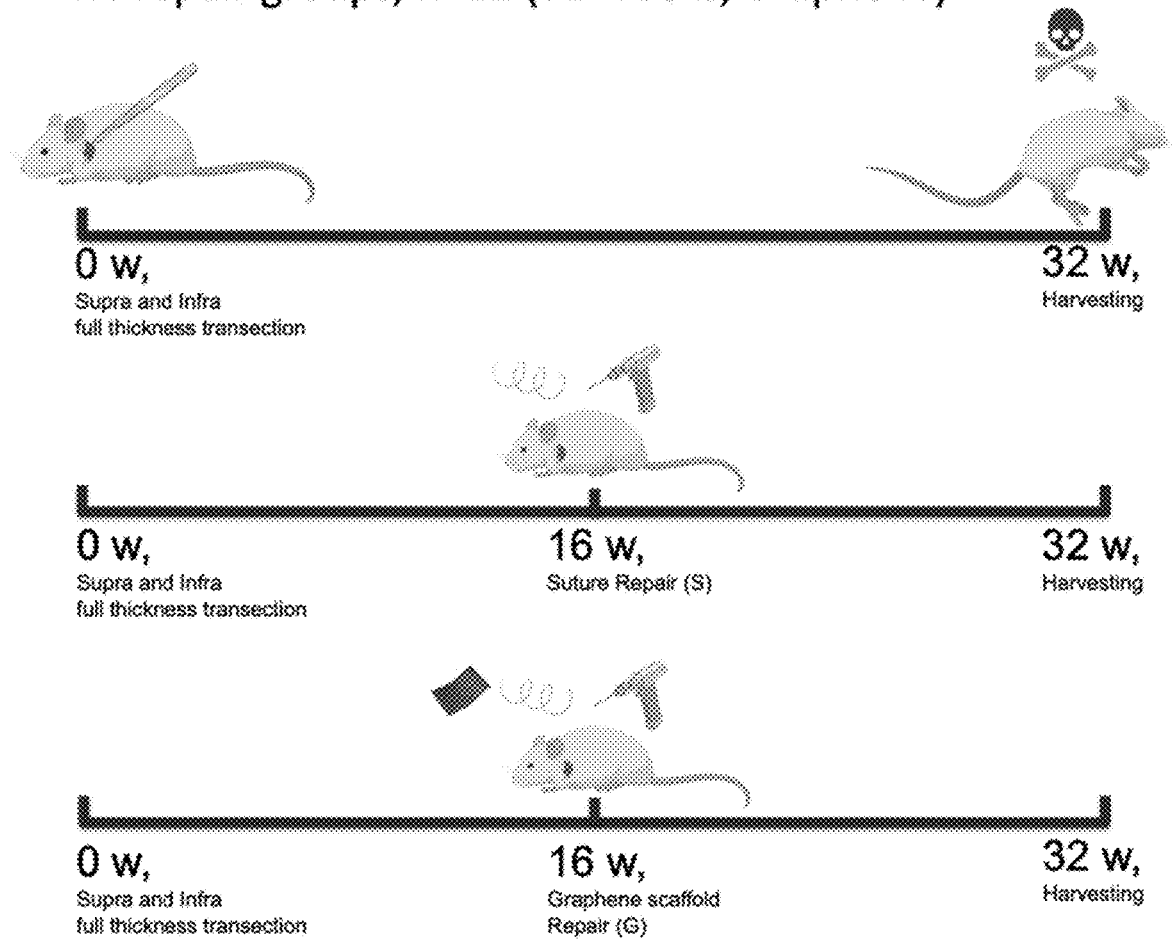
FIG. 5A through FIG. 5G show a chronic full-thickness rotator cuff tear (RCT) experimental model (FIG. 5A) and surgical procedure (FIG. 5B through FIG. 5G).
Figure 5B:
Figure 5C:
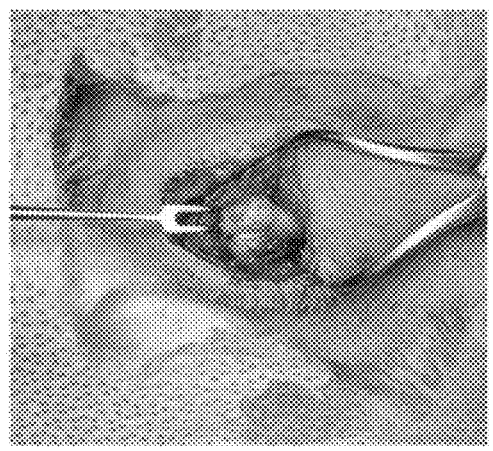

Surgical Procedure:

The surgical groups are listed in FIG. 5A. The chronic full-thickness RCT model was developed using male Sprague-Dawley rats (11 weeks old, Charles River Laboratories, Inc.). All animal experiments were performed following protocols approved by the Institutional Animal Care and Use Committee (IACUC) at the University of Connecticut (Protocol number: TE-102056-0522).

Figure 5D:
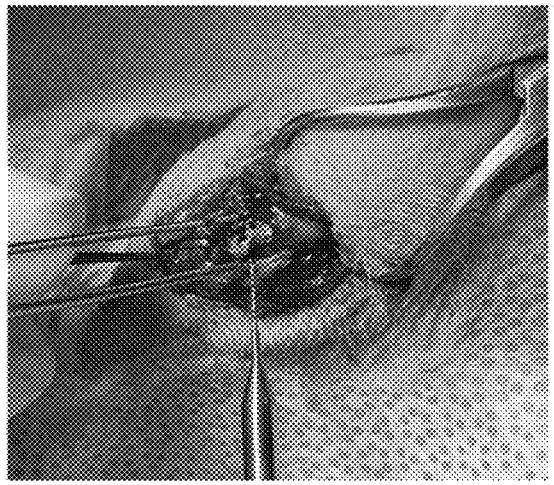
Figure 5E:
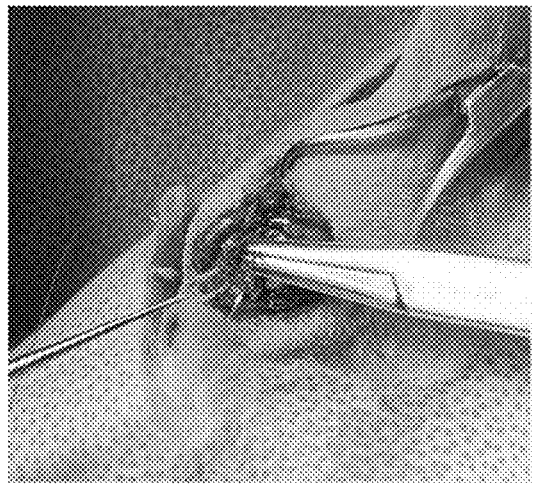
Figure 5F:
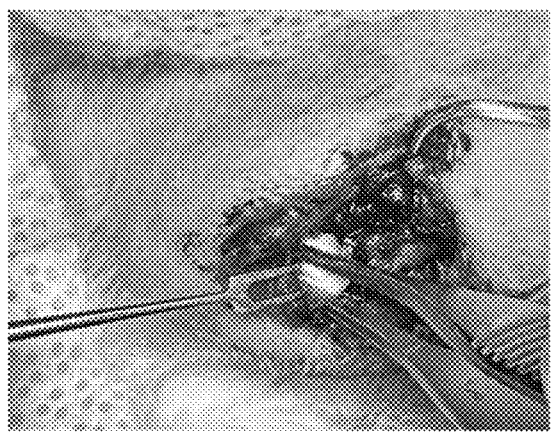
Figure 5G:

The rats were housed in a controlled environment on a light/dark cycle and fed with standard rodent chow and water. An open surgical approach was followed to create a full-thickness RCT of the supraspinatus and infraspinatus tendons in the left shoulder. Anesthesia was induced with Isoflurane (2%-3%) and maintained through a facemask for both procedures. After the skin incision, a longitudinal incision was made on the deltoid muscle to expose the RC tendons at the shoulder joint. The tendons were completely detached from the bone-tendon insertions on the humeral head, marked with a 5-0 Prolene suture (Ethicon, Johnson & Johnson Medical Ltd.), and allowed to retract. Following the defect, the muscle and skin layer were closed with 5-0 vicryl using the interrupted suture technique. The second operation to reattach the tendons was performed sixteen weeks after the injury (FIGS. 5B-5G). A tunnel was created in the cortical bone under the insertion of tendons, and surgical reattachment of the tendons was performed using the Masson-Allen suturing technique (FIGS. 5D and 5E). For the surgical repair with scaffold, a 8 mm (length)*3 mm (width) nanofibrous scaffolds were sutured on the myotendinous Junction to the belly of the supraspinatus and infraspinatus muscles. Following the implantation of the scaffolds, the overlying tissue and skin were closed (FIGS. 5F and 5G). Analgesia (Buprenorphine, 0.05-0.1 mg/kg) and antibiotics (Sulmethaoxole & Trimethoprim 40 mg/ml & 8 mg/ml) were administered according to the protocol, and the rats were kept under heat lamps until they were transferred to their cages.

Example 5: Tissue Analysis

Tissue Harvest:

Rats were sacrificed sixteen weeks after surgery. The supraspinatus and infraspinatus muscles of the surgical site and the control side (right shoulder) were harvested and used for paraffin embedding.

Histological Analysis:

Following optimized protocols, the sections were stained by Masson's Trichrome staining and Hematoxylin & Eosin to identify fibrotic tissue and muscle fiber outlines. Images were captured (DM4000B Leica Upright Microscope; Leica Microsystems) at varying magnifications.

Figure 16A:
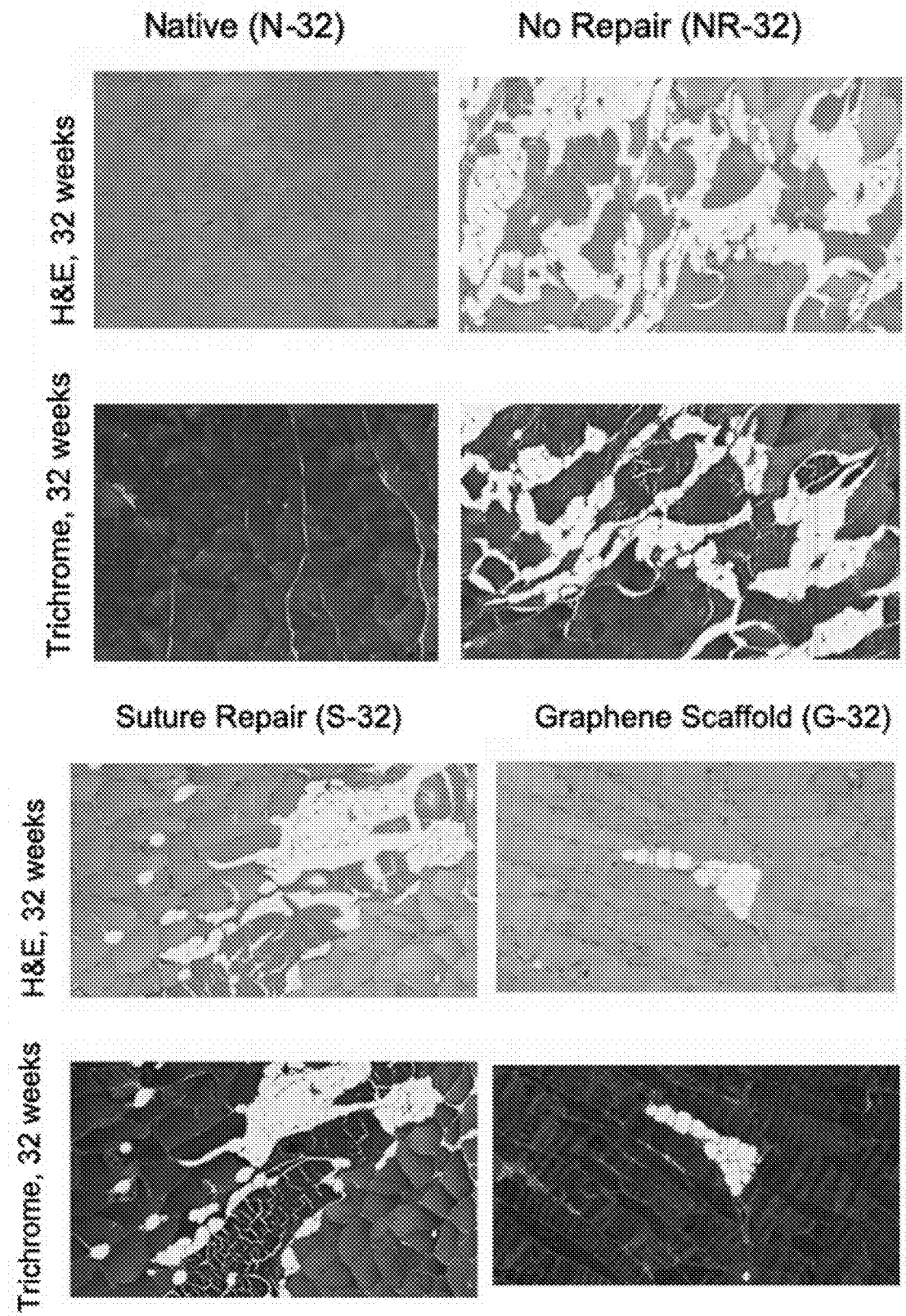
FIG. 16A shows histological results of infraspinatus muscle 16 weeks after the repair surgery, with implantation of the GnP scaffold demonstrating significantly reduced muscle atrophy (FIG. 16B), fibrosis formation (FIG. 16C), and fatty infiltration (FIG. 16D) after 32 weeks of injury compared to no repair and suture repair.
Figure 16B:
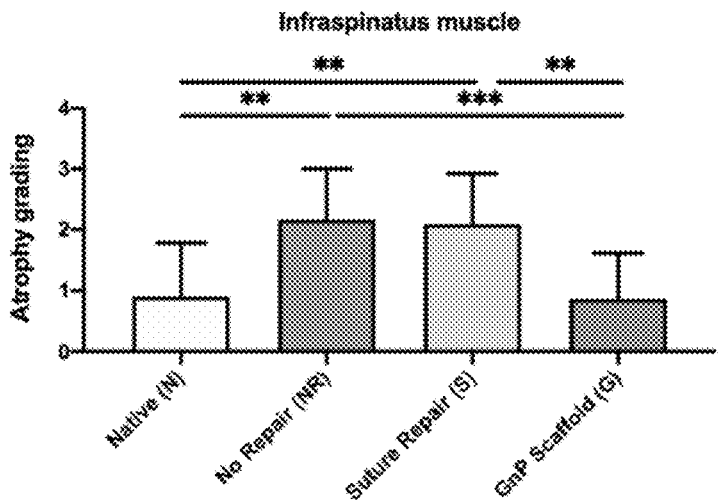
Figure 16C:
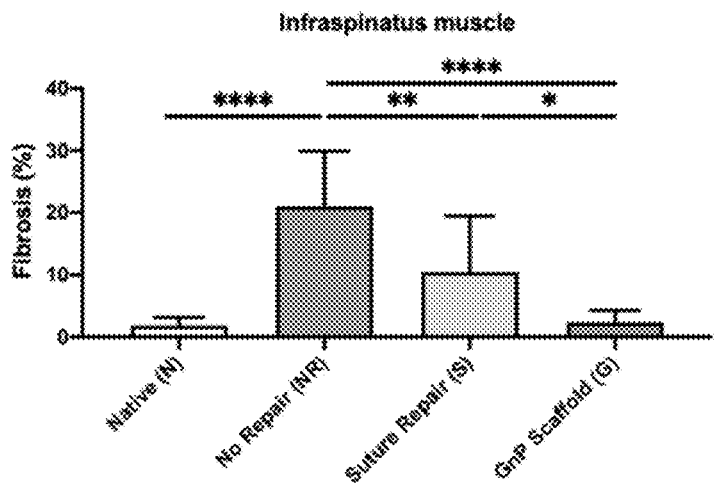
Figure 16D:
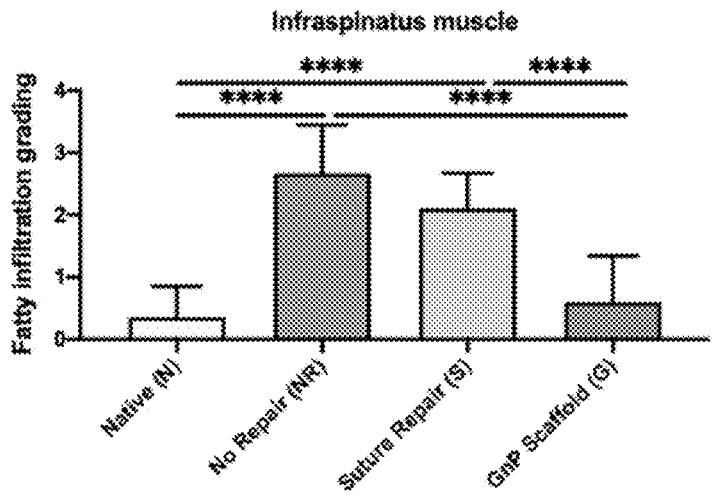
Figure 17A:
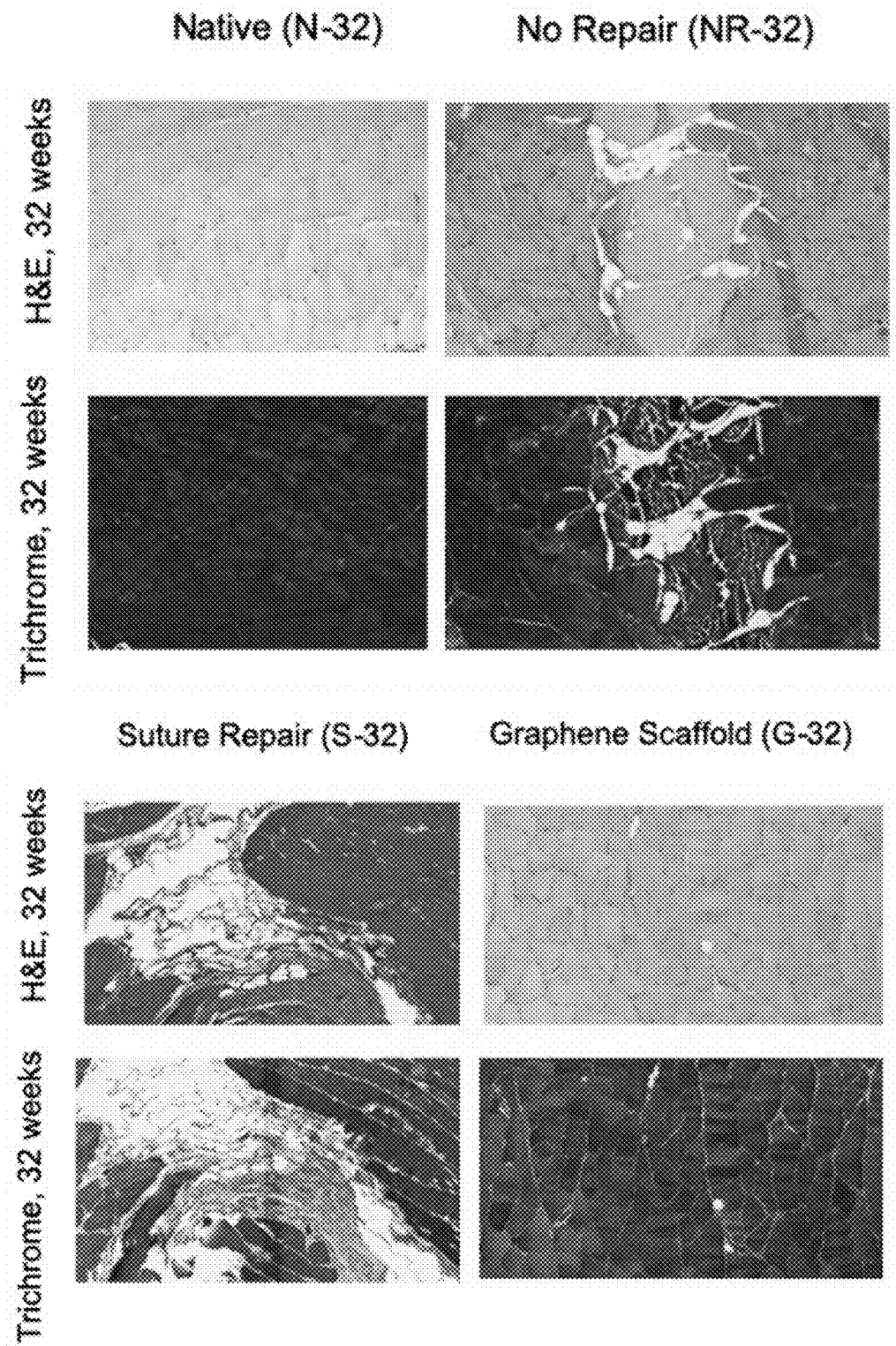
FIG. 17A shows histological results of supraspinatus muscle 16 weeks after the repair surgery, with implantation of the GnP scaffold demonstrating significantly reduced muscle atrophy (FIG. 17B), fibrosis formation (FIG. 17C), and fatty infiltration (FIG. 17D) after 32 weeks of injury.
Figure 17B:
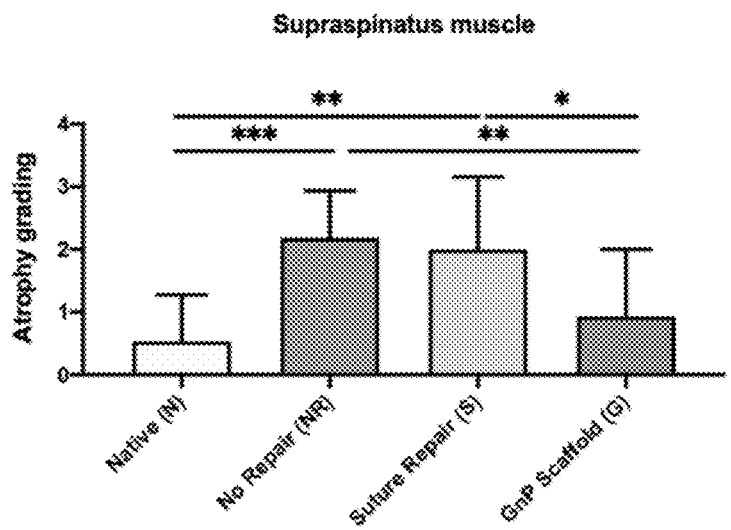
Figure 17C:
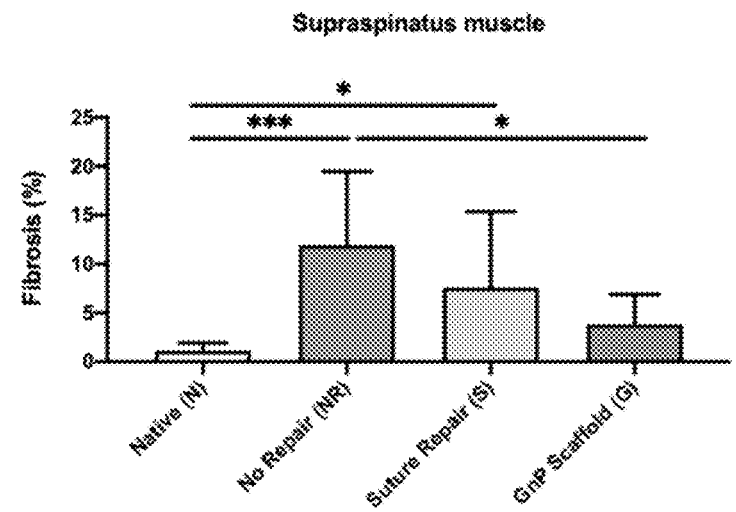
Figure 17D:
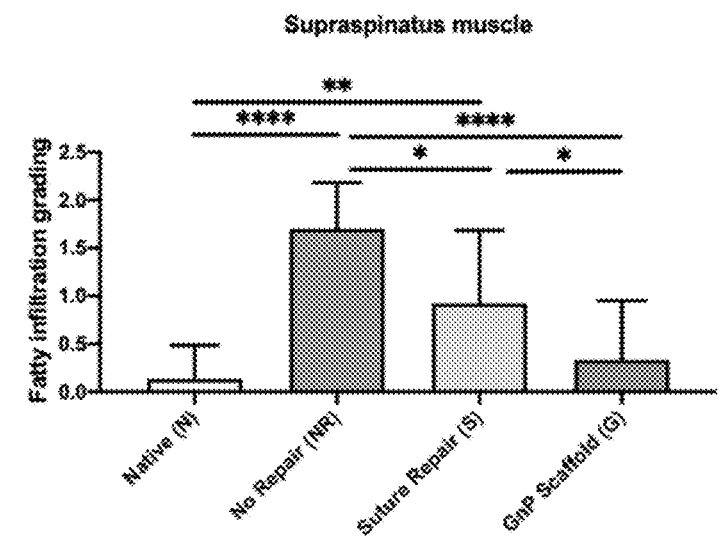

FIG. 16A shows the histological results of infraspinatus muscle 16 weeks after the repair surgery. Based on the images and quantification results, the implantation of the GnP scaffold significantly reduced muscle atrophy, fibrosis formation, and fatty infiltration after 32 weeks of injury (FIGS. 16B-D). It can be observed that suturing the tendons alone cannot reverse muscle atrophy and fatty infiltration. There are no significant differences between the native tissue and GnP implanted tissue in any quantified factors, confirming the regenerative potential of the GnP scaffold for muscle regeneration.

The results of supraspinatus muscle showed the similar regenerative potential of the GnP scaffold for muscle regeneration (FIG. 17). Although in general, supraspinatus muscle showed a lower level of atrophy and fatty infiltration compared to the infraspinatus muscle.

Similar to infraspinatus muscle, there are no statistically significant differences between native tissue, and GnP implanted tissue in any quantified factors. Implantation of GnP scaffold successfully regenerates skeletal muscle by reducing muscle atrophy, fibrosis, and fatty infiltration.

Quantification of muscle atrophy, fibrosis formation and fatty infiltration (ns=$P>0.05$, *=$P\leq0.05$, =$P\leq0.01$, *=$P\leq0.001$, ****=$P\leq0.0001$; n=10-15).

Muscle Atrophy Grading:

Muscle atrophy was graded by a few suggestive findings, such as the decreased muscle fiber size, an angular shape of muscle fibers rather than a round shape, the decreased distance between myonuclei, and centralization of myonuclei. The sections were graded semi-quantitatively from 0 to 3 (grade 0—no atrophy; grade 1—mild atrophy; grade 2—moderate atrophy; and grade 3—severe atrophy). Muscle atrophy results for infraspinatus and supraspinatus can be seen in FIGS. 16B and 17B, respectively.

Fibrosis Formation:

The degree of fibrosis was measured as the area of collagen staining fibers divided by the total area of the image after Trichrome staining. Fibrosis results for infraspinatus and supraspinatus can be seen in FIGS. 16C and 17C, respectively.

Fatty Infiltration:

The amount of fat was graded semi-quantitatively on a four-stage scale based on that used by Goutallier. The H&E stained sections were graded from 1 to 4, where Stage 0=a completely normal muscle; stage 1=muscle contains some fatty streaks; stage 2=fatty infiltration is still less than muscle; stage 3=there is as much muscle as fat; and stage 4=more fat than muscle. Fatty infiltration results for infraspinatus and supraspinatus can be seen in FIGS. 16D and 17D, respectively.

Systemic Toxicity Evaluation:

The internal organs include the liver, kidney, spleen, heart, and lung, were harvested and fixed in formalin. The samples were embedded by paraffin and evaluated through H&E staining by a pathologist. Based on the results, no obvious tissue damage, toxicological effects or inflammation were observed in the organs after implantation of the GnP scaffold. Also, based on the histological images, there was no material accumulation in the organs.

Statistics:

The t-test and one-way ANOVA tests were used to analyze the comparison among the groups. The significant differences in groups were determined by Dunnett's multiple and Tukey pairwise comparison tests. The data are expressed as means±SD and the difference of $P<0.05$ was considered statistically significant.

As described herein, electrospun nanofibers comprising pristine graphene and PLLA were fabricated with highly aligned and random orientations. The incorporation of GnPs into highly aligned nanofibers significantly increased the mechanical strength of the scaffolds. The results showed the synergistic effects of electroactive material and aligned structure on C2C12 myoblast growth and myogenic differentiation. The Examples herein show that aligned graphene-based scaffolds significantly increased myotube formation and maturation under conditions without external electrical stimulation, and without the need for DM in vitro. The implantation of the GnP scaffold in a rat chronic full-thickness RCT model after 32 weeks showed the regenerative potential of this scaffold for skeletal muscle regeneration by reducing muscle atrophy, fibrosis, and fatty infiltration. The disclosure herein indicates the regenerative potential of graphene-containing nanofibers for skeletal muscle.

What is claimed is:

1. A scaffold comprising nanofibers, wherein the nanofibers comprise a mixture of graphene nanoplatelets and a biocompatible polymer,
   wherein the biocompatible polymer is selected form the group consisting of collagen, gelatin, chitosan, hyaluronic acid (HA), silk fibroin, polylactide (PLA), polyurethane (PU), poly(ε-caprolactone) (PCL), poly (DL-lactide) (PDLLA), poly(ether ester) based on poly (ethylene oxide) (PEE based on PEO), polybutylene terephthalate (PBT), polyglycolide (PGA), poly(L-lactide-co-glycolide) (PLGA), poly(lactic acid-glycolic acid) (PLAGA), poly(ethylene-co-vinylacetate) (PEVA), poly(L-lactic acid (PLLA), and poly(L-lactide-co-ε-caprolactone) (PLLA-CL);
   wherein the nanofibers comprise an average diameter of about 400 nm to about 1200 nm; and
   wherein the graphene nanoplatelets comprise from about 0.5 wt % to about 2 wt % of the scaffold.

2. The scaffold of claim 1, wherein the scaffold comprises about 98 wt % of biocompatible polymer to about 99.5 wt % of biocompatible polymer.

3. The scaffold of claim 1, wherein the scaffold comprises about 0.5 wt % of graphene nanoplatelets to about 2 wt % of graphene nanoplatelets, or about 0.5 wt % of graphene nanoplatelets to about 1.5 wt % of graphene nanoplatelets.

4. The scaffold of claim 1, wherein the nanofibers comprise uniaxial nanofibers.

5. The scaffold of claim 1, wherein the nanofibers comprise a random orientation.

6. The scaffold of claim 1, wherein the nanofibers comprise an ordered orientation.

7. The scaffold of claim 1, wherein at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise pristine graphene nanoplatelets.

8. The scaffold of claim 1, wherein at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise functionalized graphene nanoplatelets.

9. The scaffold of claim 1, wherein at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the graphene nanoplatelets comprise pristine graphene nanoplates and functionalized graphene nanoplatelets.

10. The scaffold of claim 1, comprising a porosity of about 50% to about 99.9%, a porosity of about 55% to about 99%, a porosity of about 60% to about 95%, a porosity of about 65% to about 92.5%, a porosity of about 70% and about 90%, a porosity of about 75% and about 90%, a porosity of about 80% to about 90%, a porosity of about 82% to about 89%, or a porosity of about 83% to about 88%.

11. The scaffold of claim 1, wherein the scaffold comprises about 0.5 wt %, about 1.5 wt %, or about 2.0 wt % of graphene nanoplatelets.

12. The scaffold of claim 1, wherein the scaffold comprises about 1.5 wt % of graphene nanoplatelets.

* * * * *